United States Patent
An et al.

(10) Patent No.: US 12,415,799 B2
(45) Date of Patent: Sep. 16, 2025

(54) INDAZOLE-FUSED CYCLIC COMPOUND

(71) Applicant: Zhejiang Yangli Pharmaceutical Technology Co., Ltd., Zhejiang (CN)

(72) Inventors: Ke An, Shanghai (CN); Na Gao, Shanghai (CN); Guoping Hu, Shanghai (CN); Jian Li, Shanghai (CN); Shuhui Chen, Shanghai (CN); Deheng Sun, Shanghai (CN)

(73) Assignee: Zhejiang Yangli Pharmaceutical Technology Co., Ltd., Zhejiang (CN)

( * ) Notice: Subject to any disclaimer, the term of this patent is extended or adjusted under 35 U.S.C. 154(b) by 475 days.

(21) Appl. No.: 18/002,476

(22) PCT Filed: Jun. 28, 2021

(86) PCT No.: PCT/CN2021/102808
§ 371 (c)(1),
(2) Date: Dec. 19, 2022

(87) PCT Pub. No.: WO2022/001971
PCT Pub. Date: Jan. 6, 2022

(65) Prior Publication Data
US 2023/0242507 A1    Aug. 3, 2023

(30) Foreign Application Priority Data

| Jun. 28, 2020 | (CN) | ............ 202010599468.2 |
| Jan. 8, 2021 | (CN) | ............ 202110023776.5 |
| Feb. 7, 2021 | (CN) | ............ 202110179812.7 |
| Jun. 16, 2021 | (CN) | ............ 202110666162.9 |

(51) Int. Cl.
| C07D 403/12 | (2006.01) |
| A61K 31/395 | (2006.01) |
| A61P 35/00 | (2006.01) |
| C07D 401/12 | (2006.01) |
| C07D 401/14 | (2006.01) |
| C07D 403/14 | (2006.01) |
| C07D 491/044 | (2006.01) |

(52) U.S. Cl.
CPC ............ *C07D 401/14* (2013.01); *A61P 35/00* (2018.01); *C07D 403/12* (2013.01); *C07D 403/14* (2013.01); *C07D 491/044* (2013.01)

(58) Field of Classification Search
CPC .............. C07D 491/044; C07D 403/14; C07D 403/12; C07D 401/14; A61P 35/00
See application file for complete search history.

(56) References Cited

U.S. PATENT DOCUMENTS

| 9,714,221 B1 * | 7/2017 | Bouaboula ............ C07F 7/0812 |
| 12,157,721 B2 * | 12/2024 | Rabion ................ B01J 31/1616 |
| 2015/0291562 A1 * | 10/2015 | Crew ........................ A61P 1/00 |
| | | 435/375 |
| 2016/0058872 A1 * | 3/2016 | Crew .................... A61K 47/545 |
| | | 544/323 |

FOREIGN PATENT DOCUMENTS

| CN | 107531722 A | 1/2018 | |
| CN | 108884079 A | 11/2018 | |
| CN | 109843888 A | 6/2019 | |
| IN | 201917013679 A | 6/2019 | |
| WO | WO-2016189011 A1 * | 12/2016 | ............ A61P 35/04 |
| WO | WO-2017140669 A1 * | 8/2017 | ............ A61P 13/08 |
| WO | 2018091153 A1 | 5/2018 | |
| WO | WO-2018102725 A1 * | 6/2018 | ......... C07K 5/06165 |
| WO | 2019002441 A1 | 1/2019 | |
| WO | WO-2019199816 A1 * | 10/2019 | ........... C07D 495/14 |
| WO | 2019245974 A1 | 12/2019 | |
| WO | 2020049150 A1 | 3/2020 | |
| WO | WO-2021011634 A1 * | 1/2021 | ............ A61K 47/55 |
| WO | WO-2022084280 A1 * | 4/2022 | ............ A61P 13/08 |
| WO | WO-2022084298 A1 * | 4/2022 | ........... C07D 401/06 |
| WO | WO-2022166879 A1 * | 8/2022 | ........... C07D 401/04 |
| WO | WO-2022187588 A1 * | 9/2022 | ........... C07D 519/00 |
| WO | WO-2024006776 A1 * | 1/2024 | ........... C07D 401/14 |
| WO | WO-2024052518 A1 * | 3/2024 | ........... C07D 403/10 |

OTHER PUBLICATIONS

Jan. 30, 2024 First Office Action issued in Chinese Patent Application No. 2021800453743.
Jan. 25, 2024 First Search Report issued in Chinese Patent Application No. 2021800453743.
Jun. 4, 2024 EESR issued in European Patent Application No. 21833499.3.
Sep. 28, 2021 International Search Report issued in International Patent Application No. PCT/CN2021/102808.

(Continued)

*Primary Examiner* — Brian-Yong S Kwon
(74) *Attorney, Agent, or Firm* — Houston Beshining Law Office PLLC; Liangang Ye

(57) ABSTRACT

A novel indazole compound, a preparation method therefor, and use thereof in the preparation of drugs for treating related diseases. Specifically disclosed are a compound of formula (II) and a pharmaceutically acceptable salt thereof.

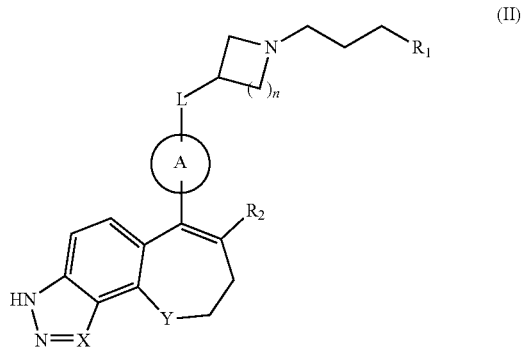

11 Claims, No Drawings

(56) References Cited

OTHER PUBLICATIONS

Sep. 28, 2021 Written Opinion of the International Searching Authority issued in International Patent Application No. PCT/CN2021/102808.

* cited by examiner

INDAZOLE-FUSED CYCLIC COMPOUND

The present application is a National Stage of International Application No. PCT/CN2021/102808, filed on Jun. 28, 2021, which claims priority of the Chinese Patent Application No. CN202010599468.2 filed on Jun. 28, 2020, the Chinese Patent Application No. CN202110023776.5 filed on Jan. 8, 2021, the Chinese Patent Application No. CN202110179812.7 filed on Feb. 7, 2021 and the Chinese Patent Application No. CN202110666162.9 filed on Jun. 16, 2021, the contents of which are incorporated herein by reference in their entireties.

TECHNICAL FIELD

The present disclosure relates to a new class of indazole-fused cyclic compounds, a preparation method therefor, and a use thereof in the manufacture of a medicament for the treatment of related diseases.

BACKGROUND

According to WHO statistics, breast cancer has become the second highest incidence cancer in the world, and is also a cancer with the highest incidence rate in women. After years of research, the effect of the estrogen-estrogen receptor signaling pathway in the development of breast cancer has been determined; and the estrogen receptor (ER) has also been developed into the most important biomarker of breast cancer. By expressing estrogen receptor as a discriminant index, breast cancer can be divided into estrogen receptor positive breast cancer and estrogen receptor negative breast cancer; wherein, estrogen receptor positive breast cancer accounts for 70% or more of the total number of breast cancer patients.

Endocrine therapy (ET) targeting the estrogen-estrogen receptor signaling pathway in breast cancer cells has become the first choice for the treatment of estrogen receptor positive breast cancer because of its minimal harm and significant efficacy. The first-line endocrine therapy is mainly aromatase inhibitor (AI). Although the aromatase inhibitor letrozole has shown good efficacy in the treatment of estrogen receptor positive breast cancer, with the use of two types of drugs, the tolerance of $ER^+$ breast cancer to aromatase inhibitor has become more and more prominent. A large number of studies have shown that for aromatase inhibitor, estrogen receptor may mutate mainly at Y537X, so that the mutated estrogen receptor can maintain its agitated conformation in the absence of estrogen and continue to function as the receptor to promote breast cancer cell proliferation. Fulvestrant, the only marketed selective estrogen receptor down-regulator, has shown good efficacy in the treatment of breast cancer resistant to hormone therapy. However, there are many problems with fulvestrant for the treatment of breast cancer with AI-resistant ER mutation. First, because of the poor pharmacokinetic properties, fulvestrant exhibits close to zero oral bioavailability; at the same time, fulvestrant has a high blood clearance rate. For the above two reasons, this drug can only be administered by intramuscular injection. However, because of the strong lipophilic structure, there are serious problems in the tissue distribution of fulvestrant administered by intramuscular injection, and clinically, only about 50% of breast cancer patients who used fulvestrant show clinical response. Due to the poor pharmacokinetic properties, the approved dose of fulvestrant can't completely degrade ER, especially the mutated ER at the corresponding concentration of tissues, and this therapeutic schedule is not the best choice for AI-resistant ER mutated breast cancer. Therefore, the development of drugs with better pharmacokinetic properties and targeting ER-mutated breast cancer remains an unmet medical need.

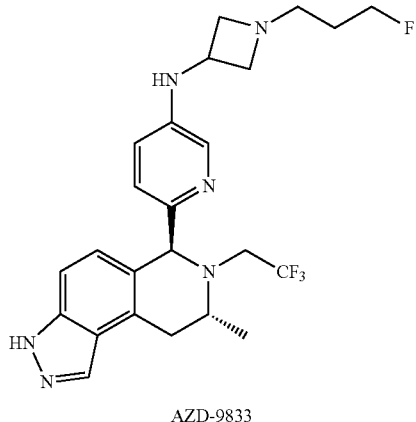 [SMILES: C[C@@H]1Cc2c(ccc3[nH]ncc23)[C@@H](c2ccc(NC3CN(CCCF)C3)cn2)N1CC(F)(F)F]

AZD-9833

WO2018/077630A1 reports that AstraZeneca is currently developing a new generation of a non-covalent estrogen receptor antagonist, AZD-9833, for the treatment of $ER^+$ breast cancer, and a clinical phase II trial of this molecule for the treatment of $ER^+/HER^{2-}$ breast cancer is ongoing. WO2019/245974A1 and WO2020/049150A1 respectively report a new generation of non-covalent estrogen receptor antagonists GDC-9545 and SAR439859 currently being developed by Genetech and Sanofi, both of which are currently in clinical phase I trial.

CONTENT OF THE PRESENT INVENTION

The present disclosure provides a compound represented by formula (II) or a pharmaceutically acceptable salt thereof

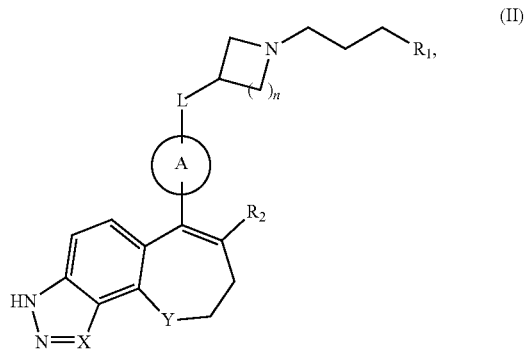

wherein, n is 1 or 2;

X is selected from N and $CR_3$;

Y is selected from —O— and —$CH_2$—;

L is selected from —O—, —$NH(CH_3)$— and —NH—;

ring A is selected from phenyl, pyridyl, pyrazinyl and pyrimidyl, and the phenyl, pyridyl, pyrazinyl and pyrimidyl are each independently and optionally substituted by 1, 2 or 3 $R_a$;

R₁ is selected from CN and F;
R₂ is selected from C₁₋₆ alkyl, C₁₋₆ alkoxy and C₃₋₆ cycloalkyl, and the C₁₋₆ alkyl, C₁₋₆ alkoxy and C₃₋₆ cycloalkyl are each independently and optionally substituted by 1, 2 or 3 R_b;
R₃ is selected from D, F and H;
R_a is each independently selected from H, D, F, Cl, Br, I, OH, CN, OCH₃, OCH₂CH₃, C₁₋₄ alkyl,

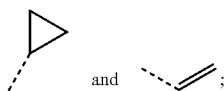

R_b is each independently selected from F, Cl, Br, I, CN, OH and OCH₃.

In some embodiments of the present disclosure, the ring A is selected from

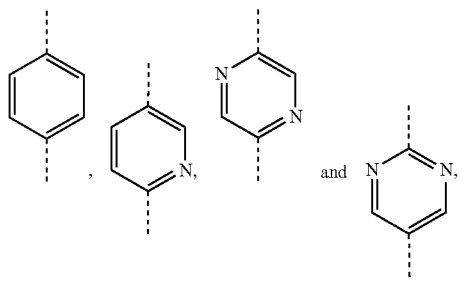

and the

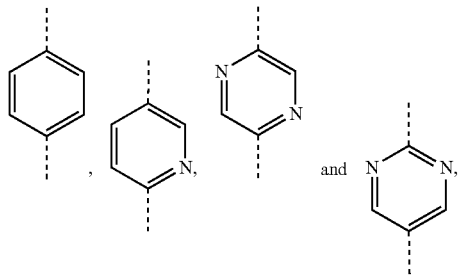

and are each independently and optionally substituted by 1, 2 or 3 R_a, and the other variables are as defined herein.

In some embodiments of the present disclosure, the R_a is each independently selected from H, D, F, Cl, OH, CN, OCH₃ and CH₃, and the other variables are as defined herein.

In some embodiments of the present disclosure, the ring A is selected from

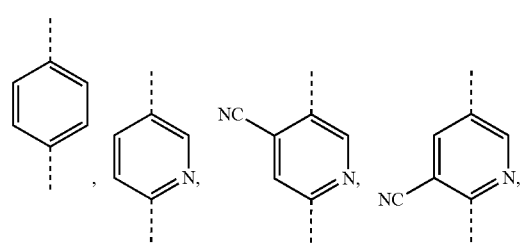

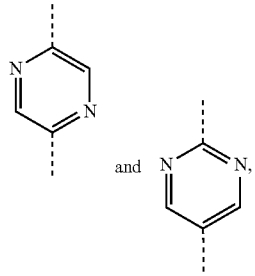

and the other variables are as defined herein.

In some embodiments of the present disclosure, the R₂ is selected from C₁₋₃ alkyl and C₁₋₃ alkoxy, and the C₁₋₃ alkyl and C₁₋₃ alkoxy are each independently and optionally substituted by 1, 2 or 3 R_b, and the other variables are as defined herein.

In some embodiments of the present disclosure, the R₂ is selected from

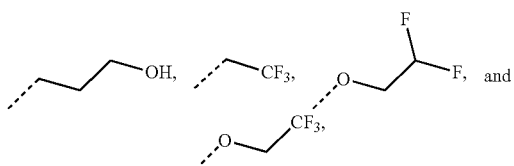

and the other variables are as defined herein.

In some embodiments of the present disclosure, the compound is selected from

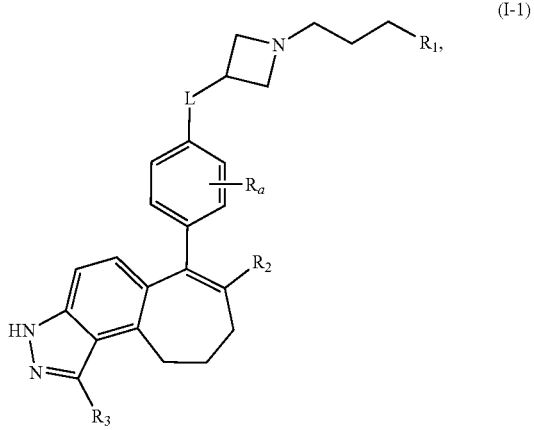

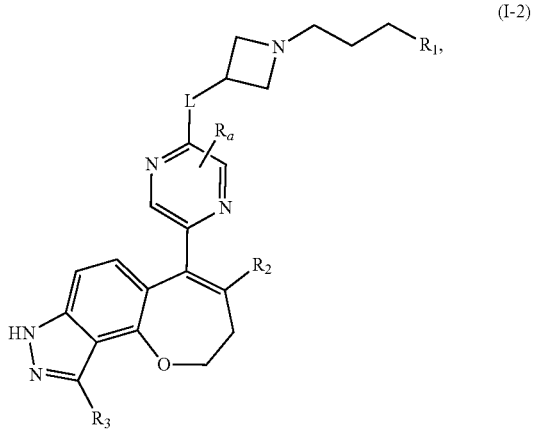

-continued
(I-3)
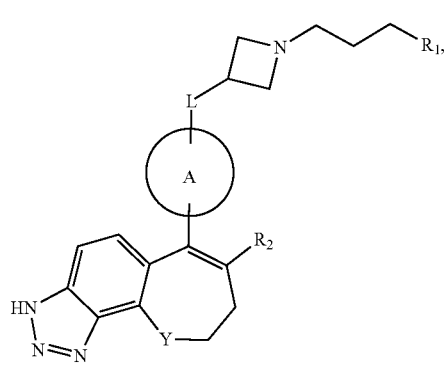
(I-4)
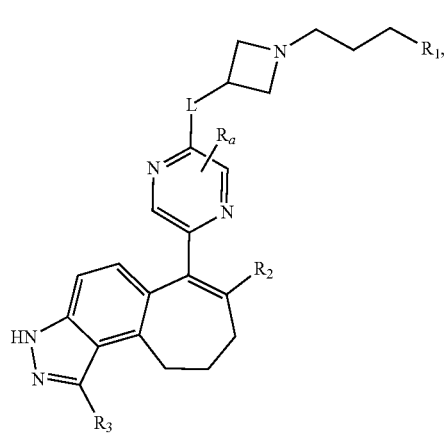
(I-5)
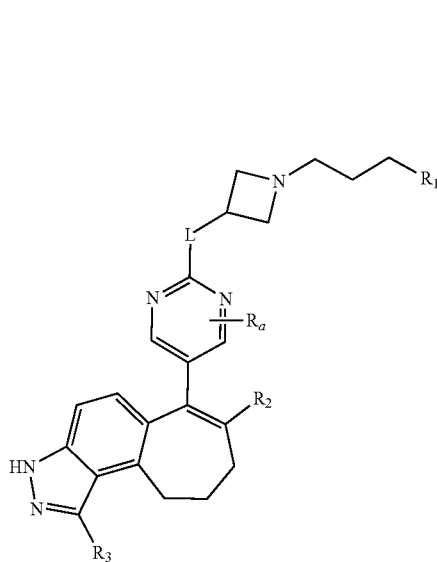
and
-continued
(II-1)
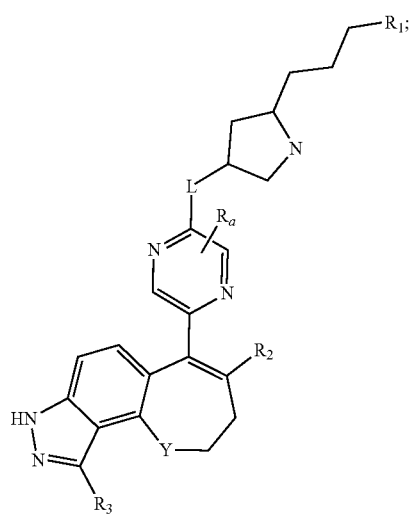
wherein, Y, L, R$_1$, R$_2$, R$_3$, R$_a$ and ring A are as defined herein.
In some embodiments of the present disclosure, the compound is selected from
(II-1)
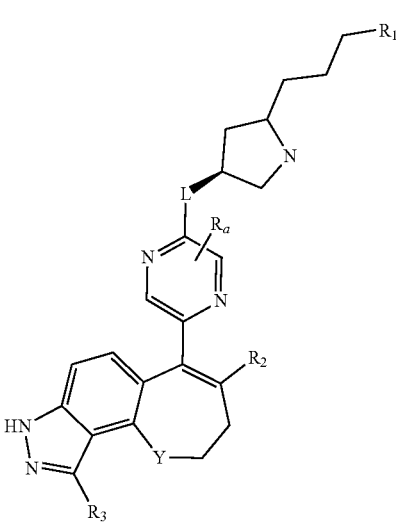
and
(II-1)
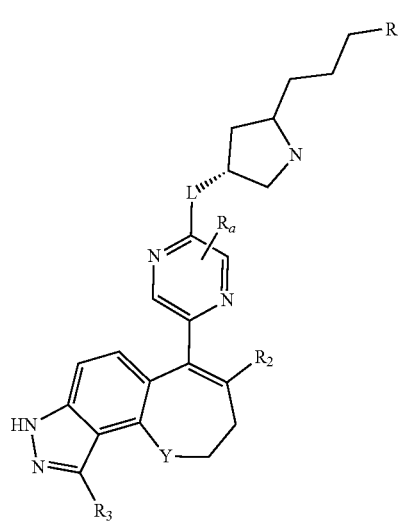

The present disclosure provides a compound represented by formula (I) or a pharmaceutically acceptable salt thereof

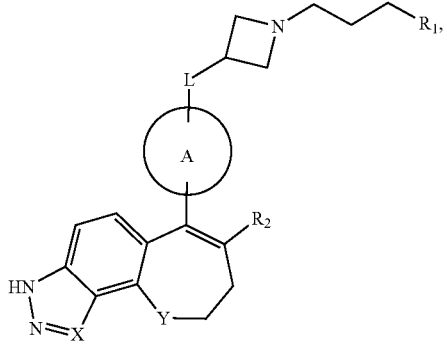
(I)

wherein,
X is selected from N and $CR_3$;
Y is selected from —O— and —$CH_2$—;
L is selected from —O—, —$NH(CH_3)$— and —NH—;
ring A is selected from phenyl, pyridyl, pyrazinyl and pyrimidyl, and the phenyl, pyridyl, pyrazinyl and pyrimidyl are each independently and optionally substituted by 1, 2 or 3 $R_a$;
$R_1$ is selected from CN and F;
$R_2$ is selected from $C_{1-6}$ alkyl and $C_{3-6}$ cycloalkyl, and the $C_{1-6}$ alkyl and $C_{3-6}$ cycloalkyl are each independently and optionally substituted by 1, 2 or 3 $R_b$;
$R_3$ is selected from D, F and H;
$R_a$ is each independently selected from H, D, F, Cl, Br, I, OH, $OCH_3$, $OCH_2CH_3$, $C_{1-4}$ alkyl,

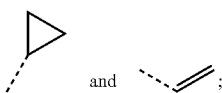;

$R_b$ is each independently selected from F, Cl, Br, I, CN, OH and $OCH_3$.

In some embodiments of the present disclosure, in the compound represented by formula (I), the ring A is selected from phenyl and pyridyl, and the phenyl and pyridyl are each independently and optionally substituted by 1, 2 or 3 $R_a$, and the other variables are as defined herein.

In some embodiments of the present disclosure, in the compound represented by formula (I), the ring A is selected from

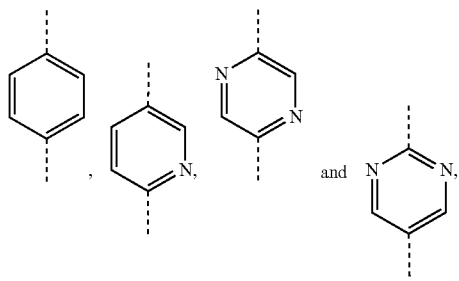

and the

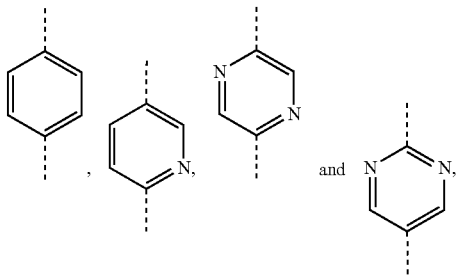

are each independently and optionally substituted by 1, 2 or 3 $R_a$, and the other variables are defined herein.

In some embodiments of the present disclosure, in the compound represented by formula (I), the $R_a$ is each independently selected from H, D, F, Cl, OH, $OCH_3$ and $CH_3$, and the other variables are as defined herein.

In some embodiments of the present disclosure, in the compound represented by formula (I), the ring A is selected from phenyl and pyridyl, and the other variables are as defined herein.

In some embodiments of the present disclosure, in the compound represented by formula (I), the $R_2$ is selected from $C_{1-3}$ alkyl, and the $C_{1-3}$ alkyl is optionally substituted by 1, 2 or 3 $R_b$, and the other variables are as defined herein.

In some embodiments of the present disclosure, in the compound represented by formula (I), the $R_2$ is selected from

and the other variables are as defined herein.

In some embodiments of the present disclosure, in the compound represented by formula (I), the compound is selected from

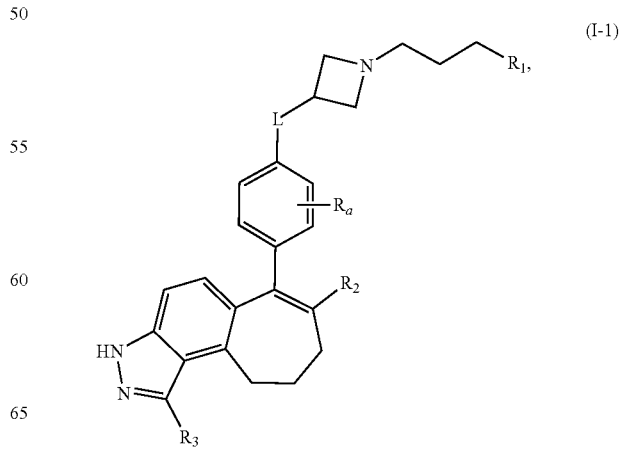
(I-1)

-continued
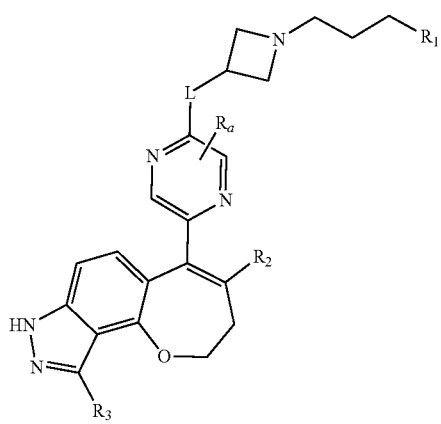
(I-2)
and
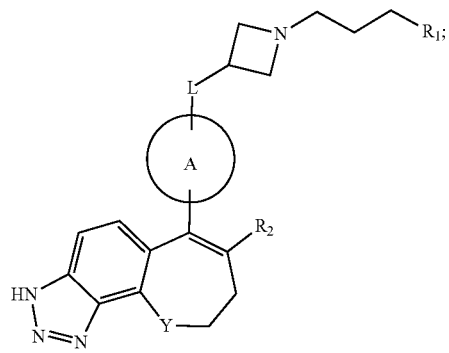
(I-3)
wherein, Y, L, R₁, R₂, R$_a$ and ring A are as defined herein.
In some embodiments of the present disclosure, in the compound represented by formula (I), the compound is selected from
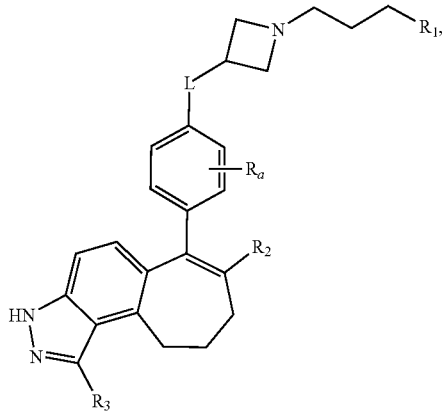
(I-1)
-continued
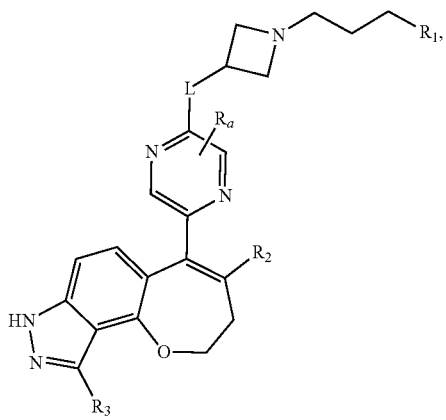
(I-2)
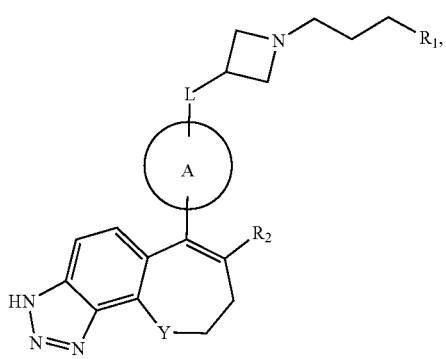
(I-3)
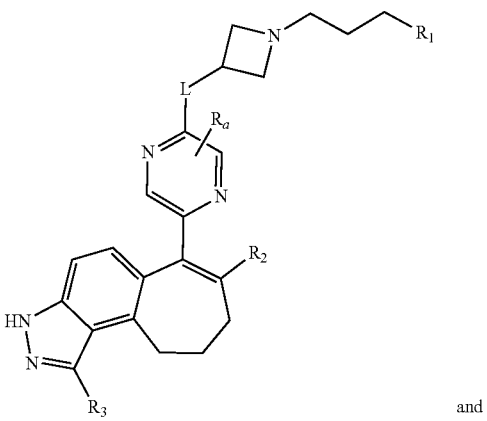
(I-4)
and
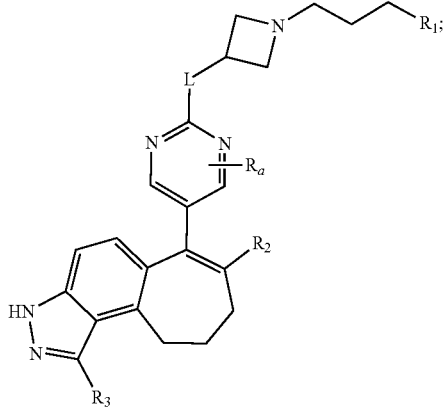
(I-5)
wherein, Y, L, R₁, R₂, R$_a$ and ring A are as defined herein.

Some embodiments of the present disclosure are formed by any combination of the above variables.
The present disclosure also provides a compound represented by the following formula or a pharmaceutically acceptable salt thereof
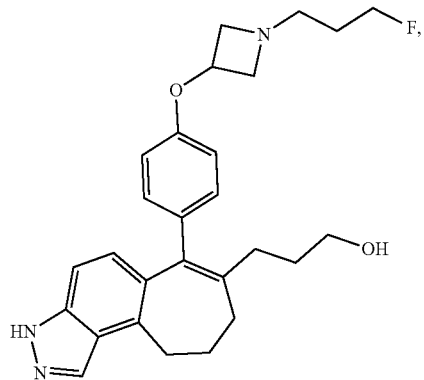
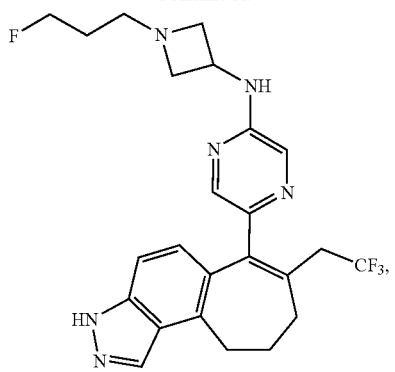
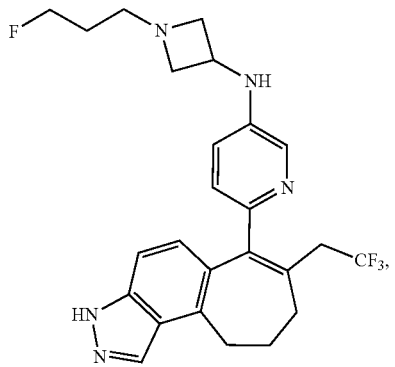
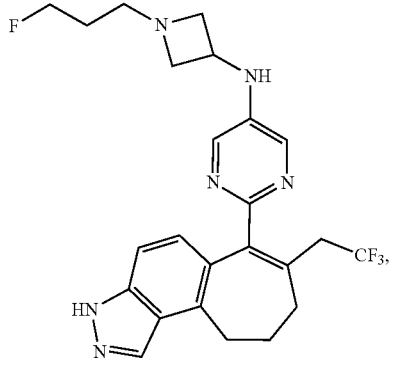
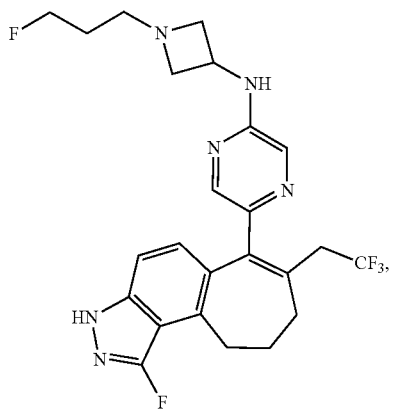

-continued
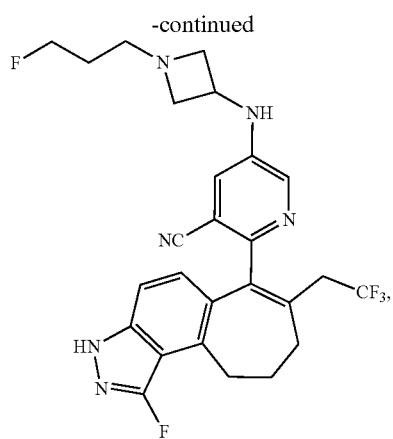
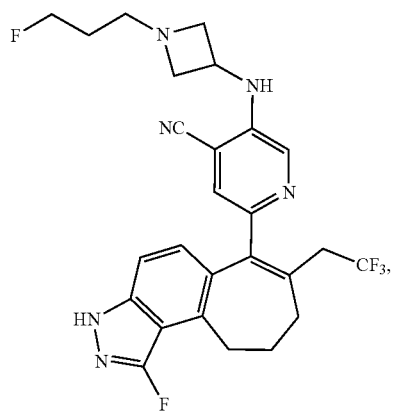
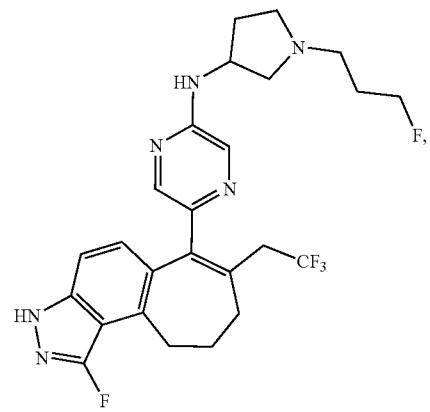
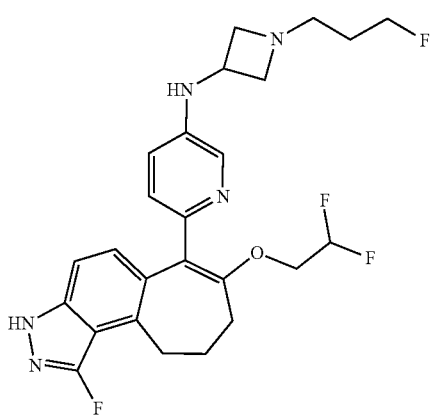
and
-continued
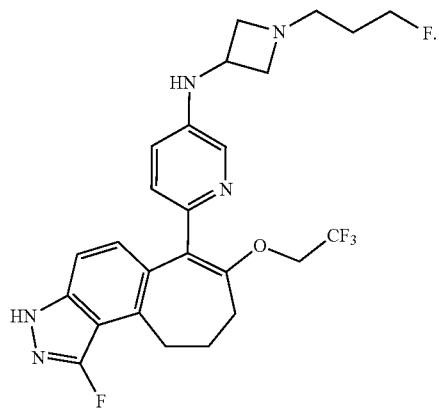 [SMILES: FCCCN1CC(Nc2ccc(C3=C(OCC(F)(F)F)CCCc4c3ccc3[nH]nc(F)c43)nc2)C1]
In some embodiments of the present disclosure, the compound is selected from
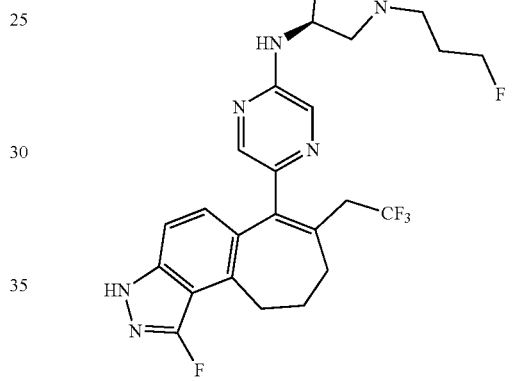
and
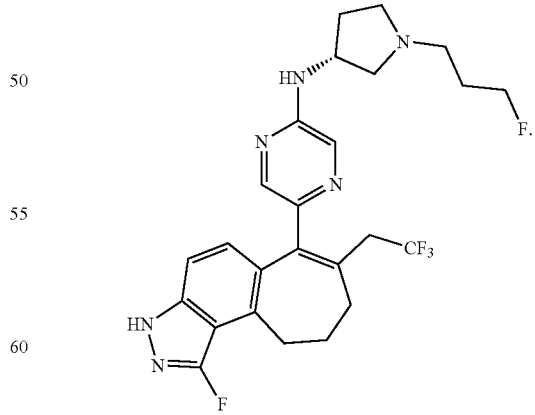
The present disclosure provides a compound represented by the following formula or a pharmaceutically acceptable salt thereof

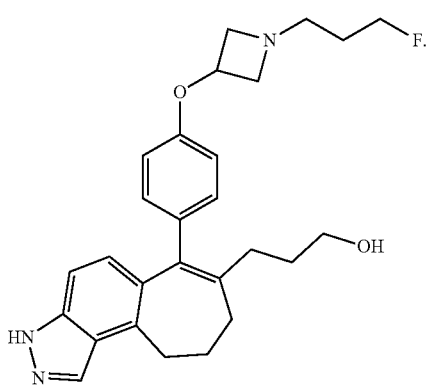 [SMILES: OCCCC1=C(c2ccc(OC3CN(CCCF)C3)cc2)c2ccc3[nH]ncc3c2CCC1]

In some embodiments of the present disclosure, the pharmaceutically acceptable salt thereof is selected from

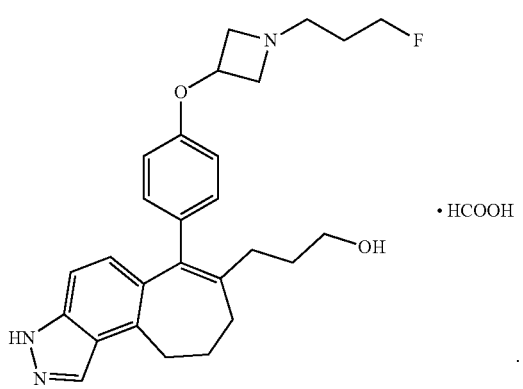 [SMILES: OCCCC1=C(c2ccc(OC3CN(CCCF)C3)cc2)c2ccc3[nH]ncc3c2CCC1 ; "· HCOOH"]

In some embodiments of the present disclosure, the pharmaceutically acceptable salt is selected from formate.

The present disclosure also provides a use of the compound or the pharmaceutically acceptable salt thereof in the manufacture of a medicament in the treatment of breast cancer.

In some embodiments of the present disclosure, the breast cancer is estrogen receptor positive breast cancer.

Technical Effects

The compound of the present disclosure has obvious degradation effect on ERα in vitro, has significant anti-proliferation activity on MCF-7 cells, has good pharmacokinetic properties and significant in vivo and in vitro efficacy, and is expected to become an excellent drug for breast cancer, especially ER mutated breast cancer.

Definition and Description

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and a salt of amino acid (such as arginine and the like), and a salt of an organic acid such as glucuronic acid and the like. Certain specific compounds of the present disclosure contain both basic and acidic functional groups and can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with heavy hydrogen, and the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is a keto group (i.e., =O), it means two hydrogen atoms are substituted. Positions on an aromatic ring cannot be substituted by a keto group. The term "optionally substituted" means an atom can be substituted with a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bonds linking thereto so as to meet the corresponding valence. The chemical bond between the site and other groups can be represented by a straight solid bond ( 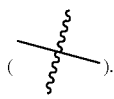 ), a straight dashed bond (  ) or a wavy line

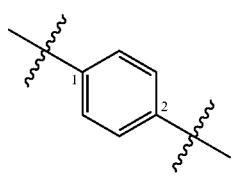 [SMILES: *c1ccc(*)cc1]

For example, the straight solid bond in —OCH₃ means that it is linked to other groups through the oxygen atom in the group; the straight dashed bonds in

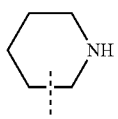

means that it is linked to other groups through the two ends of nitrogen atom in the group; the wave lines in

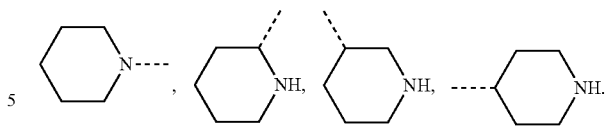

means that the phenyl group is linked to other groups through carbon atoms at position 1 and position 2;

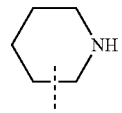

means that it can be linked to other groups through any linkable sites on the piperidinyl by one chemical bond, including at least four types of linkage, including

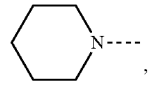

Even though the H atom is drawn on the —N—, still includes the linkage of merely when one chemical bond was connected, the H of this site will be reduced by one to the corresponding monovalent piperidinyl.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, etc.; it can be monovalent (such as methyl), bivalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, t-butyl), pentyl (including n-pentyl, isopentyl and neopentyl), hexyl, etc.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$, $C_{1-3}$ and $C_{2-3}$ alkyl, etc. It can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group consisting of 1 to 3 carbon atoms. The $C_{1-3}$ alkyl group includes $C_{1-2}$ and $C_{2-3}$ alkyl, etc; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-6}$ alkoxy" refers to an alkyl containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentoxy and neopentyloxy), hexyloxy, etc.

Unless otherwise specified, the term "$C_{1-3}$ alkoxy" refers to an alkyl containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, "$C_{3-6}$ cycloalkyl" refers to a saturated cyclic hydrocarbon group consisting of 3 to 6 carbon atoms, which is monocyclic and bicyclic systems, and the $C_{3-6}$ cycloalkyl including $C_{3-5}$, $C_{4-5}$ and $C_{5-6}$ cycloalkyl, etc.; it may be monovalent, divalent or multivalent. Examples of $C_{3-6}$ cycloalkyl include, but are not limited to, cyclopropyl, cyclobutyl, cyclopentyl, cyclohexyl, etc.

The formate of the compound of the present disclosure is added with saturated sodium carbonate solution to adjust the pH to be greater than 9, and the free alkali of the compound is obtained by high performance liquid chromatography (neutral, ammonium bicarbonate system).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the present disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97) to confirm the absolute configuration.

The solvent used in the present disclosure is commercially available.

LIST OF ABBREVIATIONS

| Boc | tert-butoxycarbonyl |
|---|---|
| DMSO | dimethyl sulfoxide |
| EDTA | ethylenediaminetetraacetic acid disodium salt |
| Et | ethyl |
| ELISA | enzyme-linked immunosorbent assay |
| ERα | estrogen receptor α |
| $IC_{50}$ | half inhibition concentration |
| μg | microgram |
| μL | microliter |
| μM | micromole per liter |
| mL | milliliter |
| mM | millimole per liter |
| ng | nanogram |
| nM | nanomole per liter |
| PBS | phosphate buffered saline |
| pg | picogram |
| p-HPLC | preparative high performance liquid chromatography for purification of compounds |
| TBS | tert-butyldimethylsilyl |
| Tf | trifluoromethanesulfonyl |
| THP | tetrahydro-2H-pyran-2-yl |
| TMB | 3,3',5,5'-tetramethylbenzidine |
| Triton X-100 | polyethylene glycol octylphenyl ether |

The compounds of the present disclosure are named manually or by ChemDraw® software, and the commercially available compounds use the supplier catalog names.

DETAILED DESCRIPTION OF THE PREFERRED EMBODIMENT

The present disclosure is described in detail by the embodiments below, but it does not mean that there are any adverse restrictions on the present disclosure. The present disclosure has been described in detail herein, wherein specific implementations thereof are also disclosed, and it will be apparent to those skilled in the art that various variations and improvements can be made to specific implementations of the present disclosure without departing from the spirit and scope of the present disclosure.

Those people skilled in the art should know that in order to prepare the compounds of the present disclosure, the order of the reaction steps in each reaction step may be different, which also belongs to the scope of the present disclosure.

Preparation of Intermediate Compound 1-13

Synthetic Route:

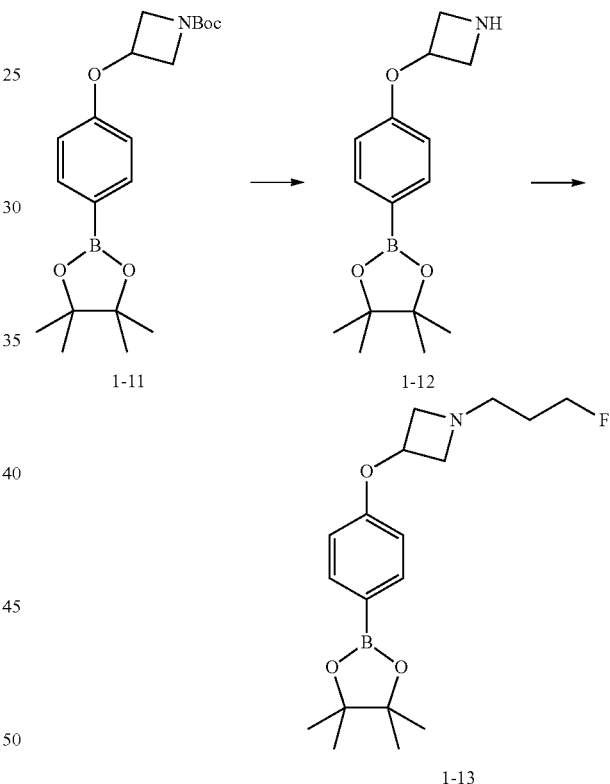

Step A: 1-11 (1.5 g, 4 mmol) was dissolved in dichloromethane (10 mL), and trifluoroacetic acid (3.08 g, 27 mmol) was added thereto, then the mixture was stirred at 25° C. for 0.5 hours, and concentrated under reduced pressure to obtain 1-12.

Step B: 1-12 (1.4 g, 3.6 mmol) and 1-fluoro-3-iodopropane (743.86 mg, 3.96 mmol) were dissolved in acetonitrile (20 mL), and then potassium carbonate (1.24 g, 8.99 mmol) was added thereto, and the mixture was stirred at 40° C. for 12 hours. To the reaction mixture were added water (50 mL) and ethyl acetate (50 mL), the organic layer was separated and the aqueous phase was extracted with 60 mL of ethyl acetate (30 mL×2). The combined organic phases were washed with saturated brine (30 mL), dried over anhydrous sodium sulfate, filtered and then concentrated under reduced pressure to obtain a crude product. The crude product was purified by p-HPLC (separation column: Welch Ultimate XB-SiOH (specification: 250 mm×50 mm, particle size: 10 m); mobile phase: [n-hexane-ethanol (1% ammonia water)]; elution gradient: 1%-30%, 8 min) to obtain compound 1-13. $^1$H NMR (400 MHz, DMSO-$d_6$) δ=7.58 (d, J=8.6 Hz, 2H), 6.81 (d, J=8.6 Hz, 2H), 4.79 (t, J=5.6 Hz, 1H), 4.50 (s, 1H), 4.39 (s, 1H), 3.71 (dd, J=6.1, 8.3 Hz, 2H), 2.99-2.88 (m, 2H), 2.53-2.50 (m, 2H), 1.75-1.54 (m, 2H), 1.26 (s, 12H). LCMS (ESI) m/z: 336.5 [M+H]$^+$.

Preparation of Intermediate Compound 2-10

Synthetic Route:

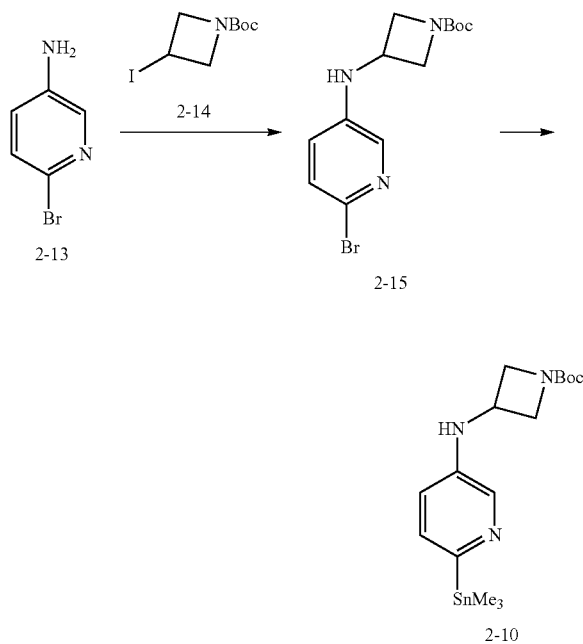

Step A: Cesium carbonate (50.46 g, 154.88 mmol) and 2-14 (38 g, 134.23 mmol) were added to a solution of 2-13 (17.86 g, 103.25 mmol) in N,N-dimethylformamide (150 mL), and the mixture was stirred at 100° C. for 16 hours. The reaction solution was diluted with water (500 mL) and extracted with ethyl acetate (100 mL×2). The combined organic phases were washed with saturated brine (200 mL×2), dried over anhydrous sodium sulfate, filtered and then concentrated under reduced pressure to obtain a crude product, and the crude product was purified by preparative HPLC (separation column: Phenomenex luna C18 (specification: 250 mm×70 mm, particle size: 10 m); mobile phase: [water (0.225% formic acid)-acetonitrile]; elution gradient: 35%-65%, 25 min) to obtain 2-15. LCMS (ESI) m/z: 328.1 [M+H]$^+$ Step B: A solution of 2-15 (200 mg, 595.77 µmol), hexamethyldistannane (260 mg, 793.59 µmol), lithium chloride (30.31 mg, 714.92 µmol), and tetrakis(triphenylphosphine)palladium (0) (68.84 mg, 59.58 µmol) in toluene (3 mL) was stirred at 90° C. for 3 hours under nitrogen atmosphere to obtain 2-10 (the reaction solution was directly used in the next step without work-up).

Preparation of Intermediate Compound 3-4

Synthetic Route:

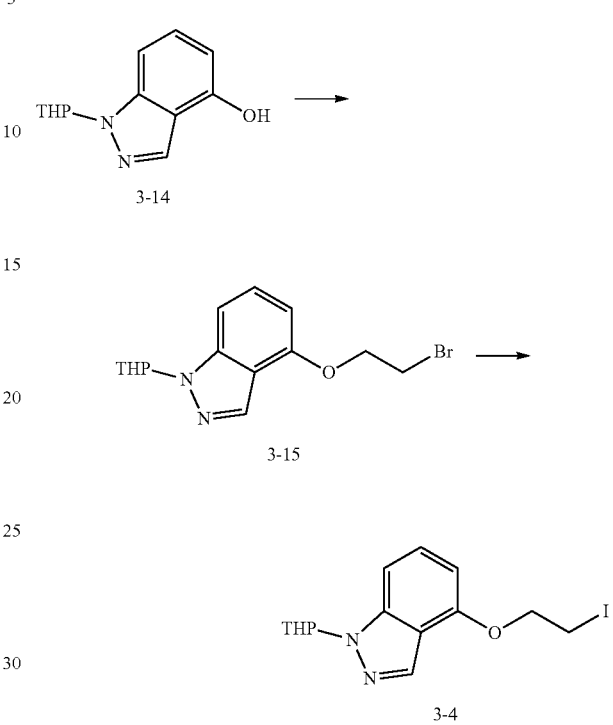

Step A: A mixture of 3-14 (29 g, 132.87 mmol), potassium carbonate (55.09 g, 398.62 mmol), 1,2-dibromoethane (124.81 g, 664.37 mmol) and acetonitrile (300 mL) was stirred and reacted at 65° C. for 12 hours, then filtered, and the obtained filtrate was concentrated under reduced pressure to remove the solvent acetonitrile. The residue was added with saturated sodium bicarbonate (150 mL), and extracted with ethyl acetate (200 mL×2), and then the combined organic phases were washed with saturated brine (150 mL×2), dried over anhydrous sodium sulfate, filtered and then concentrated under reduced pressure to obtain a crude product. The crude product was purified by column chromatography (eluent: petroleum ether/ethyl acetate=50/1 to 10/1) to obtain compound 3-15. LCMS (ESI) m/z: 326.8 [M+H]$^+$.

Step B: A mixture of 3-15 (25 g, 76.88 mmol), sodium iodide (23.05 g, 153.75 mmol) and acetone (250 mL) was stirred and reacted at 25° C. for 18 hours, then filtered, and the obtained filtrate was concentrated under reduced pressure to remove the solvent acetone. The residue was added with water (100 mL), and extracted with ethyl acetate (100 mL×2), and then the combined organic phases were washed with saturated brine (100 mL×2), dried over anhydrous sodium sulfate, filtered and then concentrated under reduced pressure to obtain compound 3-4.

Compound 3-4: $^1$H NMR (400 MHz, CDCl$_3$) δ=8.04 (s, 1H), 7.22-7.17 (m, 1H), 7.15-7.08 (m, 1H), 6.40 (d, J=7.58 Hz, 1H), 5.61 (dd, J=2.69, 9.41 Hz, 1H), 4.43-4.21 (m, 2H), 4.03-3.89 (m, 1H), 3.74-3.56 (m, 1H), 3.43 (t, J=6.97 Hz, 2H), 2.61-2.36 (m, 1H), 2.17-1.92 (m, 2H), 1.81-1.58 (m, 3H).

Preparation of Intermediate Compound 3-11

Synthetic Route:

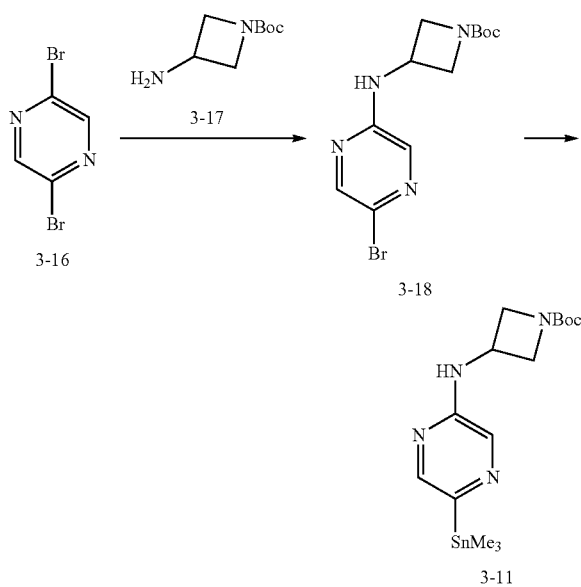

Step A: N,N-Diisopropylethanamine (1.92 g, 14.88 mmol) was added to a solution of 3-16 (1.18 g, 4.96 mmol) and 3-17 (1.71 g, 9.92 mmol) in dimethyl sulfoxide (12 mL), and the mixture was stirred at 130° C. for 12 hours. The reaction solution was diluted with water (200 mL) and extracted with ethyl acetate (200 mL). The combined organic phases were washed with water (100 mL×2) and saturated brine (100 mL) in turn, dried over anhydrous sodium sulfate, filtered and then concentrated under reduced pressure to obtain a crude product. The crude product was purified by column chromatography (eluent: petroleum ether/ethyl acetate=8/1 to 2/1) to obtain 3-18. LCMS (ESI) m/z: 329.1 [M+H]$^+$.

Step B: A solution of 3-18 (400 mg, 1.22 mmol), hexamethyldistannane (477.72 mg, 1.46 mmol), lithium chloride (154.54 mg, 3.65 mmol), and tetrakis(triphenylphosphine) palladium (0) (140.41 mg, 121.51 μmol) in toluene (4 mL) was stirred at 90° C. for 3 hours under nitrogen atmosphere to obtain 3-11 (the reaction solution was directly used in the next step without work-up.)

Preparation of Intermediate Compound 4-6

Synthetic Route:

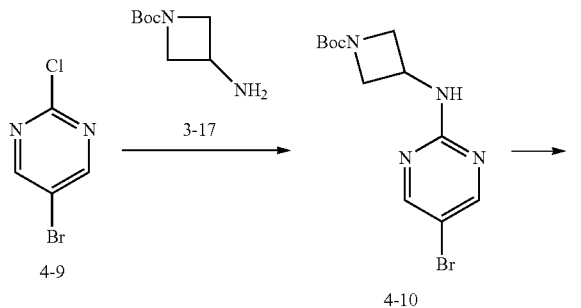

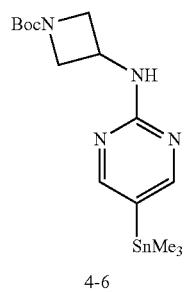

Step A: A solution of 4-9 (500 mg, 2.58 mmol), 3-17 (489.17 mg, 2.84 mmol), and N,N-diisopropylethanamine (668.17 mg, 5.17 mmol) in isopropanol (10 mL) was stirred at 90° C. for 12 hours under nitrogen atmosphere. The reaction solution was added with water (30 mL) and ethyl acetate (30 mL). After the phases were separated, the obtained organic phase was washed with saturated brine (10 mL×3), dried over anhydrous sodium sulfate, filtered and then concentrated under reduced pressure to obtain 4-10.

Step B: A solution of 4-10 (200 mg, 607.55 μmol), hexamethyldistannane (670 mg, 2.059 mmol), lithium chloride (77.27 mg, 1.82 mmol) and tetrakis(triphenylphosphine)palladium (0) (70.21 mg, 60.75 μmol) in toluene (3 mL) was stirred at 90° C. for 3 hours under nitrogen atmosphere to obtain 4-6 (the reaction solution was directly used in the next step without work-up).

Preparation of Intermediate Compound 7-1

Synthetic Route:

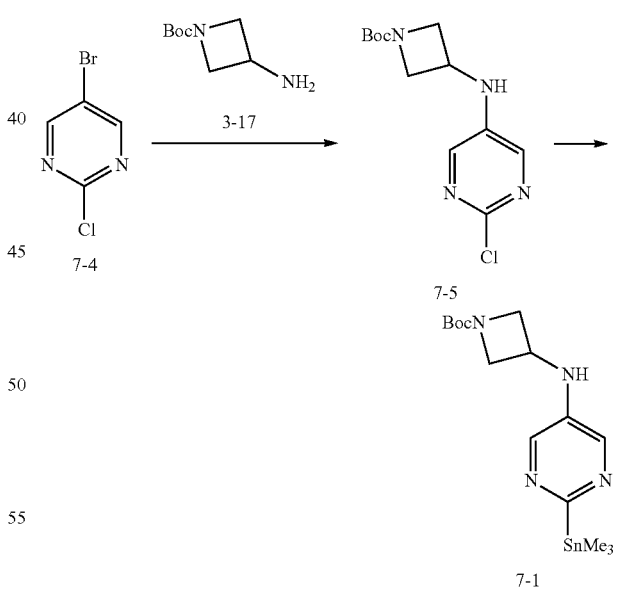

Step A: A solution of 7-4 (4.49 mg, 23.23 mmol), 3-17 (2.00 g, 11.61 mmol), potassium carbonate (4.81 g, 34.84 mmol), 4,5-bis(diphenylphosphino)-9,9-dimethylxanthene (2.69 g, 4.65 mmol) and tris(dibenzylideneacetone)dipalladium(0) (2.13 g, 2.32 mmol) in toluene (60 mL) was stirred under nitrogen atmosphere at 100° C. for 18 hours. The obtained reaction solution was cooled to room temperature, poured into water (50 mL), and extracted with ethyl acetate (50 mL×2). The combined organic phases were dried over anhydrous sodium sulfate, filtered and then concentrated under reduced pressure to obtain a crude product. The crude product was purified by reverse phase column chromatography to obtain compound 7-5. LCMS (ESI) m/z: 601.2 [M+H]⁺.

Step B: A solution of 7-5 (300 mg, 1.05 mmol), hexamethyldistannane (518 mg, 1.58 mmol), lithium chloride (133.98 mg, 3.16 mmol) and tetrakis(triphenylphosphine) palladium (0) (121.75 mg, 105.36 μmol) in toluene (6 mL) was stirred at 90° C. for 24 hours under nitrogen atmosphere to obtain 7-1 (the reaction solution was directly used in the next step without work-up).

Preparation of Intermediate Compound 9-2

Synthetic Route:

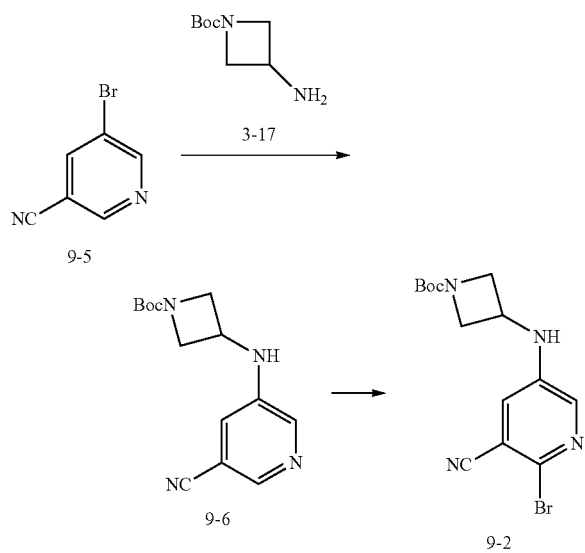

Step A: Cuprous iodide(I) (2.04 g, 10.71 mmol), DL-proline (2.47 g, 21.42 mmol) and potassium carbonate (22.20 g, 160.62 mmol) were added to a solution of 9-5 (9.8 g, 53.55 mmol) and 3-17(18.45 g, 107.10 mmol) in dimethyl sulfoxide (100 mL). The reaction was stirred at 120° C. for 12 hours under nitrogen atmosphere. The obtained reaction solution was added with water (100 mL) and extracted with ethyl acetate (100 mL×3). The combined organic phases were washed with saturated brine (100 mL×2), dried over anhydrous sodium sulfate, filtered and then concentrated under reduced pressure to obtain a crude product. The crude product was purified by column chromatography (eluent: petroleum ether/ethyl acetate=100/1 to 1/1) to obtain compound 9-6. LCMS (ESI) m/z: 219.2 [M+H]⁺.

Step B: N-Bromosuccinimide (1.95 g, 10.94 mmol) was added to a solution of 9-6 (2.5 g, 9.11 mmol) in N,N-dimethylformamide (30 mL). The reaction was stirred at 20° C. for 12 hours under nitrogen atmosphere. The obtained reaction solution was quenched with sodium sulfite (30 mL) and extracted with ethyl acetate (50 mL×3). The combined organic phases were washed with saturated brine (50 mL×2), dried over anhydrous sodium sulfate, filtered and then concentrated under reduced pressure to obtain a crude product. The crude product was purified by column chromatography (eluent: petroleum ether/ethyl acetate=100/1 to 1/1) to obtain compound 9-2. LCMS (ESI) m/z: 353.21 [M+H]⁺.

Preparation of Intermediate Compound 10-1

Synthetic Route:

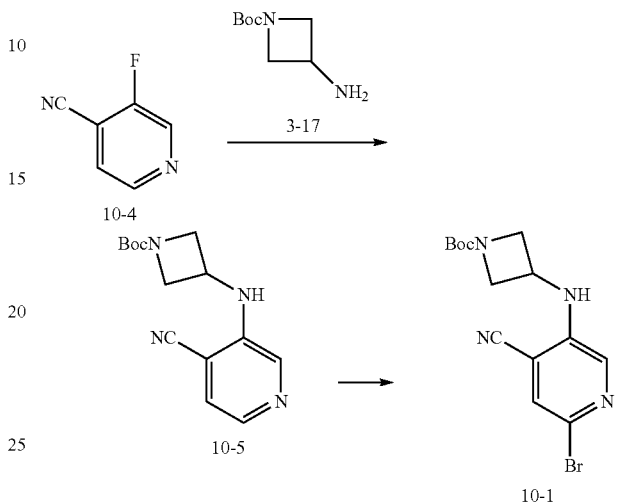

Step A: N,N-Diisopropylethanamine (3.81 g, 29.48 mmol) was added to a solution of 10-4 (1.20 g, 9.83 mmol) and 3-17 (1.69 g, 9.83 mmol) in N-methylpyrrolidone (10 mL), and the mixture was heated to 120° C. and stirred for 1 hour under microwave irradiation. The reaction solution was added with water (20 mL) and extracted with ethyl acetate (20 mL×2). The organic phases were washed with saturated brine (30 mL), dried over anhydrous sodium sulfate, filtered and then concentrated under reduced pressure to obtain compound 10-5.

Step B: N-Bromosuccinimide (1.62 g, 9.11 mmol) was added to a solution of 10-5 (2.5 g, 9.11 mmol) in N,N-dimethylformamide (20 mL). The reaction was stirred at 5 to 15° C. for 12 hours under nitrogen atmosphere. The obtained reaction solution was added with water (40 mL) and extracted with ethyl acetate (30 mL×2). The combined organic phases were washed with saturated brine (30 mL), dried over anhydrous sodium sulfate, filtered and then concentrated under reduced pressure to obtain a crude product. The crude product was purified by column chromatography (eluent: petroleum ether/ethyl acetate=10/1 to 2/1) to obtain compound 10-1. LCMS (ESI) m/z: 296.9/298.6 [M+H]⁺.

Preparation of Intermediate Compound 11-1

Synthetic Route:

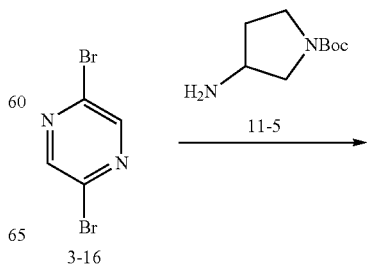

27

-continued

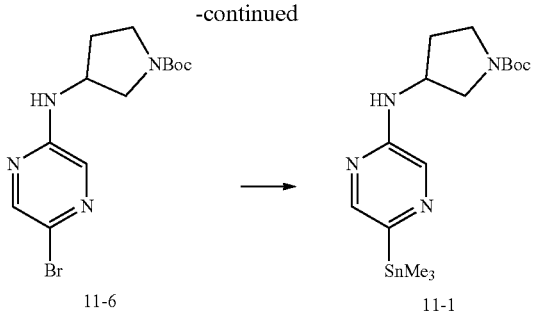

Step A: Triethylamine (3.83 g, 37.83 mmol) was added to a solution of 3-16 (3.0 g, 12.61 mmol) and 11-5 (2.35 g, 12.61 mmol) in dimethyl sulfoxide (10 mL), and the mixture was stirred at 130° C. for 16 hours. The reaction solution was extracted with ethyl acetate (300 mL×1). The organic phase was washed with saturated brine (100 mL×4), dried over anhydrous sodium sulfate, filtered and then concentrated under reduced pressure to obtain a crude product. The crude product was purified by preparative HPLC (separation column: Phenomenex luna C18, specification: 250 mm×70 mm, particle size: 10 m); mobile phase: [water (0.225% formic acid)-acetonitrile]; elution gradient: 35%-65%, 20 min) to obtain compound 11-6. LCMS (ESI) m/z: 287/289 [M-55]$^+$.

28

Step B: A solution of 11-6 (800 mg, 2.33 mmol), hexamethyldistannane (1.160 mg, 3.54 mmol), lithium chloride (118.57 mg, 2.80 mmol), and tetrakis(triphenylphosphine) palladium (0) (269.35 mg, 233.09 μmol) in toluene (10 mL) was stirred at 90° C. for 3 hours under nitrogen atmosphere to obtain 11-1 (the reaction solution was directly used in the next step without work-up.)

Embodiment 1

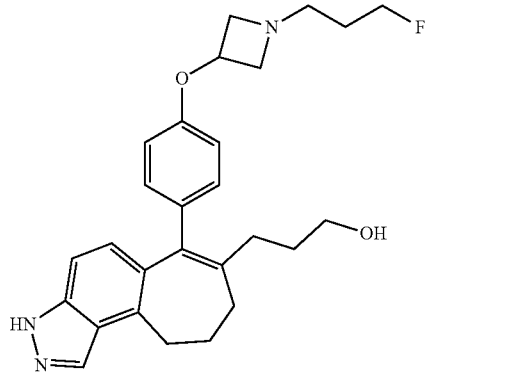

Synthetic Route:

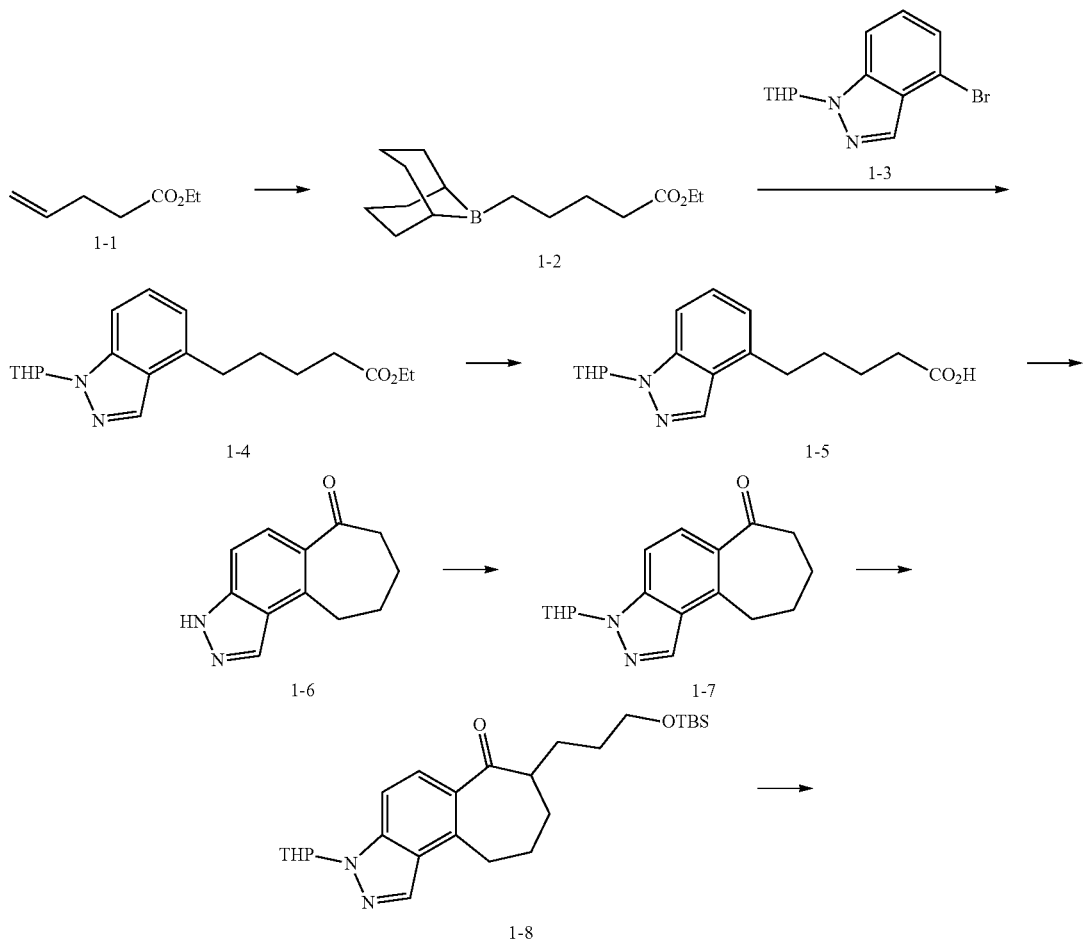

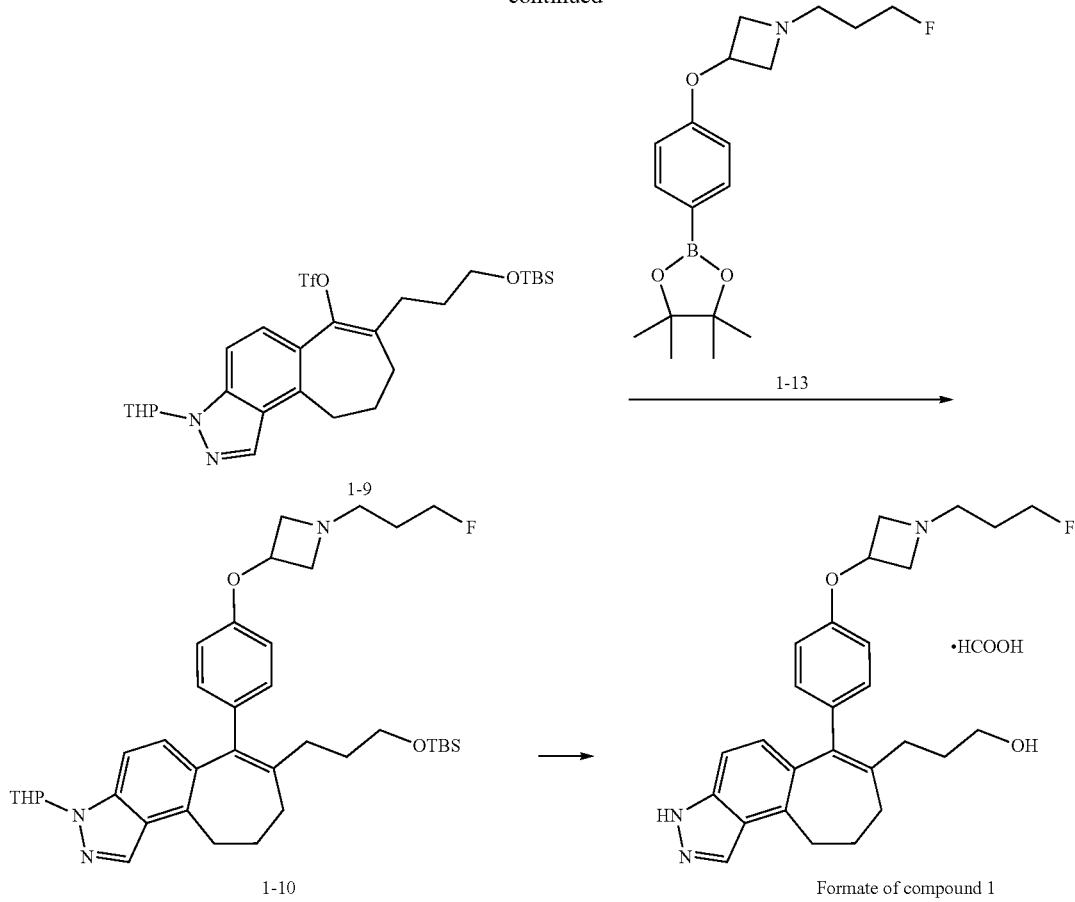

Step A: 1-1 (7 g, 54.62 mmol) was dissolved in tetrahydrofuran (10 mL), and 9-borabicyclo[3.3.1]nonane (0.5 mol/L, 109 mL) was added thereto under nitrogen atmosphere. The mixture was stirred at 60° C. for 3 hours to obtain a reaction solution of 1-2 in tetrahydrofuran, which was directly used in the next step.

Step B: The solution of 1-2 in tetrahydrofuran obtained in step A and 1-3 (10 g, 35.57 mmol) were added to a mixture of tetrahydrofuran (10 mL) and water (25 mL), and then tetrakis(triphenylphosphine)palladium(0) (2.06 g, 1.78 mmol) and potassium phosphate (11.32 g, 53.35 mmol) were added thereto. The mixture was stirred at 70° C. for 12 hours under nitrogen atmosphere. The obtained reaction solution was added with water (50 mL) and extracted with 150 mL of ethyl acetate (50 mL×3). The combined organic phases were washed with saturated brine (20 mL), dried over anhydrous sodium sulfate, filtered and then concentrated under reduced pressure to obtain a crude product. The crude product was purified by column chromatography (eluent: petroleum ether/ethyl acetate=20/1 to 7/1) to obtain compound 1-4. LCMS (ESI) m/z: 331.1 [M+H]$^+$.

Step C: 1-4 (10.2 g, 30.87 mmol) was dissolved in methanol (60 mL), and an aqueous solution (20 mL) of sodium hydroxide (2.47 g, 61.74 mmol) was added thereto, and the mixture was stirred at 15 to 25° C. for 2 hours. The obtained reaction solution was added with hydrochloric acid (1 mol/L, 80 mL) and extracted with 150 mL of ethyl acetate (50 mL×3). The combined organic phases were washed with saturated brine (20 mL), dried over anhydrous sodium sulfate, filtered and then concentrated under reduced pressure to obtain compound 1-5.

Compound 1-5: $^1$H NMR (400 MHz, CDCl$_3$) δ=8.08 (d, J=0.6 Hz, 1H), 7.43 (d, J=8.4 Hz, 1H), 7.36-7.27 (m, 1H), 6.96 (d, J=7.0 Hz, 1H), 5.78-5.66 (m, 1H), 4.09-4.00 (m, 1H), 3.81-3.69 (m, 1H), 2.95 (t, J=7.4 Hz, 2H), 2.66-2.51 (m, 1H), 2.38 (t, J=7.2 Hz, 2H), 2.21-2.11 (m, 1H), 1.85-1.62 (m, 8H). LCMS (ESI) m/z: 303.2 [M+H]$^+$.

Step D: 1-5 (9.5 g, 31.42 mmol) was dissolved in polyphosphoric acid (200 g), and the mixture was stirred at 100° C. for 12 hours under nitrogen atmosphere. The obtained reaction solution was poured into water (1000 mL) and extracted with 600 mL of ethyl acetate (200 mL×3). The combined organic phases were washed with saturated brine (200 mL), dried over anhydrous sodium sulfate, filtered and then concentrated under reduced pressure to obtain compound 1-6. LCMS (ESI) m/z: 201.1 [M+H]$^+$.

Step E: 1-6 (4.5 g, 22.47 mmol) was dissolved in dichloromethane (45 mL), and then p-toluenesulfonic acid monohydrate (85.5 mg, 449.47 μmol) and 3,4-dihydropyran (2.84 g, 33.71 mmol) were added thereto. The mixture was stirred at 20 to 30° C. for 12 hours under nitrogen atmosphere. The obtained reaction solution was added with saturated sodium bicarbonate aqueous solution (50 mL) and extracted with 90 mL of dichloromethane (30 mL×3). The combined organic phases were washed with saturated brine (50 mL), dried over anhydrous sodium sulfate, filtered and then concentrated under reduced pressure to obtain a crude product. The crude product was purified by column chromatography (eluent:

petroleum ether/ethyl acetate=10/1 to 4/1) to obtain compound 1-7. LCMS (ESI) m/z: 285.1 [M+H]$^+$.

Step F: 1-7 (1 g, 3.52 mmol) and (3-bromo-n-propoxy)(tert-butyl)dimethylsilane (1.34 g, 5.28 mmol) were dissolved in THF (15 mL), and then potassium tert-butoxide (591.94 mg, 5.28 mmol) and tetra(n-butyl)ammonium iodide (1.30 g, 3.52 mmol) were added thereto. The mixture was stirred at 70° C. for 12 hours under nitrogen atmosphere. The obtained reaction solution was added with water (20 mL) and extracted with 40 mL of ethyl acetate (20 mL×2). The combined organic phases were washed with saturated brine (20 mL), dried over anhydrous sodium sulfate, filtered and then concentrated under reduced pressure to obtain a crude product. The crude product was purified by column chromatography (eluent: petroleum ether/ethyl acetate=20/1 to 7/1) to obtain compound 1-8. LCMS (ESI) m/z: 457.2 [M+H]$^+$.

Step G: 1-8 (0.1 g, 218.97 μmol) was dissolved in tetrahydrofuran (6 mL), and a solution of potassium bis(trimethylsilyl)amide in tetrahydrofuran (1 mol/L, 328 μL, 328 μmol) was added thereto under nitrogen atmosphere. The mixture was stirred at −78° C. for 0.5 hours, and then a solution of N-phenyl-bis(trifluoromethanesulfonyl) imide (117.34 mg, 328 μmol) in tetrahydrofuran (2 mL) was added, and the mixture was stirred at 20 to 30° C. for 12 hours. The obtained reaction solution was added with water (20 mL) and extracted with 40 mL of ethyl acetate (20 mL×2). The combined organic phases were washed with saturated brine (20 mL), dried over anhydrous sodium sulfate, filtered and then concentrated under reduced pressure to obtain a crude product. The crude product was purified by thin-layer silica gel chromatography (eluent: petroleum ether/ethyl acetate=5/1) to obtain compound 1-9. LCMS (ESI) m/z: 589.2 [M+H]$^+$.

Step H: 1-9 (50 mg, 84.93 μmol) and 1-13 (42.71 mg, 127.4 μmol) were dissolved in a mixture of 1,4-dioxane (2 mL) and water (0.4 mL), and [1,1'-bis(diphenylphosphino)ferrocene]palladium(II) dichloride (19.76 mg, 24.20 μmol) (6.21 mg, 8.49 μmol) and cesium carbonate (55.34 mg, 169.86 μmol) were added thereto. The mixture was stirred at 50° C. for 1 hour under nitrogen atmosphere. The obtained reaction solution was added with water (20 mL) and extracted with 40 mL of ethyl acetate (20 mL×2). The combined organic phases were washed with saturated brine (20 mL), dried over anhydrous sodium sulfate, filtered and then concentrated under reduced pressure to obtain a crude product. The crude product was purified by thin-layer silica gel chromatography (eluent: petroleum ether/ethyl acetate=1/4) to obtain compound 1-10. LCMS (ESI) m/z: 648.4 [M+H]$^+$.

Step I: 1-10 (10 mg, 15.43 μmol) was dissolved in dichloromethane (2 mL) and trifluoroacetic acid (1 mL) was added thereto. The mixture was stirred at 25 to 30° C. for 4 hours under nitrogen atmosphere. The obtained reaction solution was added with saturated sodium carbonate aqueous solution (20 mL) and extracted with 60 mL of dichloromethane (20 mL×3). The combined organic phases were washed with saturated brine (20 mL), dried over anhydrous sodium sulfate, filtered and then concentrated under reduced pressure to obtain a crude product. The crude product was purified by p-HPLC (separation column: Shim-pack C18 (specification: 150 mm×25 mm, particle size: 10 m); mobile phase: [water (0.225% formic acid) acetonitrile]; elution gradient: 17%37%, 10 min) to obtain the formate of compound 1.

The formate of compound 1: $^1$H NMR (400 MHz, DMSO-d$_6$) δ=13.07-12.77 (m, 1H), 8.27-8.04 (m, 2H), 7.20 (d, J=8.8 Hz, 1H), 6.96 (br d, J=8.4 Hz, 2H), 6.77 (br d, J=8.4 Hz, 2H), 6.63 (d, J=8.5 Hz, 1H), 4.81-4.73 (m, 1H), 4.51 (br t, J=6.0 Hz, 1H), 4.40 (br t, J=6.0 Hz, 1H), 3.74 (br t, J=6.7 Hz, 2H), 3.34 (br s, 2H), 2.97 (br d, J=6.5 Hz, 4H), 2.53 (br s, 2H), 2.31-2.17 (m, 4H), 1.91 (br t, J=6.6 Hz, 2H), 1.72-1.59 (m, 4H). LCMS (ESI) m/z: 450.1 [M+H]$^+$.

Embodiment 2

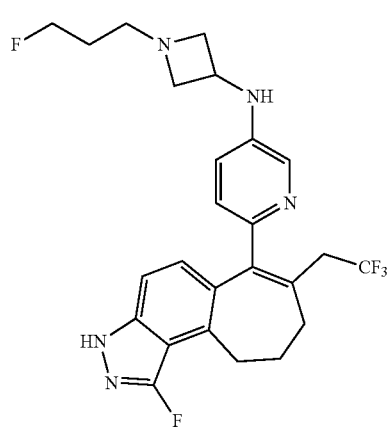

2

Synthetic Route:

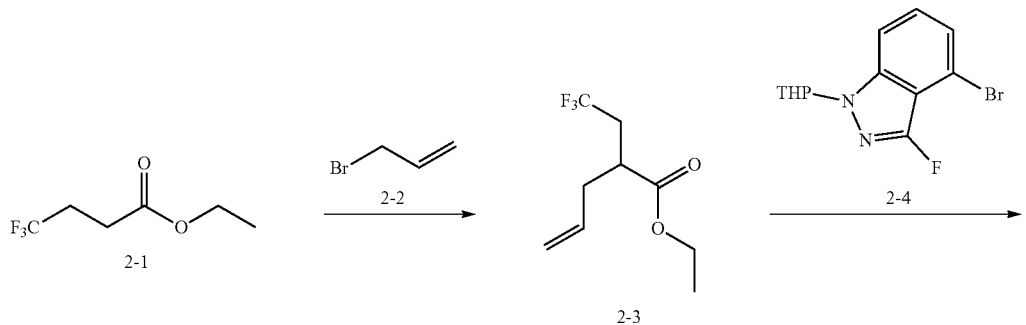

-continued
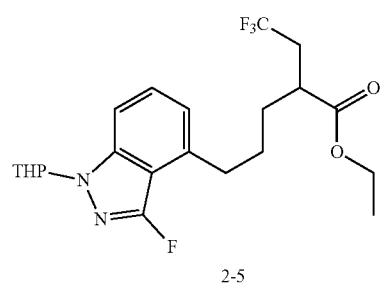
2-5
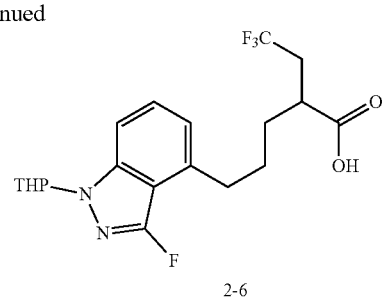
2-6
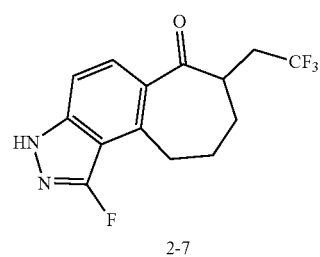
2-7
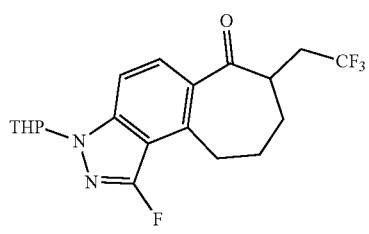
2-8
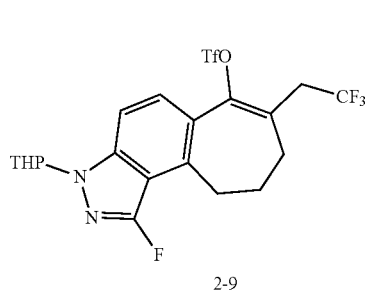
2-9
2-10
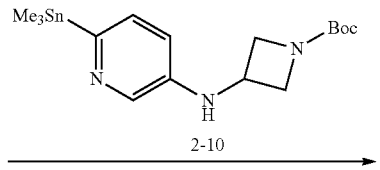
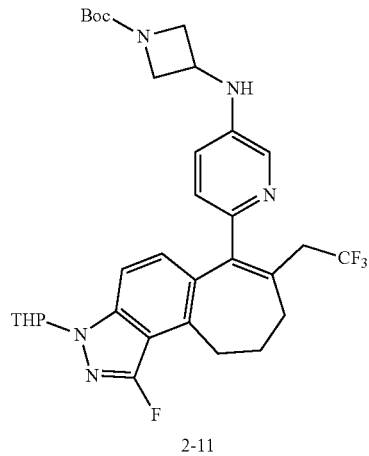
2-11
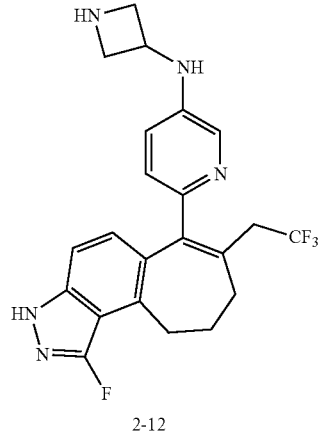
2-12
2-13

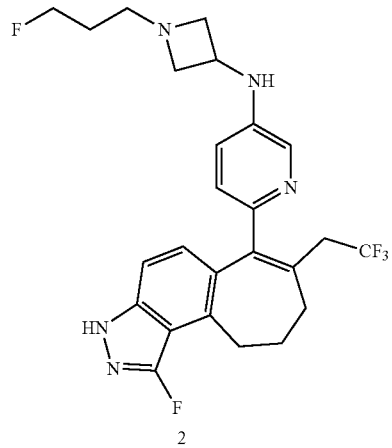

2

Step A: A solution of n-butyl lithium in n-hexane (2.5 mol/L, 28.21 mL) was slowly dropwise added to a solution of N,N-diisopropylamine (7.73 g, 76.41 mmol) in tetrahydrofuran (100 mL) under nitrogen atmosphere at 0° C., and the reaction solution was stirred at 0° C. for 0.5 hours and then cooled to −70° C., and then a solution of 2-1 (10 g, 58.78 mmol) in tetrahydrofuran (100 mL) was slowly added dropwise. The reaction solution was stirred at −70° C. for 0.5 hours after the dropwise addition was completed, and a solution of 2-2 (8.53 g, 70.53 mmol) in tetrahydrofuran (10 mL) was slowly added dropwise thereto, then the reaction solution was stirred at −70° C. for 3 hours after the dropwise addition was completed. The reaction solution was added with saturated ammonium chloride aqueous solution (200 mL), and extracted with ethyl acetate (100 mL×2), and then the combined organic phases were washed with saturated ammonium chloride aqueous solution (200 mL×2) and saturated brine (200 mL×2), dried over anhydrous sodium sulfate, filtered and then concentrated under reduced pressure to obtain a crude product. The crude product was purified by column chromatography (eluent: petroleum ether) to obtain compound 2-3.

Compound 2-3: $^1$HNMR (400 MHz, CDCl$_3$) δ=5.82-5.59 (m, 1H), 5.15 (d, J=1.0 Hz, 1H), 5.13-5.09 (m, 1H), 4.19 (q, J=7.1 Hz, 2H), 2.82-2.74 (m, 1H), 2.69-2.53 (m, 1H), 2.50-2.40 (m, 1H), 2.39-2.30 (m, 1H), 2.30-2.17 (m, 1H), 1.32-1.27 (m, 3H).

Step B: 9-Borabicyclo[3.3.1]nonane (0.5 mol/L, 32.45 mL) was added to a solution of 2-3 (3.1 g, 14.75 mmol) in tetrahydrofuran (18 mL) under nitrogen atmosphere at 20° C., and the reaction solution was stirred at 60° C. for 3 hours and then cooled to room temperature. Water (10 mL), 2-4 (3.53 g, 11.80 mmol), tetrakis(triphenylphosphine) palladium (0) (1.7 g, 1.47 mmol) and potassium phosphate (4.7 g, 22.12 mmol) were added thereto in turn. The mixture was stirred at 70° C. for 16 hours under nitrogen atmosphere. The obtained reaction solution was diluted with ethyl acetate (100 mL) and washed with saturated brine (200 mL×2), dried over anhydrous sodium sulfate, filtered and then concentrated under reduced pressure to obtain a crude product. The crude product was purified by column chromatography (eluent: petroleum ether/ethyl acetate=100/1 to 0/1) to obtain compound 2-5. LCMS (ESI) m/z: 431.1 [M+H]$^+$.

Step C: Sodium hydroxide (2.15 g, 53.83 mmol) was added to a mixed solution of 2-5 (6.7 g, 13.46 mmol) in methanol (75 mL) and water (25 mL), and the mixture was stirred at 25° C. for 16 hours. The obtained reaction solution was concentrated under reduced pressure to remove the solvent methanol, and the residue was diluted with water (150 mL) and extracted with dichloromethane (100 mL×2), and the pH of aqueous phase was adjusted to 2 by adding with hydrochloric acid (2 mol/L) and then the mixture was extracted with ethyl acetate (80 mL×4). The combined organic phases were washed with saturated brine (200 mL×2), dried over anhydrous an hydrous sodium sulfate, filtered and concentrated under reduced pressure to obtain compound 2-6.

Compound 2-6: $^1$HNMR (400 MHz, CDCl$_3$) δ=7.34 (d, J=4.3 Hz, 2H), 6.99-6.90 (m, 1H), 5.59 (td, J=2.4, 9.3 Hz, 1H), 4.04 (br d, J=11.0 Hz, 1H), 3.73 (dt, J=2.9, 10.9 Hz, 1H), 2.97 (br t, J=7.1 Hz, 2H), 2.82-2.72 (m, 1H), 2.72-2.56 (m, 1H), 2.56-2.42 (m, 1H), 2.28-2.13 (m, 2H), 2.06-1.99 (m, 1H), 1.79-1.58 (m, 7H). LCMS (ESI) m/z: 403.1 [M+H]$^+$.

Step D: 2-6 (2.7 g, 6.54 mmol) was dissolved in polyphosphoric acid (30 mL), and the mixture was stirred at 110° C. for 16 hours. The obtained reaction solution was diluted with water (300 mL) and extracted with ethyl acetate (100 mL×3). The combined organic phases were washed with saturated sodium carbonate aqueous solution (200 mL×2) and saturated brine (200 mL), dried over anhydrous sodium sulfate, filtered and then concentrated under reduced pressure to obtain compound 2-7. LCMS (ESI) m/z: 301.1 [M+H]$^+$.

Step E: 2-7 (2.7 g, 8.99 mmol) was dissolved in dichloromethane (50 mL), and then p-toluenesulfonic acid monohydrate (855.26 mg, 4.5 mmol) and 3,4-dihydropyran (1.13 g, 13.49 mmol) were added thereto. The mixture was stirred at 25° C. for 16 hours. The reaction solution was concentrated under reduced pressure to obtain a crude product. The crude product was purified by column chromatography (eluent: petroleum ether/ethyl acetate=40/1 to 20/1) to obtain compound 2-8.

Compound 2-8: $^1$HNMR (400 MHz, CDCl$_3$) δ=7.81 (dd, J=5.4, 8.9 Hz, 1H), 7.38 (td, J=2.0, 8.8 Hz, 1H), 5.59 (td, J=2.4, 9.2 Hz, 1H), 4.06-3.95 (m, 1H), 3.81-3.64 (m, 2H), 3.36-3.23 (m, 1H), 3.22-2.95 (m, 2H), 2.53-2.38 (m, 1H), 2.35-2.20 (m, 2H), 2.19-2.08 (m, 2H), 2.06-2.00 (m, 1H), 1.80-1.65 (m, 5H). LCMS (ESI) m/z: 385.1 [M+H]$^+$.

Step F: A solution of 2-8 (200 mg, 473.79 μmol) in tetrahydrofuran (2 mL) was slowly added dropwise to a solution of potassium bis(trimethylsilyl)amide (1.0 mol/L, 709 μL) in tetrahydrofuran (5 mL) under nitrogen atmosphere at −70° C. The mixture was stirred at −70° C. for 1 hour, and then a solution of N-phenyl-bis(trifluoromethanesulfonyl) imide (253.54 mg, 709.70 μmol) in tetrahydrofuran (2 mL) was added, and the mixture was stirred at 20° C. for 16 hours. The obtained reaction solution was quenched with saturated ammonium chloride aqueous solution (50 mL) and extracted with ethyl acetate (30 mL×2). The combined organic phases were washed with saturated brine (50 mL), dried over anhydrous sodium sulfate, filtered and then concentrated under reduced pressure to obtain a crude product. The crude product was purified by thin-layer silica gel chromatography (eluent: petroleum ether/ethyl acetate=3/1) to obtain compound 2-9.

Compound 2-9: $^1$HNMR (400 MHz, CDCl$_3$) δ=7.51-7.37 (m, 2H), 5.60 (td, J=2.5, 9.2 Hz, 1H), 4.09-3.99 (m, 1H), 3.81-3.68 (m, 1H), 3.37-3.20 (m, 2H), 3.17-2.98 (m, 2H), 2.55-2.33 (m, 3H), 2.21-2.11 (m, 1H), 2.11-2.05 (m, 2H), 2.05-1.99 (m, 1H), 1.79-1.63 (m, 3H). LCMS (ESI) m/z: 517.0 [M+H]$^+$.

Step G: A solution of 2-9 (200 mg, 384.17 μmol), 2-10 (245 mg, 594.50 μmol), lithium chloride (48.86 mg, 1.15 mmol), and tetrakis(triphenylphosphine)palladium (0) (44.39 mg, 38.42 μmol) in toluene (7 mL) was stirred at 100° C. for 16 hours under nitrogen atmosphere. The obtained reaction solution was cooled and filtered, and the filtrate was diluted with ethyl acetate (40 mL) and washed with saturated brine (50 mL×3), dried over anhydrous sodium sulfate, filtered and then concentrated under reduced pressure to obtain a crude product. The crude product was purified by thin-layer silica gel chromatography (eluent: petroleum ether/ethyl acetate=1/1) to obtain compound 2-11.

Compound 2-11: $^1$HNMR (400 MHz, CDCl$_3$) δ=8.00 (d, J=2.8 Hz, 1H), 7.19 (dd, J=2.1, 8.8 Hz, 1H), 6.90 (d, J=8.9 Hz, 1H), 6.84-6.77 (m, 1H), 6.76-6.69 (m, 1H), 5.62-5.44 (m, 1H), 4.42-4.29 (m, 2H), 4.28-4.19 (m, 1H), 4.14-4.09 (m, 1H), 4.01 (br d, J=10.2 Hz, 1H), 3.79 (dd, J=4.5, 9.0 Hz, 2H), 3.75-3.61 (m, 1H), 3.46-3.27 (m, 2H), 3.07 (br t, J=7.0 Hz, 2H), 2.56-2.32 (m, 3H), 2.21-2.09 (m, 3H), 2.01 (br dd, J=3.4, 13.2 Hz, 1H), 1.81-1.67 (m, 2H), 1.66-1.62 (m, 1H), 1.51-1.39 (m, 9H). LCMS (ESI) m/z: 616.2 [M+H]$^+$.

Step H: 2-11 (160 mg, 258.15 μmol) was dissolved in dichloromethane (10 mL), and trifluoroacetic acid (2 mL) was added thereto. After the mixture was stirred at 25° C. for 4 hours, trifluoroacetic acid (1 mL) was further added thereto, and the reaction solution was further stirred at 25° C. for 1 hour. The obtained reaction solution was concentrated under reduced pressure to obtain a crude product of 2-12, and the crude product was used directly for the next step without purification.

Step I: N,N-Diisopropylethylamine (74.89 mg, 579.47 μmol) and 2-13 (32 mg, 170.23 mol) were added to a solution of 2-12 (50 mg, 115.89 μmol) in acetonitrile (5 mL), and the mixture was stirred at 25° C. for 16 hours. The reaction solution was diluted with ethyl acetate (50 mL) and washed with saturated sodium carbonate (50 mL×2) and saturated brine (50 mL×2), dried over anhydrous sodium sulfate, filtered and then concentrated under reduced pressure to obtain a crude product. The crude product was purified by preparative HPLC (separation column: Phenomenex Gemini-NX C18 (specification: 75 mm×30 mm, particle size: 3 m); mobile phase: [water (0.05% ammonia water)-acetonitrile]; elution gradient: 36%-66%, 7 min) to obtain compound 2.

Compound 2: $^1$HNMR (400 MHz, DMSO-d$_6$) δ=12.51 (s, 1H), 7.94 (d, J=2.8 Hz, 1H), 7.20 (dd, J=2.5, 8.8 Hz, 1H), 6.84 (dd, J=2.9, 8.5 Hz, 1H), 6.79-6.68 (m, 2H), 6.49 (br d, J=6.9 Hz, 1H), 4.53 (t, J=5.9 Hz, 1H), 4.42 (t, J=6.0 Hz, 1H), 4.11-3.96 (m, 1H), 3.77 (br s, 2H), 3.59-3.42 (m, 2H), 2.94 (br t, J=6.8 Hz, 3H), 2.59 (br d, J=3.0 Hz, 1H), 2.36-2.25 (m, 2H), 2.06-1.96 (m, 2H), 1.80-1.60 (m, 2H), 1.36-1.16 (m, 2H). LCMS (ESI) m/z: 492.2 [M+H]$^+$.

Embodiment 3

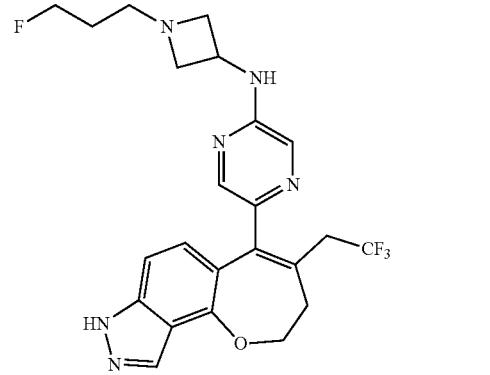

3

Synthetic Route:

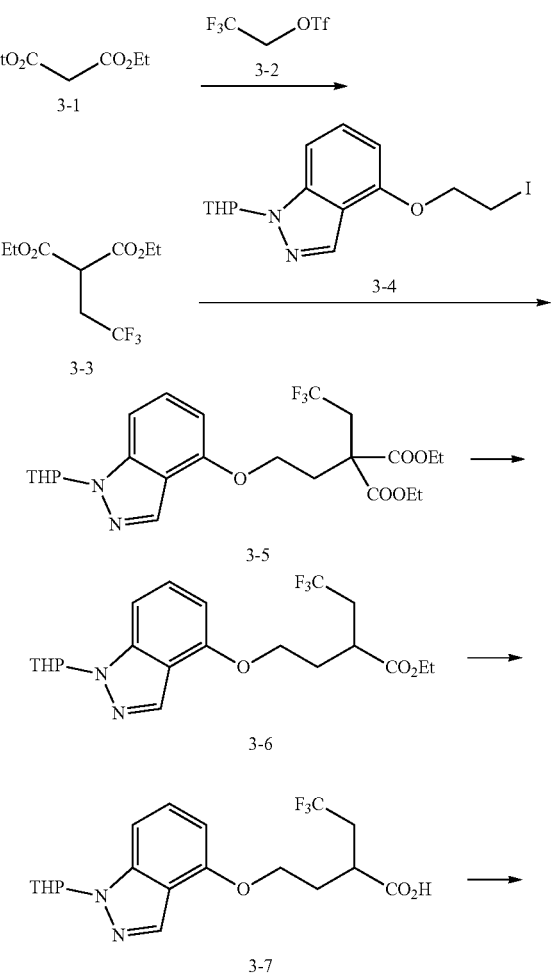

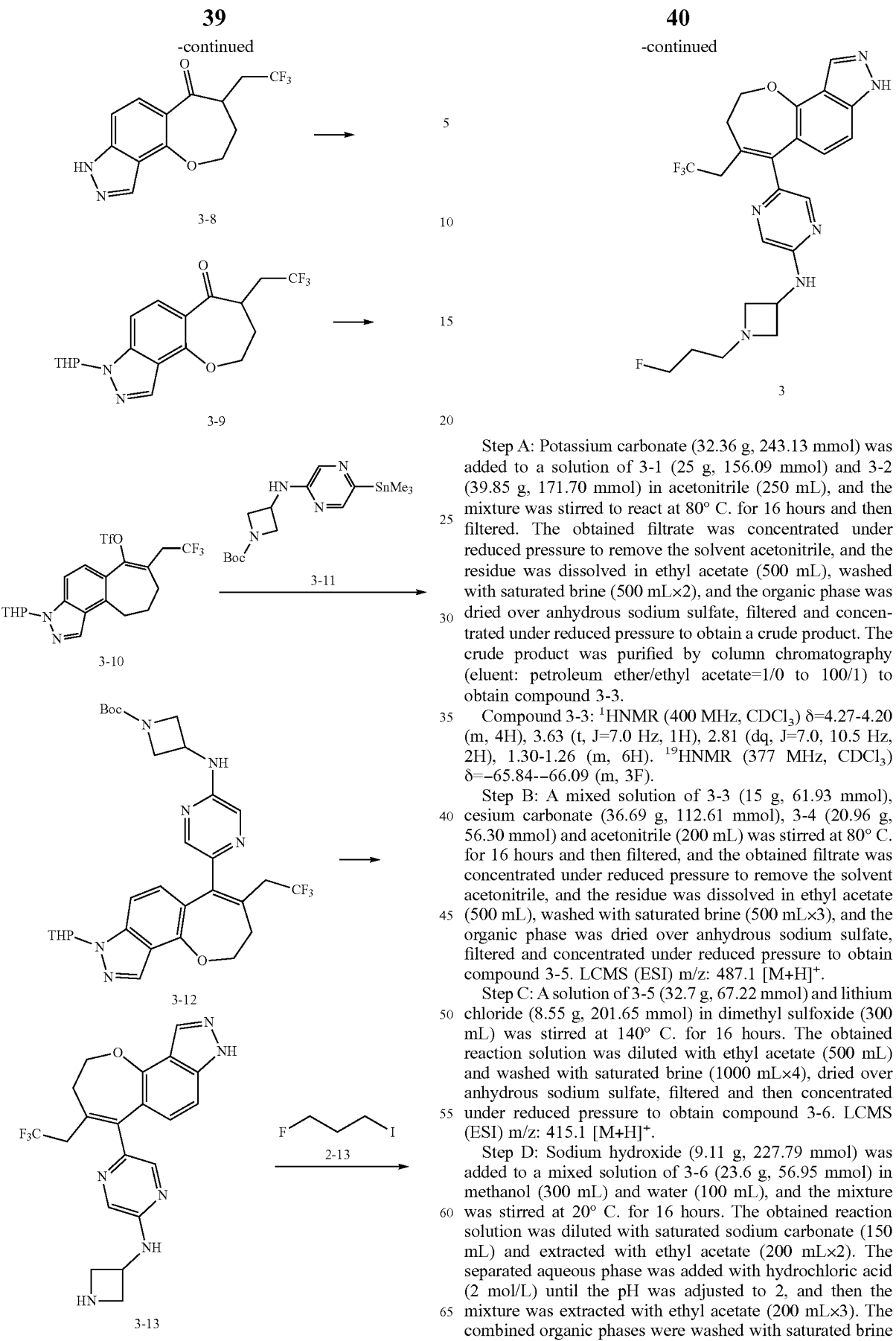

Step A: Potassium carbonate (32.36 g, 243.13 mmol) was added to a solution of 3-1 (25 g, 156.09 mmol) and 3-2 (39.85 g, 171.70 mmol) in acetonitrile (250 mL), and the mixture was stirred to react at 80° C. for 16 hours and then filtered. The obtained filtrate was concentrated under reduced pressure to remove the solvent acetonitrile, and the residue was dissolved in ethyl acetate (500 mL), washed with saturated brine (500 mL×2), and the organic phase was dried over anhydrous sodium sulfate, filtered and concentrated under reduced pressure to obtain a crude product. The crude product was purified by column chromatography (eluent: petroleum ether/ethyl acetate=1/0 to 100/1) to obtain compound 3-3.

Compound 3-3: $^1$HNMR (400 MHz, CDCl$_3$) δ=4.27-4.20 (m, 4H), 3.63 (t, J=7.0 Hz, 1H), 2.81 (dq, J=7.0, 10.5 Hz, 2H), 1.30-1.26 (m, 6H). $^{19}$HNMR (377 MHz, CDCl$_3$) δ=−65.84−−66.09 (m, 3F).

Step B: A mixed solution of 3-3 (15 g, 61.93 mmol), cesium carbonate (36.69 g, 112.61 mmol), 3-4 (20.96 g, 56.30 mmol) and acetonitrile (200 mL) was stirred at 80° C. for 16 hours and then filtered, and the obtained filtrate was concentrated under reduced pressure to remove the solvent acetonitrile, and the residue was dissolved in ethyl acetate (500 mL), washed with saturated brine (500 mL×3), and the organic phase was dried over anhydrous sodium sulfate, filtered and concentrated under reduced pressure to obtain compound 3-5. LCMS (ESI) m/z: 487.1 [M+H]$^+$.

Step C: A solution of 3-5 (32.7 g, 67.22 mmol) and lithium chloride (8.55 g, 201.65 mmol) in dimethyl sulfoxide (300 mL) was stirred at 140° C. for 16 hours. The obtained reaction solution was diluted with ethyl acetate (500 mL) and washed with saturated brine (1000 mL×4), dried over anhydrous sodium sulfate, filtered and then concentrated under reduced pressure to obtain compound 3-6. LCMS (ESI) m/z: 415.1 [M+H]$^+$.

Step D: Sodium hydroxide (9.11 g, 227.79 mmol) was added to a mixed solution of 3-6 (23.6 g, 56.95 mmol) in methanol (300 mL) and water (100 mL), and the mixture was stirred at 20° C. for 16 hours. The obtained reaction solution was diluted with saturated sodium carbonate (150 mL) and extracted with ethyl acetate (200 mL×2). The separated aqueous phase was added with hydrochloric acid (2 mol/L) until the pH was adjusted to 2, and then the mixture was extracted with ethyl acetate (200 mL×3). The combined organic phases were washed with saturated brine (500 mL×2), dried over anhydrous anhydrous sodium sulfate, and then filtered and concentrated under reduced pressure to obtain compound 3-7. LCMS (ESI) m/z: 387.1 [M+H]⁺.

Step E: 3-7 (20.6 g, 46.10 mmol) was dissolved in Eaton's reagent (160 mL), and the mixture was stirred at 20° C. for 16 hours. The obtained reaction solution was diluted with water (500 mL) and extracted with ethyl acetate (200 mL×3). The combined organic phases were washed with saturated brine (500 mL×3), dried over anhydrous sodium sulfate, filtered and then concentrated under reduced pressure to obtain compound 3-8. LCMS (ESI) m/z: 285.1 [M+H]⁺.

Step F: 3-8 (17 g, 59.81 mmol) was dissolved in dichloromethane (200 mL), and then p-toluenesulfonic acid monohydrate (5.69 g, 29.91 mmol) and 3,4-dihydropyran (7.55 g, 89.72 mmol) were added thereto. The mixture was stirred at 20° C. for 16 hours. The reaction solution was concentrated under reduced pressure to obtain a crude product. The crude product was purified by column chromatography (eluent: petroleum ether/ethyl acetate=10/1 to 15/2) to obtain compound 3-9.

Compound 3-9: $^1$H NMR (400 MHz, CDCl$_3$) δ=8.21 (s, 1H), 7.76 (dd, J=3.5, 8.8 Hz, 1H), 7.26 (dd, J=4.8, 9.0 Hz, 1H), 5.70 (td, J=2.9, 9.3 Hz, 1H), 4.77 (ddd, J=1.5, 7.2, 12.3 Hz, 1H), 4.10-4.01 (m, 2H), 3.08-2.95 (m, 1H), 2.34-2.25 (m, 1H), 1.97-1.83 (m, 2H), 1.80-1.74 (m, 2H), 1.62 (br d, J=1.6 Hz, 2H), 1.61-1.46 (m, 2H). LCMS (ESI) m/z: 369.1 [M+H]⁺.

Step G: A solution of 3-9 (6 g, 14.83 mmol) in tetrahydrofuran (20 mL) was slowly added dropwise to a solution of potassium bis(trimethylsilyl)amide (1.0 mol/L, 22.22 mL) in tetrahydrofuran (60 mL) under nitrogen atmosphere at −70° C. The mixture was stirred at −70° C. for 1 hour, and then a solution of N-phenyl-bis(trifluoromethanesulfonyl)imide (7.94 g, 22.22 mmol) in tetrahydrofuran (20 mL) was added thereto, and the mixture was stirred at 20° C. for 16 hours. The obtained reaction solution was quenched with saturated ammonium chloride (200 mL) and extracted with ethyl acetate (100 mL×2). The combined organic phases were washed with saturated brine (200 mL), dried over anhydrous sodium sulfate, filtered and then concentrated under reduced pressure to obtain a crude product. The crude product was purified by preparative HPLC (separation column: Phenomenex luna C18 (specification: 250 mm×80 mm, particle size: 10 m); mobile phase: [water (0.225% formic acid)-acetonitrile]; elution gradient: 65%-95%, 20 min) to obtain compound 3-10.

Compound 3-10: $^1$H NMR (400 MHz, DMSO-d$_6$) δ=8.17 (s, 1H), 7.54 (dd, J=0.6, 8.9 Hz, 1H), 7.42 (d, J=8.8 Hz, 1H), 5.85 (dd, J=2.2, 9.7 Hz, 1H), 4.76 (t, J=5.5 Hz, 2H), 3.89 (br d, J=12.0 Hz, 1H), 3.82-3.67 (m, 1H), 3.52 (q, J=11.0 Hz, 2H), 2.57 (br t, J=5.4 Hz, 2H), 2.45-2.29 (m, 1H), 2.05-1.95 (m, 2H), 1.82-1.67 (m, 1H), 1.66-1.53 (m, 2H). LCMS (ESI) m/z: 501.0 [M+H]⁺.

Step H: A solution of 3-11 (502 mg, 1.22 mmol), 3-10 (500 mg, 996.15 μmol), lithium chloride (126.69 mg, 2.99 mmol) and tetrakis(triphenylphosphine)palladium (0) (115.11 mg, 99.62 μmol) in toluene (5 mL) was stirred at 100° C. for 16 hours under nitrogen atmosphere. The obtained reaction solution was cooled to room temperature and filtered, and the filtrate was diluted with ethyl acetate (50 mL) and washed with saturated brine (50 mL×3), dried over anhydrous sodium sulfate, filtered and then concentrated under reduced pressure to obtain a crude product. The crude product was purified by preparative HPLC (separation column: Phenomenex luna C18 (specification: 150 mm×40 mm, particle size: 15 m); mobile phase: [water (0.1% trifluoroacetic acid)-acetonitrile]; elution gradient: 49%-79%, 11 min) to obtain compound 3-12. LCMS (ESI) m/z: 601.2 [M+H]⁺.

Step I: 3-12 (400 mg, 577.61 μmol) was dissolved in ethyl acetate solution of hydrogen chloride (4 mol/L, 10 mL). The reaction solution was stirred at 20° C. for 3 hours. The obtained reaction solution was concentrated under reduced pressure to obtain 3-13. LCMS (ESI) m/z: 417.1 [M+H]⁺.

Step J: N,N-Diisopropylethanamine (428.09 mg, 3.31 mmol) and 2-13 (149.44 mg, 794.95 μmol) were added to a solution of 3-13 (300 mg, 662.46 μmol) in N,N-dimethylformamide (10 mL), and the mixture was stirred at 20° C. for 16 hours. The reaction solution was diluted with ethyl acetate (100 mL) and washed with saturated brine (100 mL×2), dried over anhydrous sodium sulfate, filtered and then concentrated under reduced pressure to obtain a crude product. The crude product was purified by preparative HPLC (separation column: Phenomenex Gemini-NX C18 (specification: 75 mm×30 mm, particle size: 3 m); mobile phase: [water (ammonium bicarbonate, 10 mmol/L)-acetonitrile]; elution gradient: 22%-52%, 8 min) to obtain compound 3.

Compound 3: $^1$H NMR (400 MHz, DMSO-d$_6$) δ=13.10 (br s, 1H), 8.06 (s, 1H), 7.94 (d, J=1.5 Hz, 1H), 7.68 (d, J=1.4 Hz, 1H), 7.67 (d, J=7.0 Hz, 1H), 7.12 (dd, J=0.8, 8.7 Hz, 1H), 6.66 (d, J=8.7 Hz, 1H), 4.80 (t, J=5.7 Hz, 2H), 4.53 (t, J=6.1 Hz, 1H), 4.45-4.33 (m, 2H), 3.61 (t, J=7.2 Hz, 2H), 3.42 (q, J=11.6 Hz, 2H), 2.89-2.80 (m, 2H), 2.49-2.46 (m, 4H), 1.74-1.58 (m, 2H). LCMS (ESI) m/z: 477.1 [M+H]⁺.

Embodiment 4

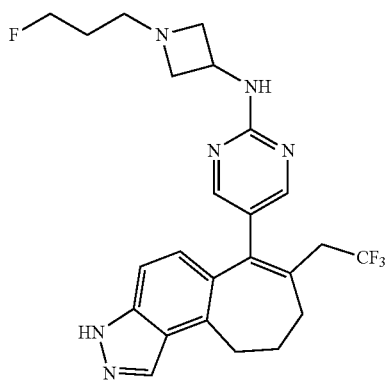

4

Synthetic Route:

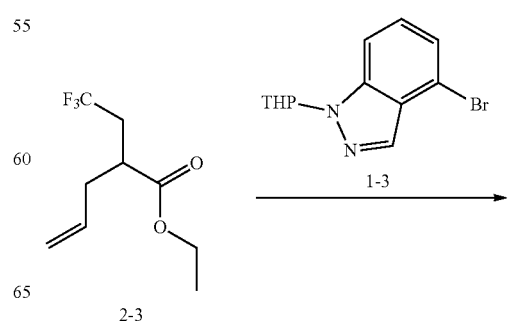

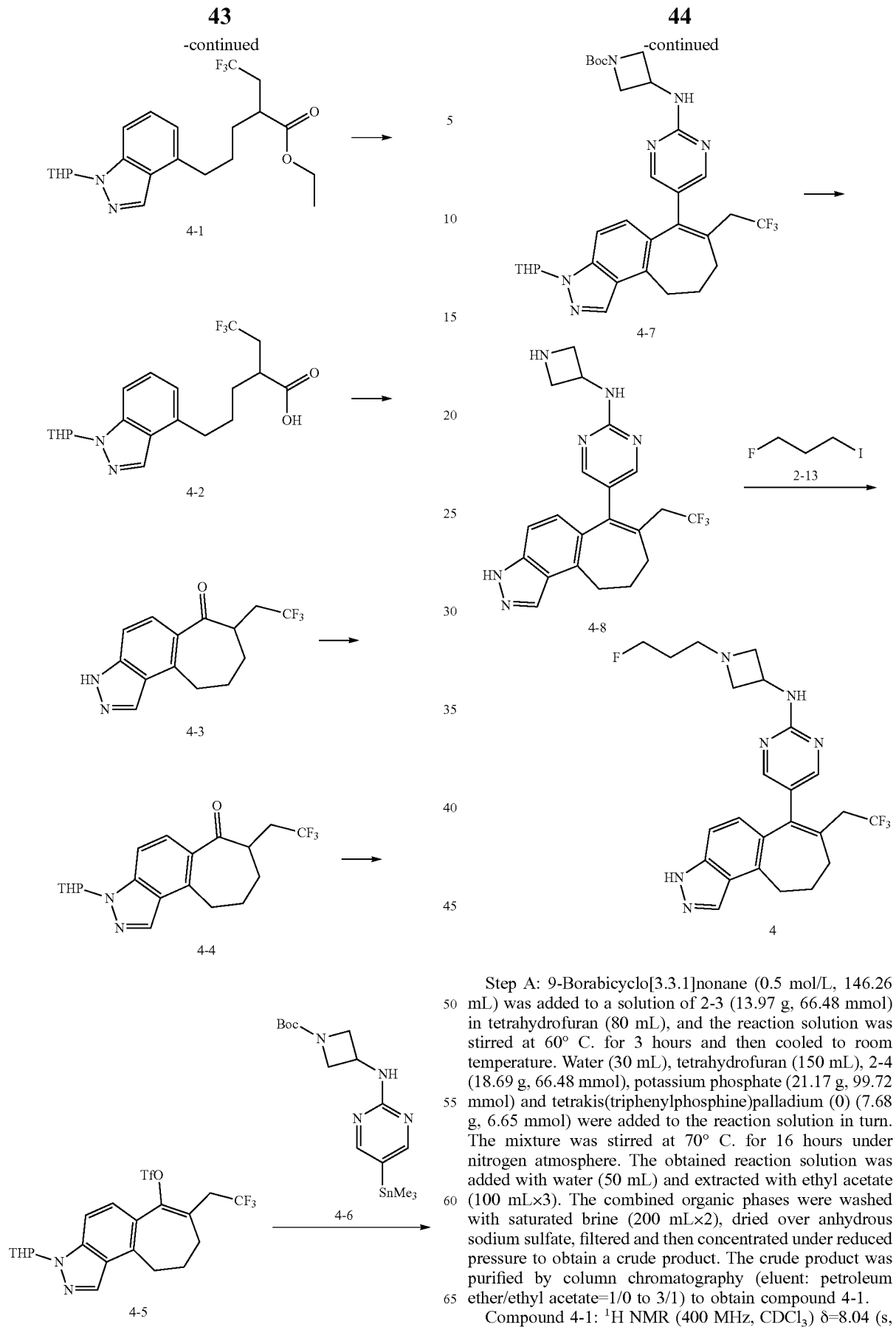

Step A: 9-Borabicyclo[3.3.1]nonane (0.5 mol/L, 146.26 mL) was added to a solution of 2-3 (13.97 g, 66.48 mmol) in tetrahydrofuran (80 mL), and the reaction solution was stirred at 60° C. for 3 hours and then cooled to room temperature. Water (30 mL), tetrahydrofuran (150 mL), 2-4 (18.69 g, 66.48 mmol), potassium phosphate (21.17 g, 99.72 mmol) and tetrakis(triphenylphosphine)palladium (0) (7.68 g, 6.65 mmol) were added to the reaction solution in turn. The mixture was stirred at 70° C. for 16 hours under nitrogen atmosphere. The obtained reaction solution was added with water (50 mL) and extracted with ethyl acetate (100 mL×3). The combined organic phases were washed with saturated brine (200 mL×2), dried over anhydrous sodium sulfate, filtered and then concentrated under reduced pressure to obtain a crude product. The crude product was purified by column chromatography (eluent: petroleum ether/ethyl acetate=1/0 to 3/1) to obtain compound 4-1.

Compound 4-1: $^1$H NMR (400 MHz, CDCl$_3$) δ=8.04 (s, 1H), 7.45 (d, J=8.5 Hz, 1H), 7.32 (dd, J=7.0, 8.4 Hz, 1H), 6.94 (d, J=6.9 Hz, 1H), 5.72 (dd, J=2.6, 9.5 Hz, 1H), 4.23-4.10 (m, 2H), 4.09-4.02 (m, 1H), 3.80-3.72 (m, 1H), 2.95 (t, J=7.2 Hz, 2H), 2.76-2.66 (m, 1H), 2.65-2.53 (m, 2H), 2.21-2.12 (m, 2H), 2.12-2.06 (m, 1H), 1.82-1.71 (m, 5H), 1.69-1.58 (m, 2H), 1.26-1.22 (m, 3H). LCMS (ESI) m/z: 413.1 [M+H]$^+$.

Step B: Sodium hydroxide (7.50 g, 187.47 mmol) was added to a mixed solution of 4-1 (19.33 g, 46.87 mmol) in methanol (150 mL) and water (50 mL), and the mixture was stirred at 25° C. for 16 hours. The obtained reaction solution was concentrated under reduced pressure to remove the solvent methanol, and the residue was diluted with water (150 mL) and extracted with dichloromethane (100 mL×2), and the pH value of aqueous phase was adjusted to 2 by adding with hydrochloric acid (2 mol/L) and then the mixture was extracted with ethyl acetate (80 mL×4). The combined organic phases were washed with saturated brine (200 mL×2), dried over anhydrous sodium sulfate, filtered and then concentrated under reduced pressure to obtain compound 4-2. LCMS (ESI) m/z: 385.1 [M+H]$^+$.

Step C: 4-2 (5.70 g, 14.83 mmol) was dissolved in polyphosphoric acid (60 mL), and the mixture was stirred at 110° C. for 16 hours. The obtained reaction solution was diluted with ice water (1000 mL) and extracted with ethyl acetate (200 mL×3). The combined organic phases were washed with saturated brine (200 mL×3), dried over anhydrous sodium sulfate, filtered and then concentrated under reduced pressure to obtain compound 4-3. LCMS (ESI) m/z: 283.1 [M+H]$^+$.

Step D: 4-3 (12 g, 41.51 mmol) was dissolved in dichloromethane (120 mL), and then 3,4-dihydropyran (5.36 g, 63.77 mmol) and p-toluenesulfonic acid monohydrate (4.04 mg, 21.26 mmol) were added thereto. The mixture was stirred at 25° C. for 16 hours. The reaction solution was diluted with water (100 mL) and extracted with ethyl acetate (100 mL×3). The combined organic phases were washed with saturated sodium carbonate solution (200 mL*2) and saturated brine (200 mL*1) in turn, dried over anhydrous sodium sulfate, and then the reaction solution was concentrated under reduced pressure to obtain a crude product. The crude product was purified by column chromatography (eluent: petroleum ether/ethyl acetate=1/0 to 0/1) to obtain compound 4-4.

Compound 4-4: $^1$H NMR (400 MHz, CDCl$_3$) δ=8.18 (s, 1H), 7.81 (dd, J=3.9, 8.7 Hz, 1H), 7.49 (br d, J=8.7 Hz, 1H), 5.73 (br d, J=9.0 Hz, 1H), 4.08-3.99 (m, 1H), 3.82-3.71 (m, 1H), 3.54 (br dd, J=6.2, 16.9 Hz, 1H), 3.33 (br d, J=2.7 Hz, 1H), 3.24-3.12 (m, 1H), 3.11-2.98 (m, 1H), 2.62-2.50 (m, 1H), 2.22-2.04 (m, 4H), 1.85-1.63 (m, 6H).

Step E: A solution of potassium bis(trimethylsilyl)amide in tetrahydrofuran (1.0 mol/L, 29.39 mL) was dissolved in tetrahydrofuran (10 mL) at −70° C. under nitrogen atmosphere, and then a solution of 4-4 (7.18 g, 19.59 mmol) in tetrahydrofuran (70 mL) was slowly added dropwise thereto. The mixture was stirred at −70° C. for 1 hour, and then a solution of N-phenyl-bis(trifluoromethanesulfonyl) imide (10.50 g, 29.39 mmol) in tetrahydrofuran (50 mL) was added thereto, and the mixture was stirred at 20° C. for 16 hours. The obtained reaction solution was quenched with saturated ammonium chloride aqueous solution (50 mL) and extracted with ethyl acetate (30 mL×2). The combined organic phases were washed with saturated brine (50 mL), dried over anhydrous sodium sulfate, filtered and then concentrated under reduced pressure to obtain a crude product. The crude product was purified by column chromatography (eluent: petroleum ether/ethyl acetate=1/0 to 0/1) to obtain compound 4-5.

Compound 4-5: $^1$H NMR (400 MHz, CDCl$_3$) δ=8.13 (s, 1H), 7.56-7.51 (m, 1H), 7.46-7.42 (m, 1H), 5.73 (dd, J=2.6, 9.5 Hz, 1H), 4.10-4.04 (m, 1H), 3.81-3.73 (m, 1H), 3.37-3.19 (m, 2H), 3.11-2.97 (m, 2H), 2.62-2.51 (m, 1H), 2.40 (t, J=7.0 Hz, 2H), 2.23-2.13 (m, 1H), 2.12-2.04 (m, 4H), 1.83-1.74 (m, 2H). LCMS (ESI) m/z: 499.2 [M+H]$^+$.

Step F: Lithium chloride (64.39 mg, 1.52 mmol), tetrakis(triphenylphosphine)palladium (0) (58.51 mg, 50.63 μmol) and 4-6 (252.36 mg, 506.29 mol) were added to a solution of 4-5 (250.98 mg, 607.55 μmol) in toluene (3 mL), and the mixture was stirred at 105° C. for 16 hours under nitrogen atmosphere. The obtained reaction solution was cooled and filtered, and the filtrate was diluted with water (10 mL) and ethyl acetate (10 mL), and then the phases were separated. The obtained organic phase was washed with saturated brine (10 mL×3), dried over anhydrous sodium sulfate, filtered and then concentrated under reduced pressure to obtain a crude product. The crude product was purified by thin-layer silica gel chromatography (eluent: petroleum ether/ethyl acetate=0/1) to obtain compound 4-7. LCMS (ESI) m/z: 599.2 [M+H]$^+$.

Step G: 4-7 (178 mg, 297.33 μmol) was dissolved in hydrochloric acid/ethyl acetate (4 mol/L, 2 mL). The mixture was stirred at 20° C. for 12 hours. The obtained reaction solution was concentrated under reduced pressure to obtain the hydrochloride of 4-8. LCMS (ESI) m/z: 415.1 [M+H]$^+$.

Step H: N,N-Diisopropylethanamine (20.64 mg, 159.69 μmol) and 2-13 (7.50 mg, 39.92 μmol) were added to a solution of 4-8 (30 mg, 39.92 μmol, hydrochloride) in acetonitrile (2 mL), and the mixture was stirred at 25° C. for 12 hours. The reaction solution was concentrated under reduced pressure to obtain a crude product. The crude product was purified by preparative HPLC (separation column: Waters Xbridge 150×25 mm, particle size: 5 m); mobile phase: [water (ammonium bicarbonate, 10 mmol/L) acetonitrile]; elution gradient: 37%-67%, 9 min) to obtain compound 4.

Compound 4: $^1$H NMR (400 MHz, CDCl$_3$) δ=10.79-9.59 (m, 1H), 8.18 (s, 1H), 8.08 (s, 2H), 7.25 (s, 1H), 6.83 (d, J=8.6 Hz, 1H), 5.84 (br d, J=1.4 Hz, 1H), 4.75 (t, J=7.0 Hz, 1H), 4.59 (t, J=5.8 Hz, 1H), 4.47 (t, J=5.8 Hz, 1H), 4.10-3.95 (m, 2H), 3.66-3.41 (m, 2H), 3.12 (q, J=10.7 Hz, 2H), 3.04 (br t, J=7.0 Hz, 2H), 2.91 (br s, 2H), 2.43 (quint, J=7.0 Hz, 2H), 2.18 (br t, J=7.0 Hz, 2H), 1.98-1.87 (m, 2H). LCMS (ESI) m/z: 475.2 [M+H]$^+$.

Embodiment 5

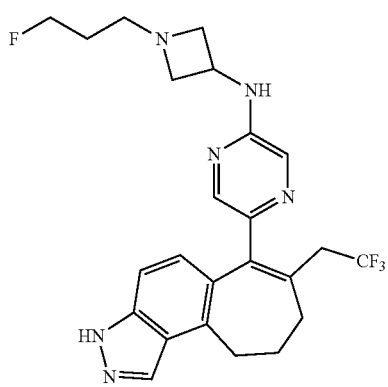 [SMILES: FCCCN1CC(Nc2ccc(C3=C(CC(F)(F)F)CCCc4c3ccc3[nH]ncc43)nc2)C1]

Synthetic Route:

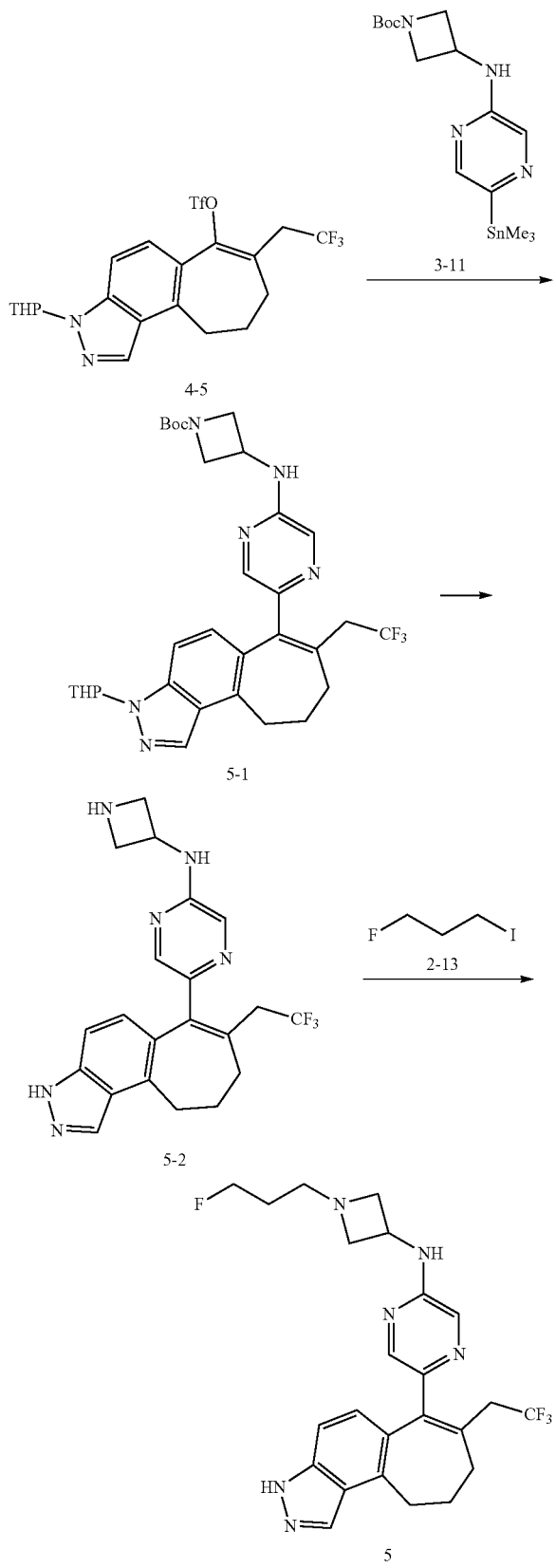

Step A: Lithium chloride (128.28 mg, 3.03 mmol), tetrakis(triphenylphosphine)palladium (0) (116.55 mg, 100.86 µmol) and 3-11 (502.74 mg, 1.01 mmol) were added to a solution of 4-5 (500 mg, 1.21 mmol) in toluene (3 mL), and the mixture was stirred at 105° C. for 16 hours under nitrogen atmosphere. The obtained reaction solution was cooled and filtered, and the filtrate was diluted with water (10 mL) and ethyl acetate (10 mL) and then the phases were separated. The obtained organic phase was washed with saturated brine (10 mL×3), dried over anhydrous sodium sulfate, filtered and then concentrated under reduced pressure to obtain a crude product. The crude product was purified by column chromatography (eluent: petroleum ether/ethyl acetate=1/0 to 0/1) to obtain compound 5-1. LCMS (ESI) m/z: 599.2 [M+H]$^+$.

Step B: 5-1 (320 mg, 534.53 µmol) was dissolved in hydrochloric acid/ethyl acetate (4 mol/L, 4 mL). The mixture was stirred at 20° C. for 20 hours. The reaction solution was concentrated under reduced pressure and then dissolved in hydrochloric acid/methanol (4 mol/L, 4 mL), and the mixture was stirred at 20° C. for 24 hours. The obtained reaction solution was concentrated under reduced pressure to obtain the hydrochloride of 5-2. LCMS (ESI) m/z: 415.1 [M+H]$^+$.

Step C: N,N-Diisopropylethanamine (137.58 mg, 1.06 mmol) and 2-13 (50.03 mg, 166.14 µmol) were added to a solution of 5-2 (200 mg, 266.14 µmol, hydrochloride) in acetonitrile (4 mL), and the mixture was stirred at 25° C. for 12 hours. 2-13 (40.02 mg, 212.91 mol) and N,N-diisopropylethylamine (137.59 mg, 1.06 mmol) were added to the reaction solution, and the mixture was stirred at 25° C. for 12 hours. The reaction solution was concentrated under reduced pressure to obtain a crude product. The crude product was purified by preparative HPLC (separation column: Welch Ultimate XB-SiOH 250×50, particle size: 10 m); mobile phase: [ethanol (0.1% ammonia water)-n-hexane]; elution gradient: 1%-40%, 15 min) to obtain compound 5.

Compound 5: $^1$H NMR (400 MHz, CDCl$_3$) δ=10.59-10.37 (m, 1H), 8.17 (s, 1H), 7.92 (d, J=0.9 Hz, 1H), 7.74 (s, 1H), 7.22 (d, J=8.7 Hz, 1H), 6.86 (d, J=8.7 Hz, 1H), 5.22 (br d, J=7.3 Hz, 1H), 4.57 (t, J=5.9 Hz, 1H), 4.54-4.49 (m, 1H), 4.45 (t, J=5.9 Hz, 1H), 3.76 (t, J=7.3 Hz, 2H), 3.35 (q, J=11.0 Hz, 2H), 3.10-2.99 (m, 4H), 2.64 (t, J=7.2 Hz, 2H), 2.43 (quin, J=6.9 Hz, 2H), 2.21-2.13 (m, 2H), 1.85-1.78 (m, 2H). LCMS (ESI) m/z: 475.0 [M+H]$^+$.

Embodiment 6

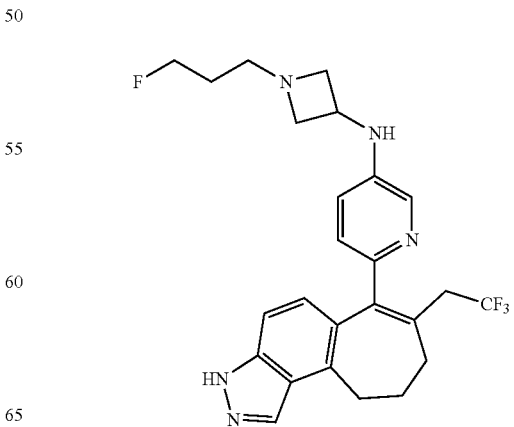

Synthetic Route:

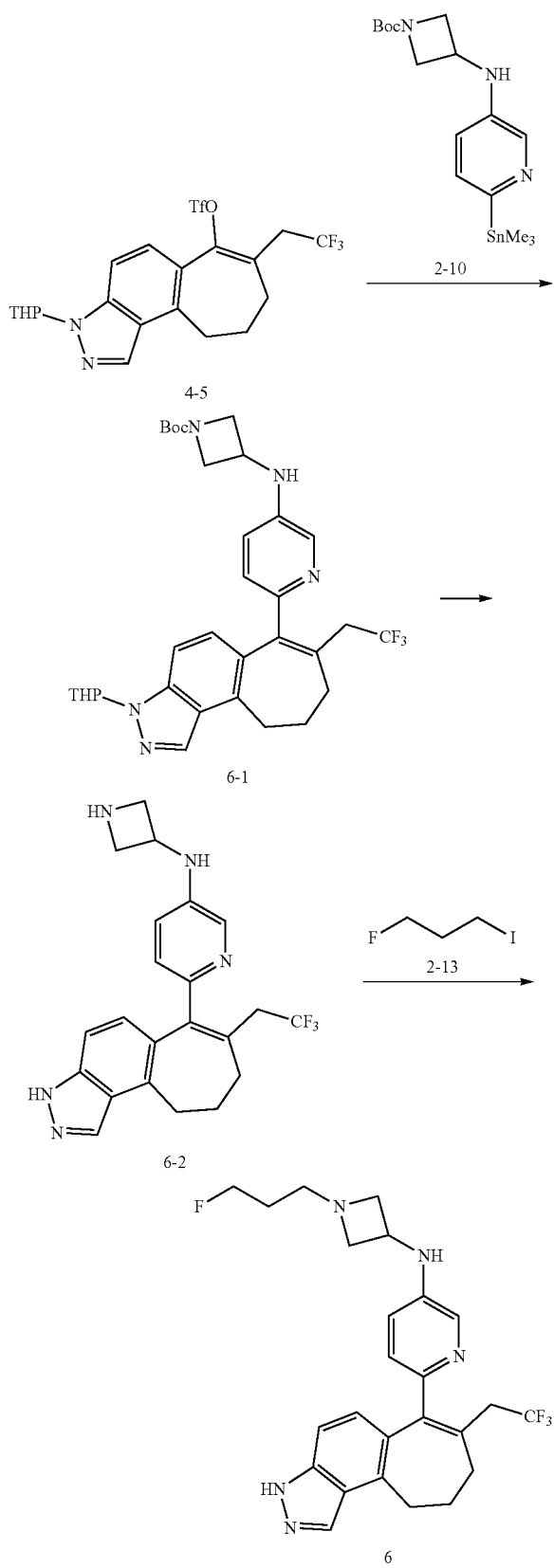

Step A: Lithium chloride (61.72 mg, 1.46 mmol), tetrakis(triphenylphosphine)palladium (0) (140.20 mg, 121.33 μmol) and 2-10 (500 mg, 1.21 mmol) were added to a solution of 4-5 (554.26 mg, 1.09 mmol) in toluene (3 mL), and the mixture was stirred at 100° C. for 16 hours under nitrogen atmosphere. The obtained reaction solution was cooled, and added with saturated potassium fluoride aqueous solution (50 mL), and the mixture was stirred for 0.5 hours and filtered. The filtrate was extracted with ethyl acetate (100 mL×2). The obtained organic phase was washed with saturated brine (100 mL), dried over anhydrous sodium sulfate, filtered and then concentrated under reduced pressure to obtain a crude product. The crude product was purified by column chromatography (eluent: petroleum ether/ethyl acetate=5/1 to 1/2) to obtain compound 6-1. LCMS (ESI) m/z: 598.4 [M+H]$^+$.

Step B: 6-1 (400 mg, 669.27 μmol) was dissolved in ethyl acetate solution of hydrogen chloride (4 mol/L, 10 mL). The mixture was stirred at 35° C. for 1 hour. The obtained reaction solution was concentrated under reduced pressure to obtain the hydrochloride of 6-2. LCMS (ESI) m/z: 414.2 [M+H]$^+$.

Step C: N,N-Diisopropylethanamine (232.68 mg, 1.80 mmol) and 2-13 (90.25 mg, 480.11 μmol) were added to a solution of 6-2 (270 mg, 600.13 μmol, hydrochloride) in acetonitrile (15 mL), and the mixture was stirred at 35° C. for 16 hours. The reaction solution was concentrated under reduced pressure to obtain a crude product. The crude product was purified by preparative HPLC (separation column: Waters Xbridge (specification: 150 mm×25 mm, particle size: 5 m); mobile phase: [water (0.05% ammonia water v/v)-acetonitrile]; elution gradient: 33%-57%, 9 min) to obtain compound 6.

Compound 6: $^1$H NMR (400 MHz, CD$_3$OD) δ=8.32-8.13 (m, 1H), 8.00-7.88 (m, 1H), 7.33-7.21 (m, 1H), 7.05-6.89 (m, 2H), 6.83-6.72 (m, 1H), 4.60-4.50 (m, 1H), 4.46-4.34 (m, 1H), 4.24-4.07 (m, 1H), 3.89-3.79 (m, 2H), 3.32-3.20 (m, 2H), 3.17-3.08 (m, 2H), 3.07-2.97 (m, 2H), 2.74-2.62 (m, 2H), 2.53-2.39 (m, 2H), 2.24-2.11 (m, 2H), 1.90-1.70 (m, 2H). LCMS (ESI) m/z: 474.2 [M+H]$^+$.

Embodiment 7

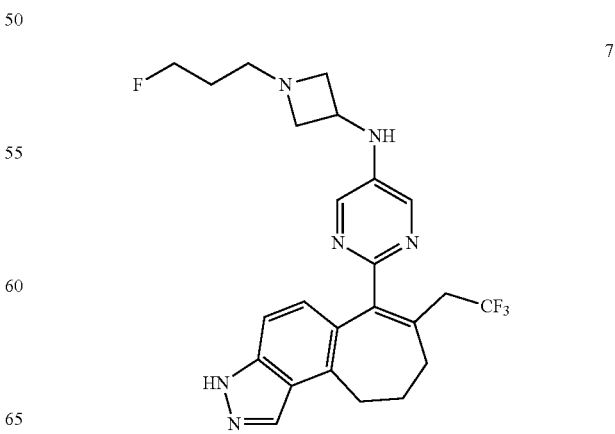

Synthetic Route:

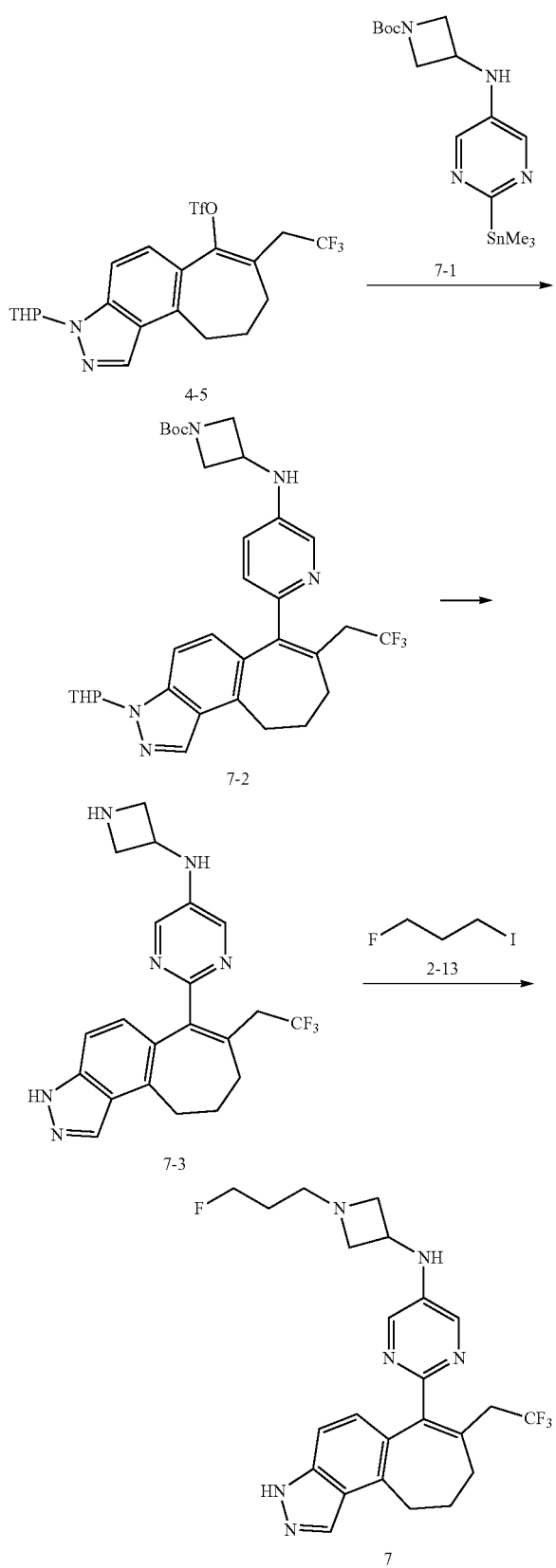

Step A: A solution of 4-5 (200 mg, 401.25 μmol), 7-1 (200.57 mg, 485.52 μmol), lithium chloride (51.03 mg, 1.20 mmol), tetrakis(triphenylphosphine)palladium (0) (46.37 mg, 40.13 μmol) in toluene (6 mL) was stirred at 100° C. for 12 hours under nitrogen atmosphere. The reaction solution was cooled, and added with saturated potassium fluoride aqueous solution (20 mL), and the mixture was stirred for 1 hour and filtered, and diluted with ethyl acetate (30 mL×2) and the phases were separated. The obtained organic phase was dried over anhydrous sodium sulfate, filtered and then concentrated under reduced pressure to obtain a crude product. The crude product was purified by thin-layer silica gel chromatography (eluent: petroleum ether/ethyl acetate=1/2) to obtain compound 7-2. LCMS (ESI) m/z: 599.3 [M+H]$^+$.

Step B: A solution of hydrogen chloride in 1,4-dioxane (4 mol/L, 998.35 μL) was added to a solution of 7-2 (20 mg, 33.41 μmol) in 1,4-dioxane (1 mL). The mixture was stirred at 10 to 20° C. for 12 hours. The obtained reaction solution was concentrated under reduced pressure to obtain the hydrochloride of 7-3. LCMS (ESI) m/z: 517.2 [M+H]$^+$.

Step C: N,N-Diisopropylethanamine (17.20 mg, 133.07 μmol) was added to a solution of 7-3 (15 mg, 33.27 μmol, hydrochloride) and 2-13 (6.25 mg, 33.27 μmol) in acetonitrile (2 mL), and the mixture was stirred at 10 to 20° C. for 24 hours. The reaction solution was filtered and concentrated under reduced pressure to obtain a crude product. The crude product was purified by preparative HPLC (separation column: Welch Ultimate XB-CN 250 mm×50 mm, particle size: 10 m); mobile phase: [ethanol (0.05% ammonia water)-n-hexane]; elution gradient: 5%-45%, 15 min) to obtain compound 7.

Compound 7: $^1$H NMR (400 MHz, CDCl$_3$) δ=10.57-9.96 (m, 1H), 8.14 (s, 1H), 8.12 (s, 2H), 7.20 (d, J=8.7 Hz, 1H), 6.78 (d, J=8.6 Hz, 1H), 4.69-4.61 (m, 1H), 4.58 (t, J=5.8 Hz, 1H), 4.46 (t, J=5.7 Hz, 1H), 4.21 (qd, J=6.3, 12.7 Hz, 1H), 3.84 (br t, J=7.3 Hz, 2H), 3.51 (q, J=11.3 Hz, 2H), 3.23 (br s, 2H), 3.08 (t, J=7.0 Hz, 2H), 2.76 (br t, J=7.2 Hz, 2H), 2.43 (quint, J=6.9 Hz, 2H), 2.21-2.15 (m, 2H), 1.91-1.77 (m, 2H). LCMS (ESI) m/z: 475.1 [M+H]$^+$.

Embodiment 8

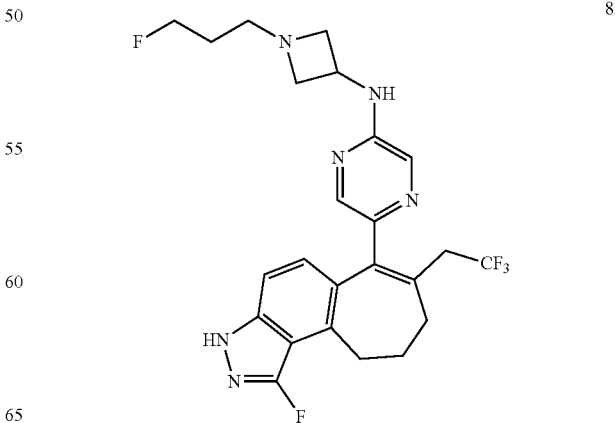

8

Synthetic Route:

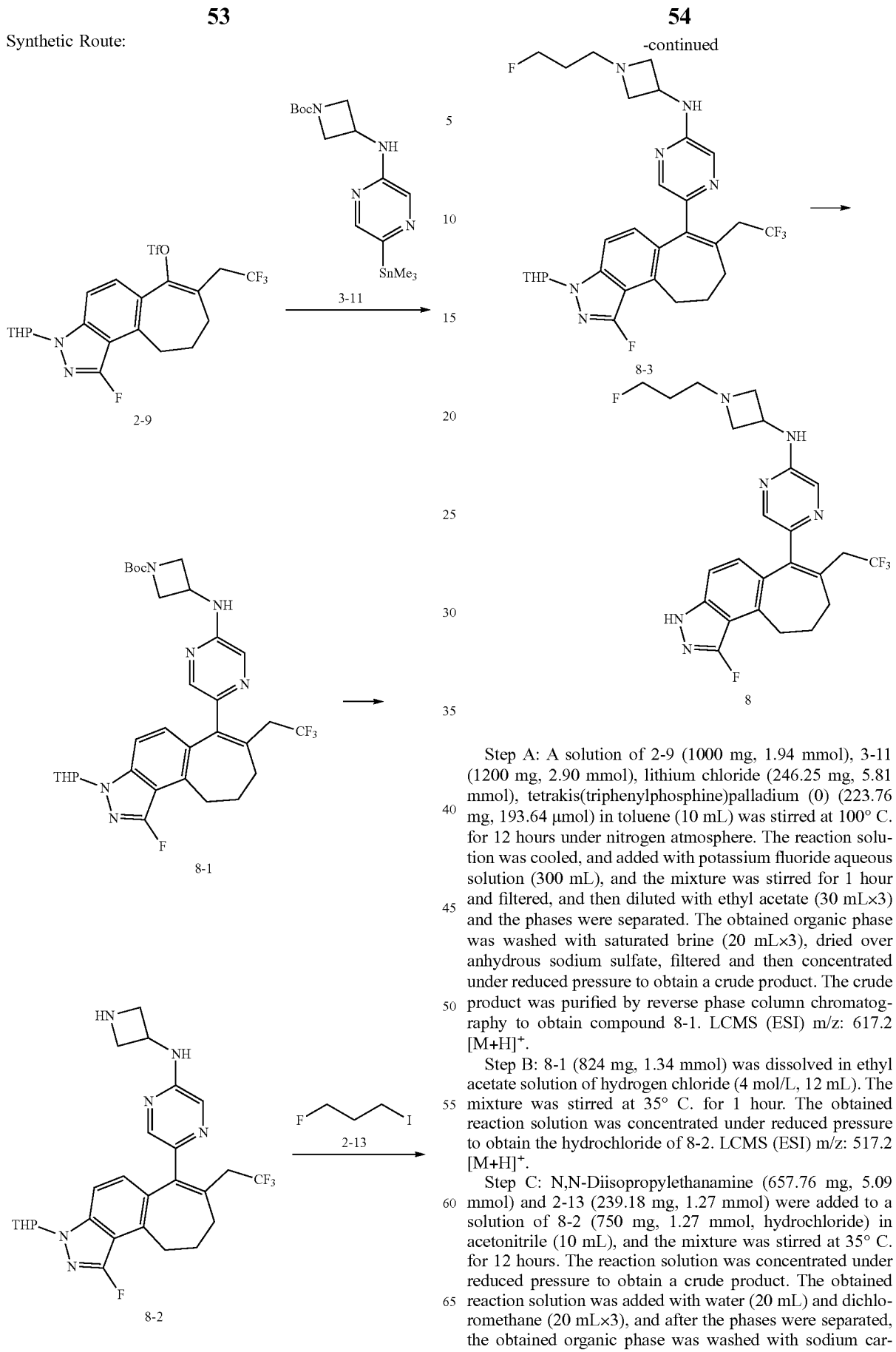

Step A: A solution of 2-9 (1000 mg, 1.94 mmol), 3-11 (1200 mg, 2.90 mmol), lithium chloride (246.25 mg, 5.81 mmol), tetrakis(triphenylphosphine)palladium (0) (223.76 mg, 193.64 µmol) in toluene (10 mL) was stirred at 100° C. for 12 hours under nitrogen atmosphere. The reaction solution was cooled, and added with potassium fluoride aqueous solution (300 mL), and the mixture was stirred for 1 hour and filtered, and then diluted with ethyl acetate (30 mL×3) and the phases were separated. The obtained organic phase was washed with saturated brine (20 mL×3), dried over anhydrous sodium sulfate, filtered and then concentrated under reduced pressure to obtain a crude product. The crude product was purified by reverse phase column chromatography to obtain compound 8-1. LCMS (ESI) m/z: 617.2 [M+H]$^+$.

Step B: 8-1 (824 mg, 1.34 mmol) was dissolved in ethyl acetate solution of hydrogen chloride (4 mol/L, 12 mL). The mixture was stirred at 35° C. for 1 hour. The obtained reaction solution was concentrated under reduced pressure to obtain the hydrochloride of 8-2. LCMS (ESI) m/z: 517.2 [M+H]$^+$.

Step C: N,N-Diisopropylethanamine (657.76 mg, 5.09 mmol) and 2-13 (239.18 mg, 1.27 mmol) were added to a solution of 8-2 (750 mg, 1.27 mmol, hydrochloride) in acetonitrile (10 mL), and the mixture was stirred at 35° C. for 12 hours. The reaction solution was concentrated under reduced pressure to obtain a crude product. The obtained reaction solution was added with water (20 mL) and dichloromethane (20 mL×3), and after the phases were separated, the obtained organic phase was washed with sodium carbonate aqueous solution (20 mL×2). The combined organic phases were washed with saturated brine (20 mL×2), dried over anhydrous sodium sulfate, filtered and then concentrated under reduced pressure to obtain compound 8-3.

Step D: Trifluoroacetic acid (2 mL) was added to a solution of 8-3 (650 mg, 1.13 mmol) in dichloromethane (6 mL). The reaction solution was stirred at 20° C. for 12 hours. The reaction solution was concentrated under reduced pressure to obtain a crude product. The crude product was purified by preparative HPLC (separation column: Waters Xbridge 150 mm×25 mm, particle size: 5 m); mobile phase: [water (0.05% ammonia water)-acetonitrile]; elution gradient: 38%-68%, 9 min) to obtain compound 8.

Compound 8: $^1$H NMR (400 MHz, CDCl$_3$) δ=7.91 (s, 1H), 7.68 (s, 1H), 7.09-7.03 (m, 1H), 6.81 (d, J=8.8 Hz, 1H), 4.60-4.50 (m, 2H), 4.42 (t, J=5.6 Hz, 1H), 3.82 (br t, J=7.6 Hz, 2H), 3.39-3.21 (m, 4H), 3.04 (br t, J=6.8 Hz, 2H), 2.77 (br t, J=7.1 Hz, 2H), 2.39 (quint, J=6.9 Hz, 2H), 2.16-2.08 (m, 2H), 1.89-1.73 (m, 2H). LCMS (ESI) m/z: 474.2 [M+H]$^+$.

Embodiment 9

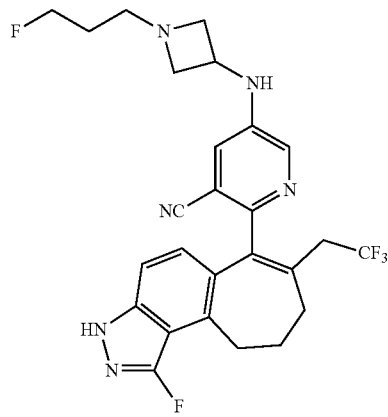

9

Synthetic Route:

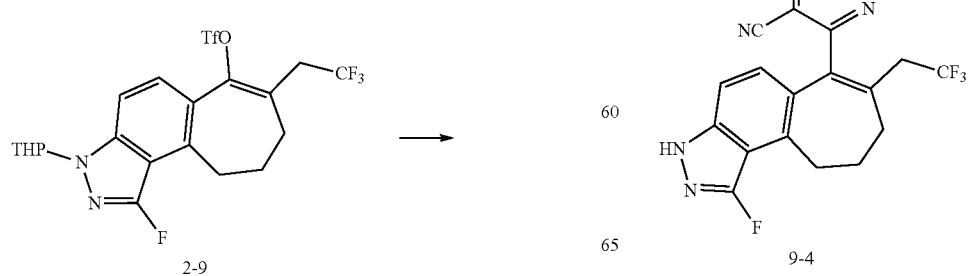

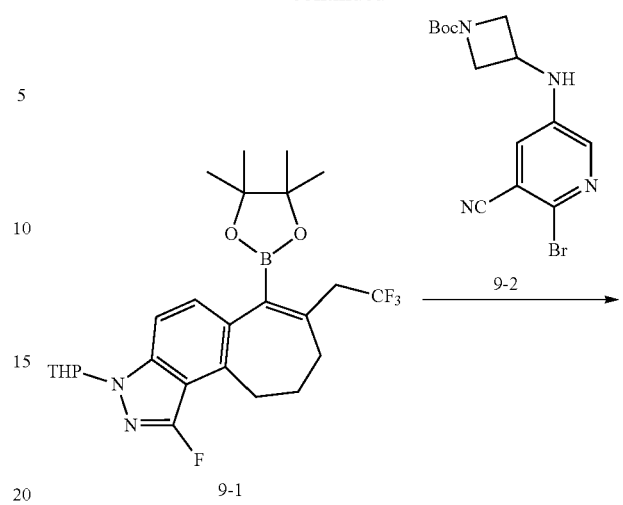

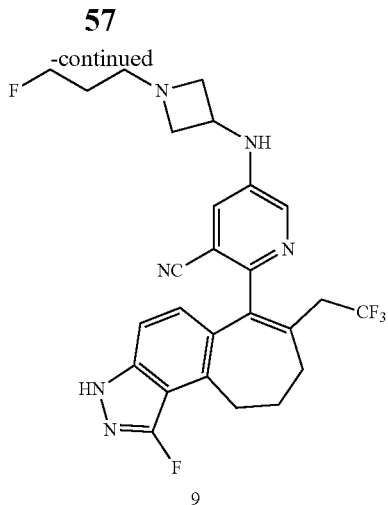

9

Step A: Triphenylphosphine (41.05 mg, 156.49 μmol), potassium phenolate (689.60 mg, 5.22 mmol), potassium bromide (465.56 mg, 3.90 mmol), dichlorobis(triphenylphosphine)palladium(II) (54.92 mg, 78.24 μmol) were added to a solution of 2-9 (1300 mg, 2.61 mmol), bis(pinacolato)diboron (993.46 mg, 3.91 mmol) in toluene (15 mL). The reaction was stirred at 50° C. for 2 hours under nitrogen atmosphere. The obtained reaction solution was cooled and filtered, and the filter cake was washed with dichloromethane (15 mL), and concentrated under reduced pressure to obtain a crude product. The crude product was purified by column chromatography (eluent: petroleum ether/ethyl acetate=1/0 to 0/1) to obtain compound 9-1. LCMS (ESI) m/z: 477.2 [M+H]$^+$.

Step B: 9-1 (200 mg, 566.23 μmol), 9-2 (279.90 mg, 566.23 μmol), sodium carbonate (228.05 mg, 2.15 mmol) and [1,1-bis(diphenylphosphino)ferrocene]palladium dichloride dichloromethane (46.24 mg, 56.62 μmol) were added to ethylene glycol dimethyl ether (3 mL) and water (1.08 mL). Under nitrogen atmosphere, the reaction was heated to 120° C. and stirred for 1 hour under microwave irradiation. The obtained reaction solution was cooled and filtered, and the filtrate was diluted with water (20 mL) and ethyl acetate (20 mL×3) and then the phases were separated. The obtained organic phase was washed with saturated brine (10 mL×1), dried over anhydrous sodium sulfate, filtered and then concentrated under reduced pressure to obtain a crude product. The crude product was purified by thin-layer silica gel chromatography (eluent: petroleum ether/ethyl acetate=1/1) to obtain compound 9-3. LCMS (ESI) m/z: 641.1 [M+H]$^+$.

Step C: 9-3 (177 mg, 276.27 μmol) was dissolved in ethyl acetate solution of hydrogen chloride (4 mol/L, 3 mL). The mixture was stirred at 35° C. for 1 hour. The obtained reaction solution was concentrated under reduced pressure to obtain the hydrochloride of 9-4. LCMS (ESI) m/z: 457.1 [M+H]$^+$.

Step D: N,N-Diisopropylethanamine (136.72 mg, 1.06 mmol) and 2-13 (59.66 mg, 317.36 μmol) were added to a solution of 9-4 (140 mg, 264.47 μmol, hydrochloride) in acetonitrile (3 mL), and the mixture was stirred at 35° C. for 12 hours. The obtained reaction solution was added with dichloromethane (10 mL), and washed with sodium carbonate aqueous solution (10 mL×2). The obtained organic phase was washed with saturated brine (10 mL×1), dried over anhydrous sodium sulfate, filtered and then concentrated under reduced pressure to obtain a crude product. The crude product was purified by preparative HPLC (separation column: Waters Xbridge 150×25 mm, particle size: 5 m); mobile phase: [water (0.225% formic acid)-acetonitrile]; elution gradient: 15%-45%, 10 min) to obtain compound 9.

Compound 9: $^1$H NMR (400 MHz, DMSO-d$_6$) δ=12.56 (s, 1H), 8.24 (d, J=2.8 Hz, 1H), 8.20 (s, 1H), 7.25-7.17 (m, 2H), 7.03 (d, J=6.9 Hz, 1H), 6.67 (d, J=8.8 Hz, 1H), 4.52 (t, J=6.0 Hz, 1H), 4.40 (t, J=6.1 Hz, 1H), 4.05 (sext, J=6.5 Hz, 1H), 3.67 (t, J=7.0 Hz, 2H), 3.20-2.92 (m, 4H), 2.82 (t, J=6.8 Hz, 2H), 2.49-2.46 (m, 2H), 2.45-2.30 (m, 2H), 2.20-1.92 (m, 2H), 1.74-1.59 (m, 2H). LCMS (ESI) m/z: 517.3 [M+H]$^+$.

Embodiment 10

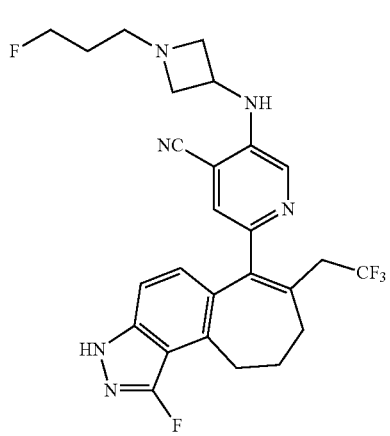

10

Synthetic Route:

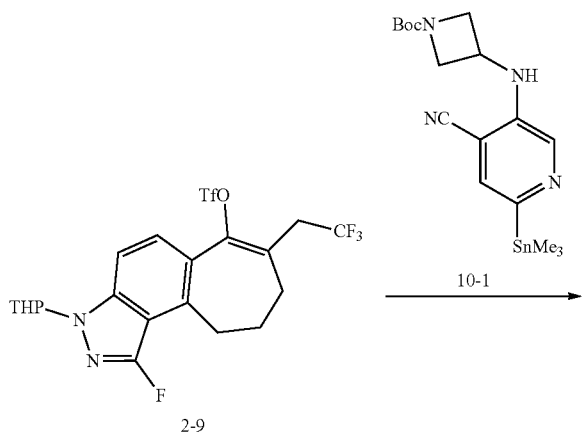

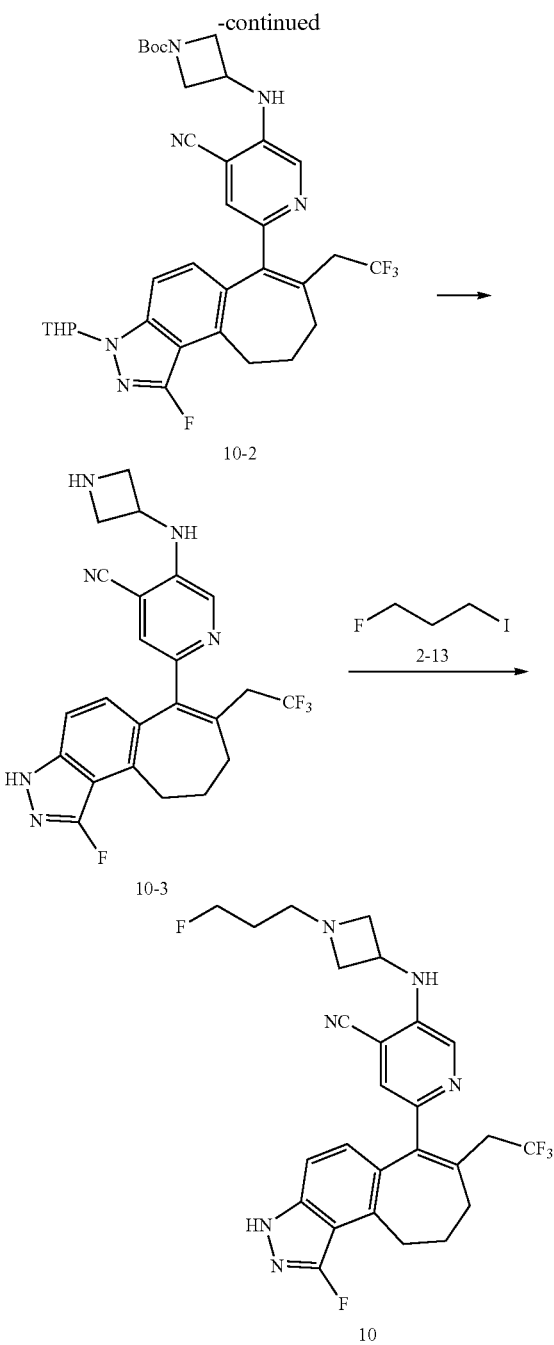

(eluent: petroleum ether/ethyl acetate=1/2) to obtain compound 10-2. LCMS (ESI) m/z: 641.2 [M+H]⁺.

Step B: 10-2 (152 mg, 237.25 μmol) was dissolved in ethyl acetate solution of hydrogen chloride (4 mol/L, 5 mL). The mixture was stirred at 35° C. for 1 hour. The obtained reaction solution was concentrated under reduced pressure to obtain the hydrochloride of 10-3. LCMS (ESI) m/z: 457.1 [M+H]⁺.

Step C: N,N-Diisopropylethanamine (122.07 mg, 944.54 μmol) and 2-13 (53.27 mg, 283.36 μmol) were added to a solution of 10-3 (125 mg, 236.13 μmol, hydrochloride) in acetonitrile (3 mL), and the mixture was stirred at 35° C. for 12 hours. The reaction solution was concentrated under reduced pressure to obtain a crude product. The crude product was purified by preparative HPLC (separation column: Waters Xbridge 150×25 mm, particle size: m); mobile phase: [water (0.05% ammonia water)-acetonitrile]; elution gradient: 40%-70%, 9 min) to obtain compound 10.

Compound 10: $^1$H NMR (400 MHz, CD$_3$OD) δ=8.11 (s, 1H), 7.18 (dd, J=2.5, 8.9 Hz, 1H), 7.14 (s, 1H), 6.80 (d, J=8.9 Hz, 1H), 4.54 (t, J=5.8 Hz, 1H), 4.44-4.34 (m, 2H), 3.87-3.81 (m, 2H), 3.38-3.32 (m, 2H), 3.18 (dd, J=8.3, 6.6 Hz, 2H), 3.09 (t, J=7.0 Hz, 2H), 2.69 (t, J=7.4 Hz, 2H), 2.47-2.38 (m, 2H), 2.16 (t, J=7.1 Hz, 2H), 1.86-1.71 (m, 2H). LCMS (ESI) m/z: 517.2 [M+H]⁺.

Embodiment 11

Step A: Lithium chloride (73.87 mg, 1.74 mmol), tetrakis(triphenylphosphine)palladium (0) (67.13 mg, 58.09 μmol) and 10-1 (371.27 mg, 849.35 μmol) were added to a solution of 2-9 (300 mg, 580.91 μmol) in toluene (5 mL), and the mixture was stirred at 105° C. for 12 hours under nitrogen atmosphere. The reaction solution was cooled, and added with potassium fluoride aqueous solution (100 mL), and the mixture was stirred at room temperature for 1 hour and filtered, and then diluted with ethyl acetate (30 mL×3) and the phases were separated. The combined organic phases were washed with saturated brine (20 mL×3), dried over anhydrous sodium sulfate, filtered and then concentrated under reduced pressure to obtain a crude product. The crude product was purified by thin-layer silica gel chromatography Synthetic Route:

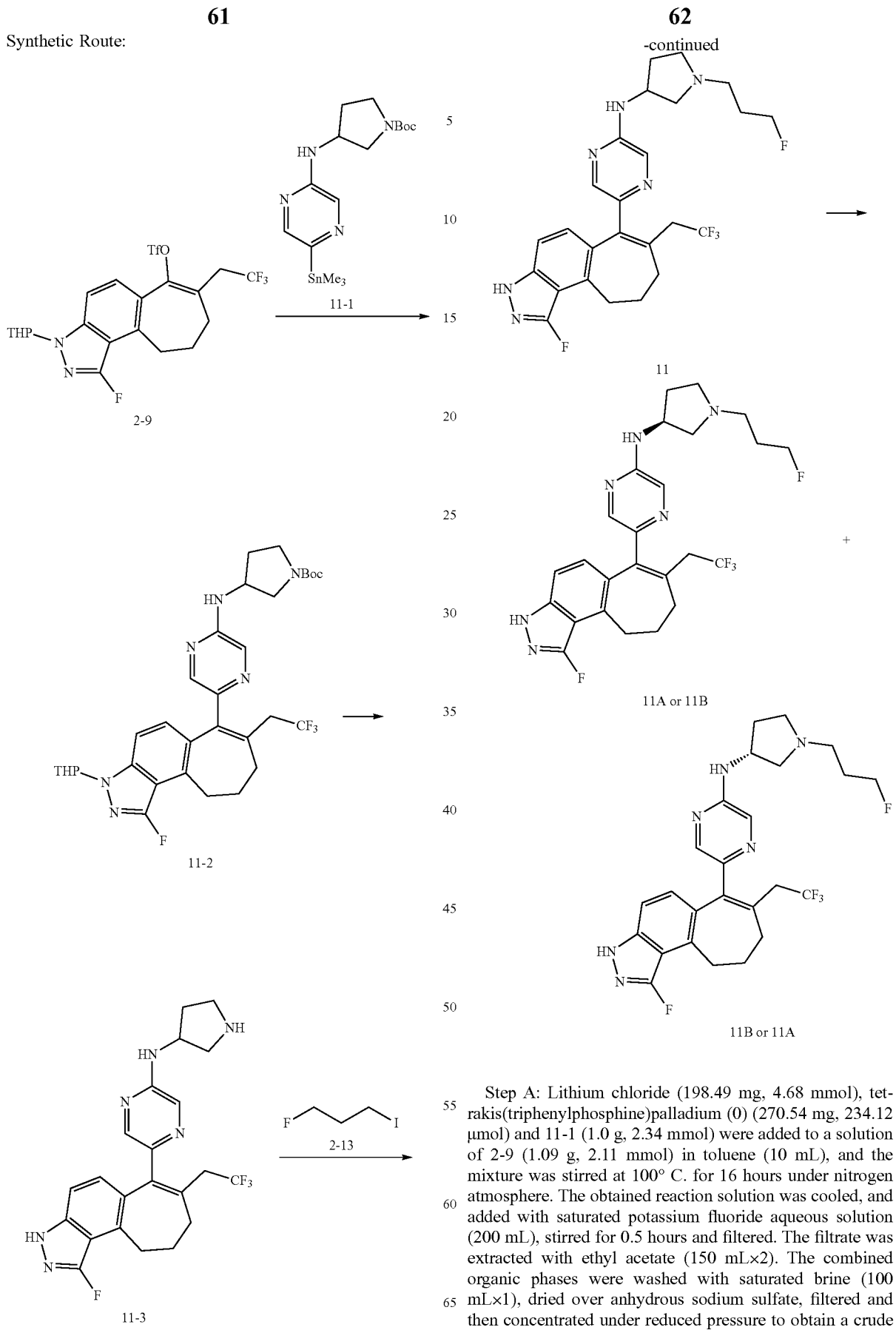

Step A: Lithium chloride (198.49 mg, 4.68 mmol), tetrakis(triphenylphosphine)palladium (0) (270.54 mg, 234.12 µmol) and 11-1 (1.0 g, 2.34 mmol) were added to a solution of 2-9 (1.09 g, 2.11 mmol) in toluene (10 mL), and the mixture was stirred at 100° C. for 16 hours under nitrogen atmosphere. The obtained reaction solution was cooled, and added with saturated potassium fluoride aqueous solution (200 mL), stirred for 0.5 hours and filtered. The filtrate was extracted with ethyl acetate (150 mL×2). The combined organic phases were washed with saturated brine (100 mL×1), dried over anhydrous sodium sulfate, filtered and then concentrated under reduced pressure to obtain a crude product. The crude product was purified by column chromatography (eluent: petroleum ether/ethyl acetate=5/1 to 1/1) to obtain compound 11-2. LCMS (ESI) m/z: 631.4 [M+H]⁺.

Step B: 11-2 (1.4 g, 2.22 mmol) was dissolved in hydrochloric acid/ethyl acetate (4 mol/L, 30 mL). The mixture was stirred at 35° C. for 1 hour. The obtained reaction solution was concentrated under reduced pressure to obtain the hydrochloride of 11-3. LCMS (ESI) m/z: 447.3 [M+H]⁺.

Step C: N,N-Diisopropylethanamine (802.91 mg, 6.21 mmol) and 2-13 (389.27 mg, 2.07 mmol) were added to a solution of 11-3 (1.0 g, 2.07 mmol, hydrochloride) in acetonitrile (20 mL), and the mixture was stirred at 35° C. for 13 hours. The reaction solution was concentrated under reduced pressure to obtain a crude product. The crude product was purified by preparative HPLC (separation column: Waters Xbridge 250 mm×50 mm, particle size: 5 m); mobile phase: [water (0.1% ammonia water)-acetonitrile]; elution gradient: 42%-70%, 9 min) to obtain compound 11. LCMS (ESI) m/z: 507.4 [M+H]⁺

Step D: 11 (180 mg, 355.37 μmol) was separated by SFC (separation column: Daicel ChiralPak IG (specification: 250 mm×30 mm, particle size: 10 m); mobile phase: [0.05% DEA, MeOH]; CO₂%: 5%-40%, 3 min) to obtain 11A (retention time=1.710 min, ee value: 97.1%) and 11B (retention time=1.832 min, ee value: 95.1%).

Compound 11A: ¹H NMR (400 MHz, CD₃OD) δ=7.96 (d, J=1.5 Hz, 1H), 7.78-7.73 (m, 1H), 7.24-7.17 (m, 1H), 6.92-6.84 (m, 1H), 4.61-4.55 (m, 1H), 4.50-4.42 (m, 2H), 3.43-3.36 (m, 2H), 3.16-3.05 (m, 3H), 3.01-2.90 (m, 1H), 2.83-2.69 (m, 4H), 2.51-2.36 (m, 3H), 2.23-2.14 (m, 2H), 2.04-1.91 (m, 2H), 1.91-1.81 (m, 1H). LCMS (ESI) m/z: 507.2 [M+H]⁺.

Compound 11B: ¹H NMR (400 MHz, CD₃OD) δ=7.99-7.89 (m, 1H), 7.79-7.68 (m, 1H), 7.29-7.15 (m, 1H), 6.97-6.83 (m, 1H), 4.62-4.52 (m, 1H), 4.50-4.34 (m, 2H), 3.43-3.36 (m, 2H), 3.16-3.07 (m, 2H), 3.05-2.96 (m, 1H), 2.87-2.76 (m, 1H), 2.61 (br s, 3H), 2.60-2.53 (m, 1H), 2.50-2.32 (m, 3H), 2.22-2.15 (m, 2H), 2.05-1.85 (m, 2H), 1.84-1.72 (m, 1H). LCMS (ESI) m/z: 507.2 [M+H]⁺.

Embodiment 12

Synthetic Route:

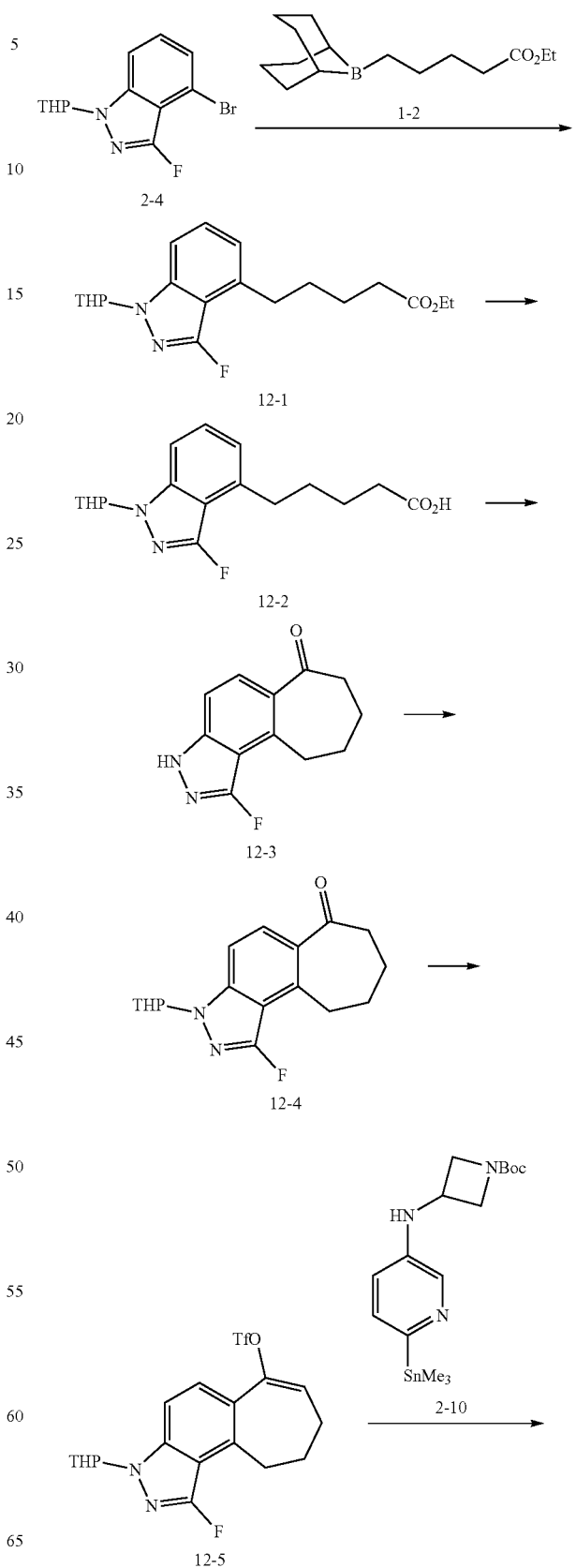

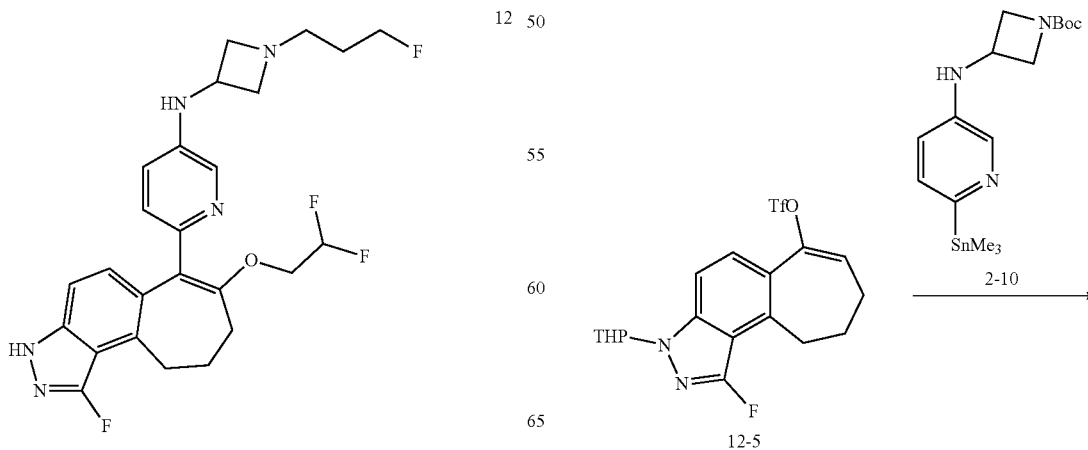

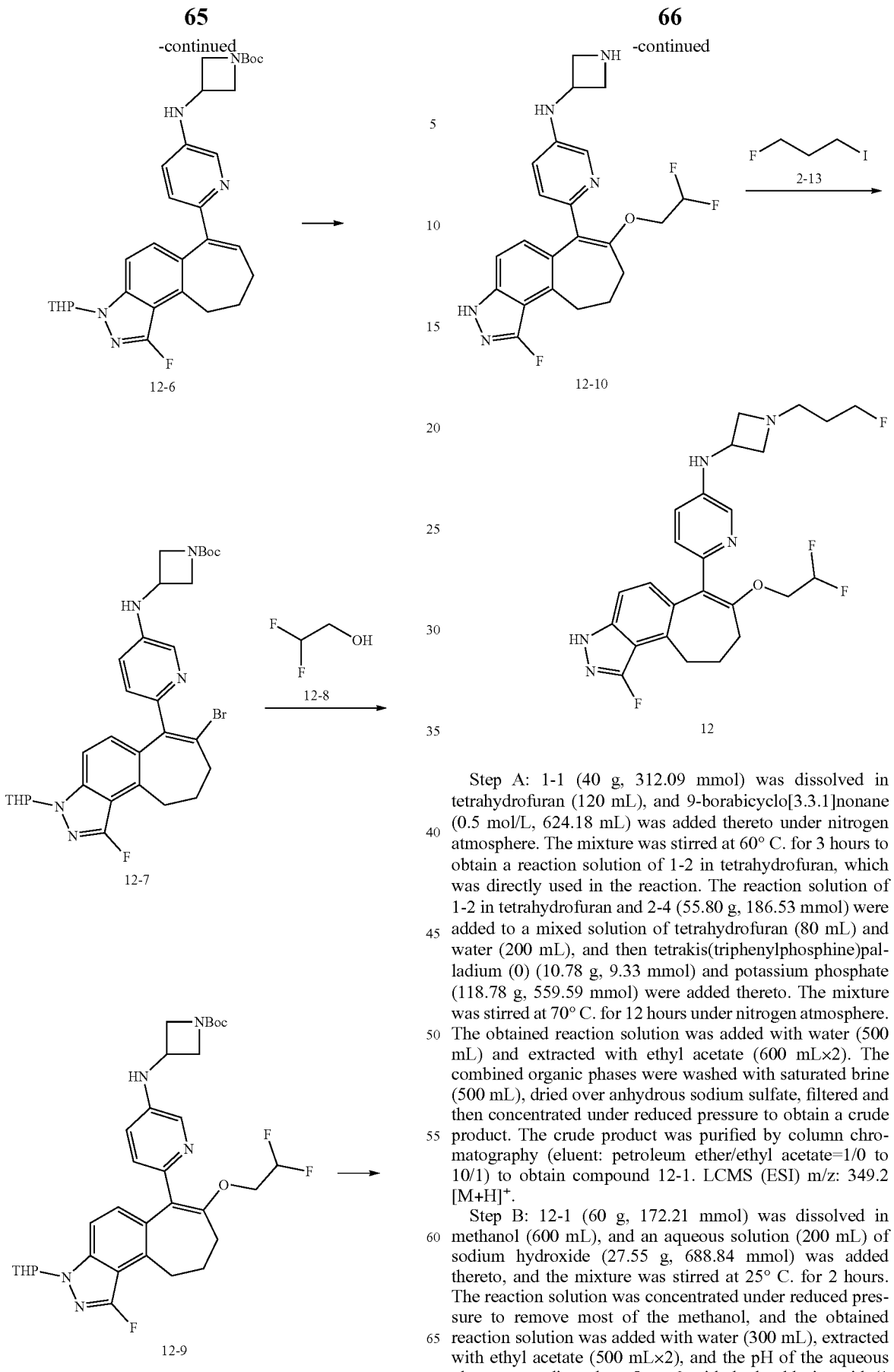

Step A: 1-1 (40 g, 312.09 mmol) was dissolved in tetrahydrofuran (120 mL), and 9-borabicyclo[3.3.1]nonane (0.5 mol/L, 624.18 mL) was added thereto under nitrogen atmosphere. The mixture was stirred at 60° C. for 3 hours to obtain a reaction solution of 1-2 in tetrahydrofuran, which was directly used in the reaction. The reaction solution of 1-2 in tetrahydrofuran and 2-4 (55.80 g, 186.53 mmol) were added to a mixed solution of tetrahydrofuran (80 mL) and water (200 mL), and then tetrakis(triphenylphosphine)palladium (0) (10.78 g, 9.33 mmol) and potassium phosphate (118.78 g, 559.59 mmol) were added thereto. The mixture was stirred at 70° C. for 12 hours under nitrogen atmosphere. The obtained reaction solution was added with water (500 mL) and extracted with ethyl acetate (600 mL×2). The combined organic phases were washed with saturated brine (500 mL), dried over anhydrous sodium sulfate, filtered and then concentrated under reduced pressure to obtain a crude product. The crude product was purified by column chromatography (eluent: petroleum ether/ethyl acetate=1/0 to 10/1) to obtain compound 12-1. LCMS (ESI) m/z: 349.2 [M+H]⁺.

Step B: 12-1 (60 g, 172.21 mmol) was dissolved in methanol (600 mL), and an aqueous solution (200 mL) of sodium hydroxide (27.55 g, 688.84 mmol) was added thereto, and the mixture was stirred at 25° C. for 2 hours. The reaction solution was concentrated under reduced pressure to remove most of the methanol, and the obtained reaction solution was added with water (300 mL), extracted with ethyl acetate (500 mL×2), and the pH of the aqueous phase was adjusted to 5 to 6 with hydrochloric acid (1 mol/L), and then the mixture was extracted with ethyl acetate (500 mL×3). The combined organic phases were dried over anhydrous sodium sulfate, filtered and then concentrated under reduced pressure to obtain compound 12-2. LCMS (ESI) m/z: 321.1 [M+H]$^+$.

Step C: 12-2 (10 g, 31.22 mmol) was dissolved in Eaton's reagent (20 mL) and dichloroethane (200 mL), and the mixture was stirred at 110° C. for 16 hours. The obtained reaction solution was poured into water (300 mL), and extracted with dichloromethane (200 mL×2). The combined organic phases were washed with saturated brine (200 mL), dried over anhydrous sodium sulfate, filtered and then concentrated under reduced pressure to obtain compound 12-3. LCMS (ESI) m/z: 219.5 [M+H]$^+$.

Step D: 12-3 (8 g, 36.66 mmol) was dissolved in dichloromethane (200 mL), and then p-toluenesulfonic acid monohydrate (3.49 g, 18.33 mmol) and 3,4-dihydropyran (4.63 g, 54.99 mmol) were added thereto. The mixture was stirred at 25° C. for 16 hours under nitrogen atmosphere. The obtained reaction solution was added with water (300 mL), and extracted with dichloromethane (200 mL×2). The combined organic phases were washed with saturated brine (200 mL), dried over anhydrous sodium sulfate, filtered and then concentrated under reduced pressure to obtain a crude product. The crude product was purified by column chromatography (eluent: petroleum ether/ethyl acetate=1/0 to 10/1) to obtain compound 12-4. LCMS (ESI) m/z: 303.1 [M+H]$^+$.

Step E: 12-4 (2.8 g, 9.26 mmol) was dissolved in tetrahydrofuran (30 mL), and a solution of potassium bis(trimethylsilyl)amide in tetrahydrofuran (1 mol/L, 13.89 mL, 13.89 mmol) was added thereto at −70° C. under nitrogen atmosphere. The mixture was stirred at−70° C. for 1 hour, and then a solution of potassium N-phenyl-bis(trifluoromethanesulfonyl) imide (4.96 g, 13.89 mmol) in tetrahydrofuran (30 mL) was added thereto, and the mixture was stirred at 15° C. for 15 hours. The obtained reaction solution was added with water (30 mL) and extracted with ethyl acetate (30 mL×2). The combined organic phases were washed with saturated brine (40 mL), dried over anhydrous sodium sulfate, filtered and then concentrated under reduced pressure to obtain a crude product. The crude product was purified by preparative HPLC (separation column: Unisil 3-100 C18 Ultra 150 mm×50 mm, particle size: 3 μm); mobile phase: [water (0.225% formic acid)-acetonitrile]; elution gradient: 65%-90%, 10 min) to obtain compound 12-5. LCMS (ESI) m/z: 435.1 [M+H]$^+$.

Step F: 12-5 (2 g, 4.60 mmol) and 2-10 (42.71 mg, 127.4 μmol) were dissolved in toluene (20 mL) and then tetrakis (triphenylphosphine)palladium (0) (532.02 mg, 460.40 μmol) and lithium chloride (234.22 mg, 5.22 mmol) were added thereto. The mixture was stirred at 100° C. for 16 hours under nitrogen atmosphere. The reaction solution was added with water (50 mL) and ethyl acetate (50 mL) to separate the phases, and extracted with ethyl acetate (30 mL×2). The combined organic phases were washed with saturated brine (50 mL), dried over anhydrous sodium sulfate, filtered and then concentrated under reduced pressure to obtain a crude product. The crude product was purified by column chromatography (eluent: petroleum ether/ethyl acetate=50/1 to 1/1) to obtain compound 12-6. LCMS (ESI) m/z: 534.1 [M+H]$^+$.

Step G: 12-6 (1.4 g, 1.38 mmol) was dissolved in tetrahydrofuran (15 mL), and a solution of pyridinium tribromide (484.22 mg, 1.51 mmol) in tetrahydrofuran (15 mL) was added thereto at 0 to 10° C. under nitrogen atmosphere. The mixture was stirred at 0 to 10° C. for 2 hours. The reaction was quenched with saturated sodium sulfite aqueous solution (50 mL). The reaction solution was added with water (30 mL) and ethyl acetate (50 mL) to separate the phases, and the aqueous phase was extracted with ethyl acetate (30 mL×2). The combined organic phases were washed with saturated brine (50 mL), dried over anhydrous sodium sulfate, filtered and then concentrated under reduced pressure to obtain compound 12-7. LCMS (ESI) m/z: 613.3, 615.3 [M+H]$^+$.

Step H: 12-7 (290 mg, 326.68 μmol, purity of 69%), 1,10-phenanthroline (11.77 mg, 65.34 μmol), cuprous iodide (12.44 mg, 65.34 μmol) and cesium carbonate (212.88 mg, 653.35 mol) were added to 2,2-difluoroethanol (0.6 mL). The reaction was stirred at 25° C. for 17 hours under nitrogen atmosphere. The obtained reaction solution was cooled and filtered, and the filtrate was diluted with water (10 mL) and ethyl acetate (10 mL×3) and then the phases were separated. The combined organic phases were washed with saturated brine (10 mL), dried over anhydrous sodium sulfate, filtered and then concentrated under reduced pressure to obtain a crude product. The crude product was purified by thin-layer silica gel chromatography (eluent: petroleum ether/ethyl acetate=1/2) to obtain compound 12-9. LCMS (ESI) m/z: 614.2 [M+H]$^+$.

Step I: 12-9 (116 mg, 189.03 μmol) was dissolved in ethyl acetate solution of hydrogen chloride (4 mol/L, 4 mL). The mixture was stirred at 35° C. for 1 hour. The obtained reaction solution was concentrated under reduced pressure to obtain the hydrochloride of 12-10. LCMS (ESI) m/z: 430.2 [M+H]$^+$.

Step J: N,N-Diisopropylethanamine (98.79 mg, 764.39 μmol) and 2-13 (35.92 mg, 191.10 μmol) were added to a solution of 12-10 (96 mg, 191.10 μmol, hydrochloride) in acetonitrile (3 mL), and the mixture was stirred at 35° C. for 12 hours. The reaction solution was concentrated under reduced pressure to obtain a crude product. The crude product was purified by preparative HPLC (separation column: Waters Xbridge 150×25 mm, particle size: m); mobile phase: [water (0.225% formic acid)-acetonitrile]; elution gradient: 1%-30%, 10 min) to obtain compound 12.

Compound 12: $^1$H NMR (400 MHz, DMSO-d$_6$) δ=12.41 (s, 1H), 8.21 (s, 1H), 7.78 (d, J=2.8 Hz, 1H), 7.29 (d, J=8.6 Hz, 1H), 7.15 (dd, J=2.6, 8.8 Hz, 1H), 6.85 (dd, J=2.9, 8.6 Hz, 1H), 6.78 (d, J=8.8 Hz, 1H), 6.34-6.03 (m, 2H), 4.52 (t, J=6.1 Hz, 1H), 4.40 (t, J=6.1 Hz, 1H), 4.11-3.94 (m, 3H), 3.71-3.65 (m, 2H), 2.94 (br t, J=6.9 Hz, 2H), 2.82 (t, J=7.0 Hz, 2H), 2.54-2.51 (m, 2H), 2.34 (quint, J=7.0 Hz, 2H), 2.15-2.08 (m, 2H), 1.74-1.59 (m, 2H). LCMS (ESI) m/z: 490.3 [M+H]$^+$.

Embodiment 13

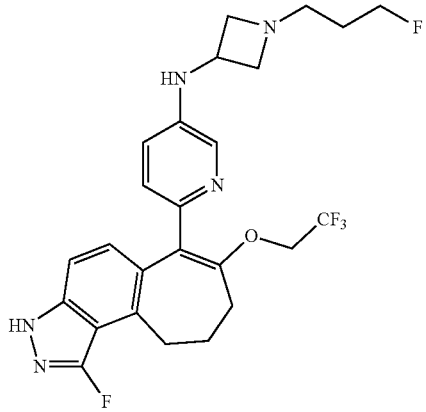

Synthetic Route:

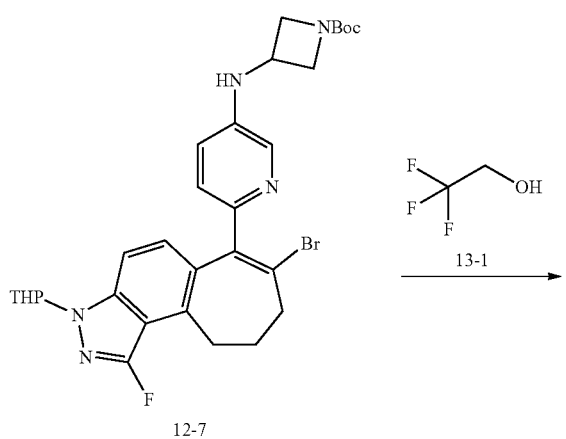

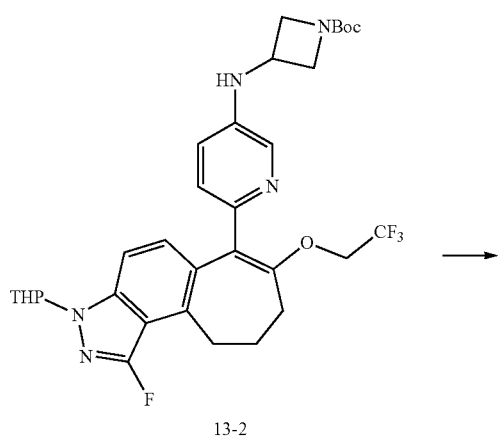

Step A: A solution of 12-7 (0.58 g, 653.36 μmol, purity of 69%), cuprous iodide (13.89 mg, 0.07294 mmol), 1,10-phenanthroline (13.14 mg, 0.07294 mmol) and cesium carbonate (237.64 mg, 0.72935 mmol) in 2,2,2-trifluoroethanol (2 mL) was stirred at 25° C. for 17 hours under nitrogen atmosphere. The mixture was diluted with ethyl acetate (10 mL) and water (10 mL) and then the phases were separated, and the aqueous phase was extracted with ethyl acetate (5 mL×2). The obtained organic phases were washed with saturated brine (10 mL), dried over anhydrous sodium sulfate, filtered and then concentrated under reduced pressure to a obtain a crude product of compound 13-2. LCMS (ESI) m/z: 632.2 [M+H]$^+$.

Step B: 13-2 (0.23 μg, 364.12 μmol) was dissolved in trifluoroacetic acid/dichloromethane (0.6 mL/3 mL) at 0 to 10° C. The mixture was stirred at 0 to 10° C. for 1 hour, then stirred at 25° C. for 15 hours. The reaction solution was concentrated under reduced pressure to obtain the formate of 13-3. LCMS (ESI) m/z: 448.2 [M+H]$^+$.

Step C: N,N-Diisopropylethanamine (184.16 mg, 1.42 mmol) and 2-13 (40.18 mg, 213.73 μmol) were added to a solution of 13-3 (0.2 g, 356.22 μmol, hydrochloride) in acetonitrile (5 mL), and the mixture was stirred at 35° C. for 16 hours. The mixture was diluted with dichloromethane (10 mL) and water (10 mL) and the phases were separated, and the pH of the mixture was adjusted to about 7 with saturated sodium bicarbonate, and the aqueous phase was extracted with dichloromethane (10 mL×2). The obtained organic phase was washed with saturated brine (20 mL), dried over anhydrous sodium sulfate, filtered and then concentrated under reduced pressure to obtain a crude product. The crude product was purified by preparative HPLC (separation column: Waters Xbridge 150 mm×25 mm, particle size: 5 m); mobile phase: [water (0.05% ammonia water)-acetonitrile]; elution gradient: 35%-63%, 9 min) and then purified by preparative thin-layer silica gel chromatography (eluent: dichloromethane/methanol=10/1) to obtain compound 13.

Compound 13: $^1$H NMR (400 MHz, CD$_3$OD) δ=7.83 (br s, 1H), 7.34 (br d, J=8.5 Hz, 1H), 7.16 (dd, J=2.3, 8.8 Hz, 1H), 7.01 (dd, J=2.6, 8.5 Hz, 1H), 6.82 (d, J=8.8 Hz, 1H), 4.55 (t, J=5.8 Hz, 1H), 4.43 (t, J=5.9 Hz, 1H), 4.24 (q, J=8.7 Hz, 2H), 4.15 (t, J=6.6 Hz, 1H), 3.90-3.80 (m, 2H), 3.15 (br t, J=7.0 Hz, 2H), 3.10-3.00 (m, 2H), 2.69 (t, J=7.5 Hz, 2H), 2.48 (quint, J=7.0 Hz, 2H), 2.30-2.20 (m, 2H), 1.90-1.70 (m, 2H). LCMS (ESI) m/z: 507.2 [M+H]$^+$.

Biological Test:

Experimental Embodiment 1: In Vitro Evaluation (1) MCF-7 Cell Proliferation Inhibition Experiment:
Experimental Materials:
EMEM culture medium was purchased from Wisent, and fetal bovine serum was purchased from Biosera, Promega CellTiter-Glo reagent. MCF-7 cell line was purchased from Cell Bank of Type Culture Collection of Chinese Academy of Sciences. Nivo5 multi-label analyzer (PerkinElmer).
Experimental Method:
MCF-7 cells were seeded in a white 384-well plate with 600 cells per well in every 45 mL of the cell suspension. The cell plate was placed in a carbon dioxide incubator and cultured overnight.

The test compound was diluted to the 10th concentration with a multi-channel pipette, and the compound concentration was 1 mM, 400 µM, and 80 µM, and then diluted to the 10th concentration of 1 nM in turn, and a double-duplicate experiment was set-up. 47.5 µL of culture medium was added to the middle plate, then 2.5 µL of gradient dilution compound per well was transferred to the middle plate according to the corresponding position, and 5 µL of the mixture per well was mixed evenly and transferred to the cell plate. The cell plate was placed in a carbon dioxide incubator and cultured for 6 days.

After 6 days of co-incubation of the compound, the culture medium was removed by centrifugation, and 25 µL of Promega CellTiter-Glo reagent was added to each well of the cell plate, and incubated at room temperature for 10 minutes to stabilize the luminescence signal. PerkinElmer Nivo multi-marker analyzer reading was used. In the experiment, the reading of 2 µM positive reference compound H3B-6545(US20160347717A1) was used as a positive control to participate in data calculation.

Data Analysis:
The equation % Inhibition=((RFU$_{Cmpd}$−AVER(RFU$_{Neg.ctrl}$))/((AVER(RFU$_{Pos.Ctrl}$)−AVER(RFU$_{Neg.ctrl}$))×100% was used to convert the original data into inhibition rate, and the compound curve was fitted by log(inhibitor)vs. response-Variable slope of Graphpad Prism 5. The IC$_{50}$ value was calculated by the software through the formula Y=Bottom+(Top−Bottom)/(1+10^((Log IC$_{50}$−X)*Hill-Slope)).

TABLE 1

Results of proliferation inhibition experiment of MCF-7

| Test compound | Anti-cell proliferation activity of MCF-7 (nM) |
|---|---|
| Formate of 1 | 0.42 |
| 2 | 0.42 |
| 3 | 1.37 |
| 5 | 0.19 |
| 6 | 0.31 |
| 8 | 0.70 |
| 11A | 0.17 |

(2) Degradation Experiment of MCF-7 ERα
Experimental Materials:
Phenol red-free MEM culture medium was purchased from Wisent, fetal bovine serum was purchased from Biosera, and Human Total ERα/NR3A1 ELISA kit was purchased from R&D. MCF-7 cell line was purchased from Cell Bank of Type Culture Collection of Chinese Academy of Sciences. Nivo5 multi-label analyzer (PerkinElmer).
Experimental Method:
Day 1:
MCF-7 cells were resuspended in culture medium (phenol red-free MEM+5% charcoal/dextran-treated fetal bovine serum+1% penicillin-streptomycin double antibody solution), and seeded in a clear 96-well cell culture plate with 80 µL per well containing 20,000 cells, and the cell culture plate was incubated overnight in a carbon dioxide incubator;

ELISA plate was coated with strips, human total estrogen receptor a capture antibody was diluted with 1×PBS with a final concentration of 1 µg/mL, and 100 µL of mixture was added to each well, and incubated overnight at 25° C.
Day 2:
Cell administration: The test compound was diluted to the 8th concentration with a multi-channel pipette, and the compound concentration was 20 µM and 4 µM, and then diluted to the 8th concentration of 0.256 nM in turn, and a double-duplicate experiment was set-up. 78 µL of culture medium was added to the middle plate, then 2 µL of gradient dilution compound per well was transferred to the middle plate according to the corresponding position, and 20 µL of the mixture per well was mixed evenly and transferred to the cell plate, and the final concentration of DMSO was 0.5%, and the mixture was incubated at 37° C. for 4 hours;

preparation of standard curve solution: 110 ng/mL of standard curve storage solution was 6-fold diluted with buffer (1×PBS containing 1 mM EDTA, 0.5% Triton X-100, pH 7.2 to 7.4) to obtain a solution with a concentration of 18.3 ng/mL, and then 91.5-fold diluted with buffer (1×PBS containing 1 mM EDTA, 0.5% Triton X-100, 1 M urea, pH 7.2 to 7.4) to obtain a solution with a concentration of 0.2 ng/mL, and 8-point gradient dilution was performed using buffer (1×PBS containing 1 mM EDTA, 0.5% Triton X-100, 1 M urea, pH 7.2 to 7.4) with a final concentration of 200 µg/mL to 1.56 µg/mL.

The ELISA plate was washed three times with 270 µL per well using a washing solution (1×PBS containing 0.05% Tween).

300 µL of blocking solution (1×PBS containing 1% bovine serum albumin) was added to each well and incubated at 25° C. for 2 hours;

1×PBS was pre-cooled, and after the incubation of the compound, the supernatant was removed, and then the plate was washed with 250 µL of pre-cooled 1×PBS per well, then 30 L of cell lysate per well (1×PBS containing 1 mM EDTA, 0.5% Triton X-100, 6 M urea, 1 mM active sodium orthovanadate, 2.5 mM sodium pyrophosphate, 1x protease inhibitor, pH 7.2 to 7.4) was added, and lysed on ice for 15 minutes;

the blocking solution was removed from ELISA plate, washed, and the step 3 was repeated;

after cell was lysed in the cell plate, the cell lysate was 6-fold diluted with 150 μL of buffer (1×PBS containing 1 mM EDTA, 0.5% Triton X-100, pH 7.2 to 7.4) per well, and the mixture was mixed evenly by blowing with a multi-channel pipette, and 100 μL of solution per well was transferred to the ELISA plate;

at the same time, 100 μL of standard curve solution per well was transferred to the ELISA plate and incubated overnight at 25° C.

Day 3:

The supernatant was removed, and the wash solution was used with 270 μL per well, and washed for three times;

the human total estrogen receptor a detection antibody stock solution (14.4 μg/mL) was 36-fold diluted with buffer (1×PBS containing 1% bovine serum albumin), and the final concentration of the detection antibody was 400 ng/mL, and 100 μL of the solution per well was transferred to the ELISA plate and incubated at 25° C. for 2 hours;

the plate was washed according to step 2;

streptavidin-horseradish peroxidase A was 200-fold diluted with buffer (1×PBS containing 1% bovine serum albumin), and 100 μL/well solution was transferred to the ELISA plate, and incubated at 25° C. for 20 minutes;

the plate was washed according to step 2;

100 μL of substrate solution per well (1:1 mixture of reagent A (30% hydrogen peroxide) and reagent B (TMB)) was added to the ELISA plate and incubated at 25° C. for 20 minutes;

50 μL of termination solution per well was added and the OD450 absorbance reading was performed on the plate reader.

Data analysis: A, B, C and D in the four-parameter equation $y=(A-D)/[1+(x/C)^B]+D$ were calculated according to the original data of the standard curve, wherein, y was the original OD450 value, x was the concentration of the corresponding point of the standard curve. According to the four-parameter equation and the OD450 reading of the original data of the sample, the concentration of ERα at the corresponding point was calculated. The equation (Sample−Min)/(Max−Min)×100% was used to convert the original data into inhibition rate, and the $IC_{50}$ value could be obtained by curve fitting with four parameters (obtained by "log (inhibitor) vs. response—variable slope" mode in GraphPad Prism). The degradation effect of the compound of the present disclosure on ERα is provided in Table 2.

Max wells: Positive control wells reading at 100 nM Fulvestrant-treated cell wells Min wells: Negative control wells reading at 0.5% DMSO-treated cell wells

TABLE 2

Experimental results of ERα degradation in MCF-7 cell line

| Compound | $IC_{50}$ value (nM) of promoting ERα degradation |
| --- | --- |
| Formate of 1 | 0.25 |
| 2 | 0.20 |
| 3 | 0.45 |
| 4 | 0.17 |
| 5 | 0.017 |
| 6 | 0.42 |
| 7 | 0.40 |

TABLE 2-continued

Experimental results of ERα degradation in MCF-7 cell line

| Compound | $IC_{50}$ value (nM) of promoting ERα degradation |
| --- | --- |
| 8 | 0.37 |
| 11A | 0.23 |

Conclusion:

The compound of the present disclosure has obvious degradation effect on ERα in vitro, and has significant anti-proliferation activity on MCF-7 cells.

Experimental Embodiment 2: DMPK Property Evaluation (1) Study on Cytochrome P450 Isoenzyme Inhibition Experimental purposes: To test the inhibitory effect of test compound on the activity of human liver microsomal cytochrome P450 isoenzymes (CYP1A2 and CYP3A4) (Corning, Co., Ltd.).

Experimental operation: Firstly, the test compound (10 mM) was subjected to gradient dilution to prepare a working solution (100×final concentration), and the concentration of the working solution was: 5, 1.5, 0.5, 0.15, 0.05, 0.015 and 0.005 mM, respectively, and the working solution of each positive inhibitor of P450 isoenzyme (CYP1A2 and CYP3A4) and its specific substrate mixture (5 in 1) were prepared; and then the human liver microsomes frozen in the −80° C. refrigerator were thawed on ice, and all the human liver microsomes were dissolved, diluted with PB, and a certain concentration of working solution (0.253 mg/mL) was prepared; 20 μL of substrate mixture was added to the reaction plate (20 μL of PB was added to the blank well), while 158 μL of human liver microsomal working solution was added to the reaction plate, and the reaction plate was placed on ice for later use; at this time, 2 μL of various concentrations of the test compound (N=1) and specific inhibitor (N=2) were added to the corresponding well, and the corresponding organic solvent was added to the non-inhibitor (test compound or positive inhibitor) group as a control group sample (a ratio of DMSO:MeOH in the test compound control sample was 1:1, a ratio of DMSO:MeOH in the positive control sample was 1:9); after pre-incubation in a water bath at 37° C. for 10 min, 20 μL of coenzyme factor (NADPH) solution was added to the reaction plate, and incubated in a water bath at 37° C. for 10 min; and 400 μL of cold acetonitrile solution (internal standard was 200 ng/mL tolbutamide and labetalol) was added to terminate the reaction; the reaction plate was placed on a shaker and shaked for 10 minutes; and then centrifuged at 4,000 rpm for 20 minutes; 200 μL of the supernatant was taken and added to 100 μL of water for sample dilution; finally the plate was sealed, shaked and shaked well, for LC/MS/MS detection. The results are shown in Table 3.

TABLE 3

Evaluation results of isoenzyme inhibition of cytochrome P450

| | Isoenzyme $IC_{50}$ (μM) | |
| --- | --- | --- |
| Compound | CYP1A2 | CYP3A4 |
| 2 | >50 | 47.2 |
| 3 | >50 | 13.6 |
| 4 | >50 | 11.1 |
| 8 | >50 | 42.1 |

TABLE 3-continued

Evaluation results of isoenzyme inhibition of cytochrome P450

| Compound | Isoenzyme $IC_{50}$ (μM) | |
| --- | --- | --- |
| | CYP1A2 | CYP3A4 |
| 10 | 47.5 | 30.8 |
| 11A | >50 | 25.7 |

Conclusion: The compound of the present disclosure has no obvious inhibition on CYP enzyme, which indicates that there is low risk of related drug interaction.

(2) In Vivo Pharmacokinetic Study in Mice

Experimental purposes: To test the drug concentration in plasma of mice at different times after intravenous and intragastric administration of the test compound by LC/MS/MS using female Balb/c mice as the experimental animals. To study the pharmacokinetics of the test compound in mice in vivo and evaluate their pharmacokinetic characteristics.

Experimental Protocol:

Experimental animals: 4 healthy female Balb/c mice were divided into 2 groups according to the principle of similar body weight, with 2 mice in each group in IV group and 2 mice in each group in PO group. Animals were purchased from Shanghai Lingchang Biotechnology Co., Ltd.

Drug Preparation:

Appropriate number of samples were weighed and prepared into 1 mg/mL solution respectively, and the mixture was stirred and ultrasonicated to reach a clear state, and the solvent was 15% HP-β-CD.

Administration: After fasting overnight, IV group was administered intravenously, and the dosage of the test compound was 5 mg/kg; PO group was administered intragastrically, and the dosage of the test compound was 10 mg/kg.

Experimental Operation:

After the female Balb/c mice in the intravenous injection group were given the test compound respectively, 30 μL of blood was collected from the saphenous vein at 0.0833, 0.25, 0.5, 1, 2, 4, 8, and 24 hours, and placed in a commercialized anticoagulant tube added with EDTA-$K_2$ in advance. After intragastric administration of the test compound, 30 μL of blood was collected from the saphenous vein at 0.25, 0.5, 1, 2, 4, 8, 12 and 24 hours, respectively, and placed in a commercialized anticoagulant tube added with EDTA-$K_2$ in advance. After centrifugation (3,200 g, 4° C., 10 minutes), the plasma was collected, transferred to a pre-cooled centrifuge tube, quickly frozen in dry ice, and stored in a refrigerator at −60° C. or lower, until LC-MS/MS analysis. Animals were allowed to eat 4 hours after administration. LC/MS/MS method was used to determine the content of the test compound in the plasma of mice after intravenous and intragastric administration. The linear range of the method was 2.00 to 2000 nM.

The experimental results are shown in Table 4.

TABLE 4

Evaluation results of PK properties in mice in vivo

| | Parameter | PK properties of mice | |
| --- | --- | --- | --- |
| | | Compound 2 | Compound 11A |
| i.v. (5 mg/kg) | $T_{1/2}$ (h) | 6.85 | 5.16 |
| | $Vd_{ss}$ (L/kg) | 10.6 | 11.1 |
| | Cl (mL/min/kg) | 18.3 | 30.2 |
| | $AUC_{0\text{-}last}$ (nM · h) | 8469 | 5270 |
| p.o. (10 mg/kg) | $C_{max}$ (nM) | 937 | 779 |
| | $T_{1/2}$ (h) | 7.67 | 4.72 |
| | $AUC_{0\text{-}last}$ (nM · h) | 11722 | 5856 |
| | F % | 71.8 | 55.4 |

Conclusion: The compound of the present disclosure has stable metabolism, large tissue distribution and high oral absorption in mice, which indicates that the compound has good pharmacokinetic characteristics in vivo.

(3) In Vivo Pharmacokinetic Study in Rats

Experimental purposes: To test the drug concentration in plasma of rats at different times after intravenous and intragastric administration of the test compound by LC/MS/MS using male fasted SD rats as the experimental animals. To study the pharmacokinetics of the test compound in rats in vivo and evaluate their pharmacokinetic characteristics.

Experimental Protocol:

Experimental animals: 4 healthy male SD rats were divided into 2 groups according to the principle of similar body weight, with 2 mice in each group in IV group and 2 mice in each group in PO group. Animals were purchased from Beijing Vital River Laboratory Animal Co., Ltd.

Drug Preparation:

IV group: Appropriate number of samples were weighed and prepared into 0.5 mg/mL solution respectively, and the mixture was stirred and ultrasonicated to reach a clear state, and the solvent was 15% HP-β-CD.

PO group: Appropriate amount of the solution prepared in IV group was diluted to 0.4 mg/mL with 15% HP-β-CD.

Administration: After fasting overnight, IV group was administered intravenously, and the dosage of the test compound was 1 mg/kg; PO group was administered intragastrically, and the dosage of the test compound was 2 mg/kg.

Experimental Operation:

After the male rats in the intravenous injection group were given the test compound respectively, 200 μL of blood was collected from the jugular vein at 0.0833, 0.25, 0.5, 1, 2, 4, 8, and 24 hours, and placed in a commercialized anticoagulant tube added with EDTA-$K_2$ in advance. After intragastric administration of the test compound, 200 μL of blood was collected from the jugular vein at 0.25, 0.5, 1, 2, 4, 8, 12 and 24 hours, respectively, and placed in a commercialized anticoagulant tube added with EDTA-$K_2$ in advance. After centrifugation (3,200 g, 4° C., 10 minutes), the plasma was collected, transferred to a pre-cooled centrifuge tube, quickly frozen in dry ice, and stored in a refrigerator at −60° C. or lower, until LC-MS/MS analysis. Animals were allowed to eat 4 hours after administration. LC/MS/MS method was used to determine the content of the test compound in the plasma of rats after intravenous and intragastric administration. The linear range of the method was 2.00 to 2000 nM. The experimental results are shown in Table 5.

Conclusion: The compound of the present disclosure has stable metabolism, large tissue distribution and high oral absorption in rats in vivo, which indicates that the compound has good pharmacokinetic characteristics in vivo.

(4) In Vivo Pharmacokinetics Study in Dogs

Experimental purposes: To test the drug concentration in plasma of beagle dogs at different times after intravenous and intragastric administration of the test compound by LC/MS/MS using beagle dogs as the experimental animals. To study the pharmacokinetics of the test compound in beagle dogs in vivo and evaluate their pharmacokinetic characteristics.

Experimental Protocol:

Experimental Animal:

Two healthy male and two female beagle dogs were divided into two groups according to the principle of similar body weight, with one male and one female in IV group and one male and one female in PO group. Animals were purchased from Beijing Marshall Biotechnology Co., Ltd.

Drug Preparation:

IV group: Appropriate number of samples were weighed and prepared into 1 mg/mL solution respectively, and the mixture was stirred and ultrasonicated to reach a clear state, and the solvent was 10% HP-β-CD, and the pH value was adjusted to 5.74.

PO group: Appropriate amount of the solution prepared in IV group was diluted to 0.2 mg/mL with 10% HP-β-CD, and the pH value was adjusted to 5.8.

Administration: After fasting overnight, IV group was administered intravenously, and the dosage of the test compound was 1 mg/kg; PO group was administered intragastrically, and the dosage of the test compound was 2 mg/kg.

Experimental Operation:

After the beagle dogs in the intravenous injection group were given the test compound respectively, and 200 μL of blood was collected from the peripheral vein at 0.0833, 0.25, 0.5, 1, 2, 4, 6, 8, 12 and 24 hours, and placed in a commercialized anticoagulant tube added with EDTA-$K_2$ in advance. After intragastric administration of the test compound, 200 μL of blood was collected from the peripheral vein at 0.25, 0.5, 1, 2, 4, 6, 8, 12 and 24 hours, respectively, and placed in a commercialized anticoagulant tube added with EDTA-$K_2$ in advance. After centrifugation (3,200 g, 4° C., 10 minutes), the plasma was collected, transferred to a pre-cooled centrifuge tube, quickly frozen in dry ice, and stored in a refrigerator at −60° C. or lower, until LC-MS/MS analysis. Animals were allowed to eat 4 hours after administration. LC/MS/MS method was used to determine the content of the test compound in the plasma of beagle dogs after intravenous and intragastric administration. The linear range of the method was 2.00 to 2000 nM.

The experimental results are shown in Table 5.

TABLE 5

Evaluation results of PK properties in rats and dogs in vivo

| Parameter | | PK properties of rats | | PK properties of dogs |
|---|---|---|---|---|
| | | Compound 2 | Compound 11A | Compound 11A |
| i.v. (1 mg/kg) | $T_{1/2}$ (h) | 3.62 | 3.19 | 23.1 |
| | $Vd_{ss}$ (L/kg) | 15.9 | 14.5 | 6.60 |
| | Cl (mL/min/kg) | 54.6 | 53.1 | 3.44 |
| | $AUC_{0\text{-}last}$ (nM · h) | 493 | 518 | 5078 |
| p.o. (2 mg/kg) | $C_{max}$ (nM) | 39.3 | 66.9 | 495 |
| | $T_{1/2}$ (h) | 5.80 | 8.96 | 19.2 |
| | $AUC_{0\text{-}last}$ (nM · h) | 240 | 601 | 7963 |
| | F % | 24.3 | 58.1 | 78.2 |

Conclusion: The compound of the present disclosure as stable metabolism, large tissue distribution and high oral absorption in dogs in vivo, which indicates that the compound has good pharmacokinetic characteristics in vivo.

(5) Study on Protein Binding in Human Plasma

Plasma protein binding is a key factor to control the amount of free (unbound) drugs available for binding to the target, so it plays an important role in the observed efficacy of drugs in vivo. Compound with high free fraction (low levels of plasma protein binding) can exhibit enhanced efficacy relative to the compound with similar potency and exposure levels. The compound of the present disclosure was tested by ultracentrifugation. After that, plasma and buffer samples were prepared for analysis by liquid chromatography and mass spectrometry. Compounds were pooled in plasma pools of up to 10 compounds. Three reference compounds Propranolol, Metoprolol and Warfarin were used in each run. Warfarin was used as a control in each pool, and Propranolol and Metoprolol were randomly placed in each run. The compound of the present disclosure has a good free fraction, that is, a low level of plasma protein binding, showing a certain degree of enhanced efficacy.

Experimental Embodiment 3: In Vivo Efficacy Evaluation

The purpose of this experiment was to evaluate the antitumor effect of the compound of the present disclosure on MCF-7 breast cancer cell xenograft BALB/c nude mice (provided by the Experimental Animal Management Department of the Shanghai Institute of Family Planning Sciences, and the number of test animals in each experimental group was 5) model.

Mice were subcutaneously inoculated with 0.36 mg, 60-day slow-release estrogen tablets in the left shoulder three days before inoculation. When the cells were in the logarithmic growth phase, the cells were collected and counted, and the cell concentration was adjusted to $10 \times 10^7$ cells/mL, and an equal volume of Matrigel was added to mix evenly and then used for inoculation. Each mouse was subcutaneously inoculated with 0.2 mL of MCF-7 tumor cell suspension ($10 \times 10^6$) on the right shoulder. On day 9 after tumor cell inoculation, the average tumor volume was 160 $mm^3$ and the body weight was 22.0 to 23.0 g, which was administered in groups and administered once a day. Tumor volume and weight measurements were performed twice a week after grouping, and tumor proliferation rate (T/C) and tumor growth inhibition rate (TGI) were calculated for the last tumor volume data on the day 21 after grouping, and the antitumor effect of compounds was evaluated by TGI (%) or relative tumor proliferation rate T/C (%). TGI (%), reflecting the tumor growth inhibition rate. TGI (%)=[(1-(average tumor volume at the end of administration of a certain treatment group-average tumor volume at the beginning of administration of this treatment group)/(average tumor volume at the end of treatment in the solvent control group-average tumor volume at the beginning of treatment in this solvent control group)]×100%, relative tumor proliferation rate T/C (%)=$T_{RTV}/C_{RTV} \times 100\%$ ($T_{RTV}$: average RTV of the treatment group; $C_{RTV}$: average RTV of the negative control group). The relative tumor volume (RTV) was calculated according to the results of tumor measurement, and the formula was RTV=$V_t/V_0$, wherein $V_0$ was the average tumor volume measured at the time of group administration (i.e., $D_0$), and $V_t$ was the tumor volume at a certain measurement, $T_{RTV}$ and $C_{RTV}$ were taken on the same day. The results are shown in Table 6.

TABLE 6

Analysis of anti-tumor effect

| Parameter | | Compound 2 (5 mg/kg) | Compound 11A (5 mg/kg) |
|---|---|---|---|
| Tumor volume ($mm^3$)[a] | Day 0 | 161 | 160 |
| | Day 4 | 169 | 184 |
| | Day 7 | 182 | 195 |
| | Day 11 | 186 | 200 |
| | Day 14 | 163 | 176 |
| | Day 18 | 133 | 126 |
| | Day 21 | 118 | 112 |
| T/C (%) (Day 21) | | 12.3 | 12.8 |
| TGI (%) (Day 21) | | 106 | 107 |
| p | | <0.001 | <0.001 |

Conclusion: The compound of the present disclosure exhibits excellent tumor inhibition efficacy in the mouse pharmacodynamic model, and has good clinical therapeutic potential.

Experiment Embodiment 4: Uterine Wet Weight Inhibition Experiment in Rat Cubs

The purpose of this experiment was to evaluate the effect of the compound of the present disclosure on uterine growth inhibition in 18 to 21-day-old female rat pups (provided by Beijing Vital River Laboratory Animal Technology Co., Ltd.). In this experiment, 18-day-old female rat pups were orally administered the compound of the present disclosure at a dose of 25 mg/kg for three consecutive days, and the control group was orally administered 0.1 mg/kg of Ethinylestradiol for three consecutive days, and the blank group was not given any drug except the corresponding solvent. Three days after the administration, the rats were sacrificed, and the weight of the rat uterus was weighed to observe the effect of the test drug on the growth inhibition of the rat uterus. Inhibition rate=100×[(Vehicle$_{EE}$−Cpd)/(Vehicle$_{EE}$−Vehicle)], Vehicle$_{EE}$ was the wet weight of the rat uterus in the control group (administered 0.1 mg/kg of Ethinylestradiol orally); Cpd was the wet weight of the rat uterus in administration group; Vehicle was the wet weight of the rat uterus in the blank group. The results are shown as follows:

| Test drug | Uterine wet weight (mg) | Inhibition rate (%) | Ratio of uterine wet weight/rat body weight (mg/g) |
|---|---|---|---|
| Blank group | 48.88 | / | 1.02 |
| Ethinylestradiol | 132.2 | 0 | 2.45 |
| Compound 2 | 52.34 | 95.8 | 0.84 |
| Compound 11A | 49.725 | 99.0 | 1.05 |

Conclusion: The effect of the compound of the present disclosure on the wet weight of the uterus of female rat pups is comparable to that of the blank control group, and does not exhibit the effect of uterine proliferation, which indicates good clinical medication safety and avoids the risk of endometrial cancer caused by clinical medication.

The invention claimed is:

1. A compound represented by formula (II) or a pharmaceutically acceptable salt thereof

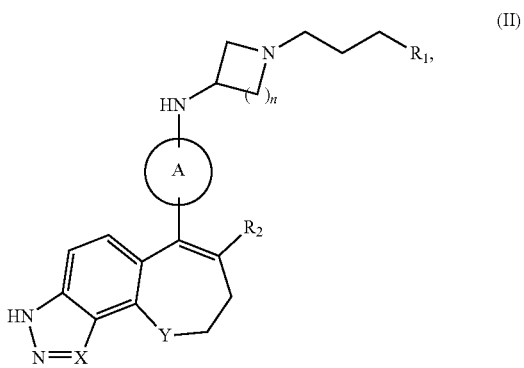

wherein,
n is 1 or 2;
X is selected from N and CR$_3$;
Y is selected from —O— and —CH$_2$—;
L is selected from —O—, —N(CH$_3$)— and —NH—;
ring A is selected from phenyl, pyridyl, pyrazinyl and pyrimidyl, and the phenyl, pyridyl, pyrazinyl and pyrimidyl are each independently and optionally substituted by 1, 2 or 3 R$_a$;
R$_1$ is selected from CN and F;
R$_2$ is selected from C$_{1-6}$ alkyl, C$_{1-6}$ alkoxy and C$_{3-6}$ cycloalkyl, and the C$_{1-6}$ alkyl, C$_{1-6}$ alkoxy and C$_{3-6}$ cycloalkyl are each independently and optionally substituted by 1, 2 or 3 R$_b$;
R$_3$ is selected from D, F and H;
R$_a$ is each independently selected from H, D, F, Cl, Br, I, OH, CN, OCH$_3$, OCH$_2$CH$_3$, C$_{1-4}$ alkyl,

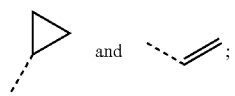

R$_b$ is each independently selected from F, Cl, Br, I, CN, OH and OCH$_3$.

2. The compound or the pharmaceutically acceptable salt thereof as claimed in claim 1, wherein, ring A is selected from

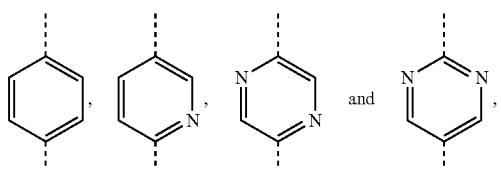

and the

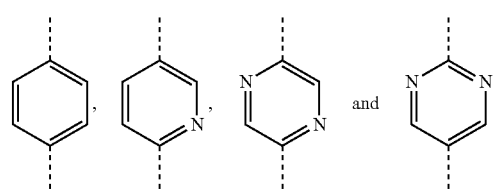

are each independently and optionally substituted by 1, 2 or 3 R$_a$.

3. The compound or the pharmaceutically acceptable salt thereof as claimed in claim 1, wherein, $R_a$ is each independently selected from H, D, F, Cl, OH, CN, OCH$_3$ and CH$_3$.

4. The compound or the pharmaceutically acceptable salt thereof as claimed in claim 2, wherein, ring A is selected from

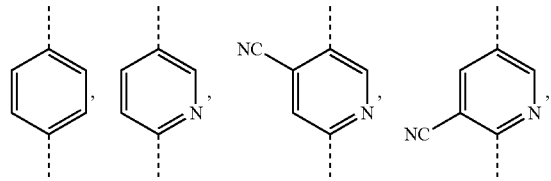

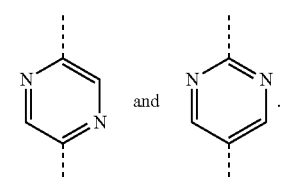

5. The compound or the pharmaceutically acceptable salt thereof as claimed in claim 1, wherein, $R_2$ is selected from C$_{1-3}$ alkyl and C$_{1-3}$ alkoxy, and the C$_{1-3}$ alkyl and C$_{1-3}$ alkoxy are each independently and optionally substituted by 1, 2 or 3 $R_b$.

6. The compound or the pharmaceutically acceptable salt thereof as claimed in claim 5, wherein, $R_2$ is selected from

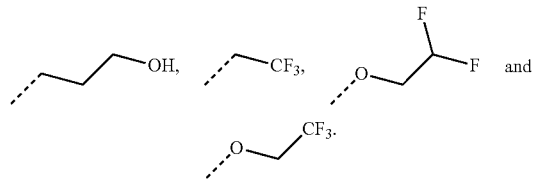

7. The compound or the pharmaceutically acceptable salt thereof as claimed in claim 1, wherein, the compound is selected from

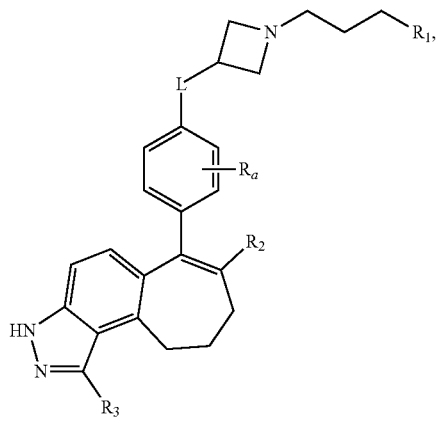
(I-1)

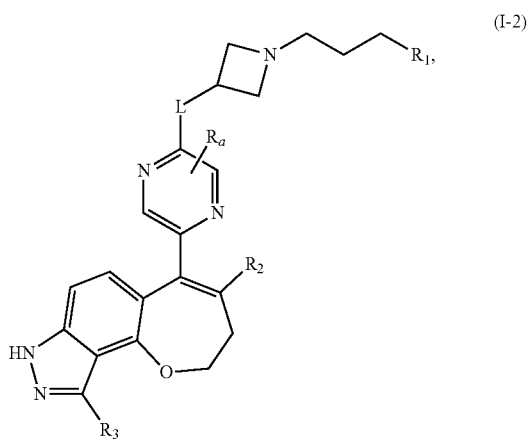
(I-2)

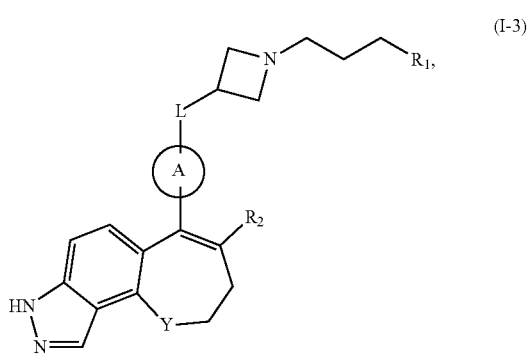
(I-3)

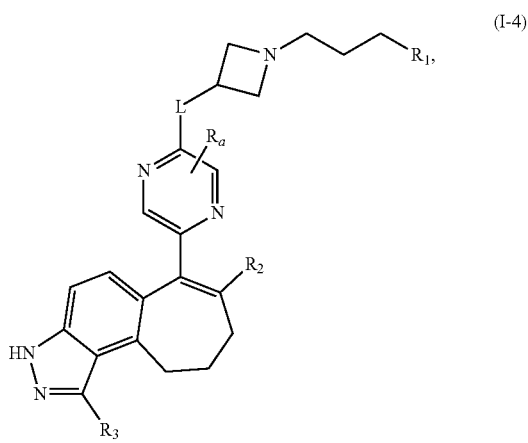
(I-4)

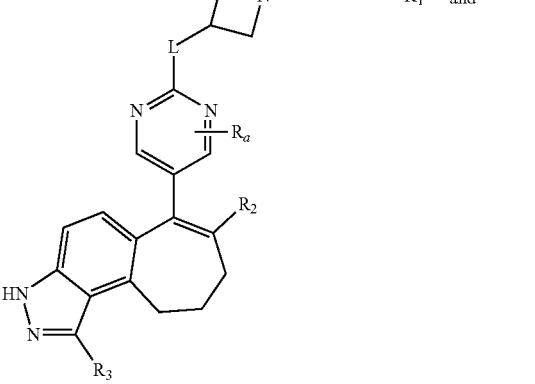
(I-5) and

-continued
(II-1)
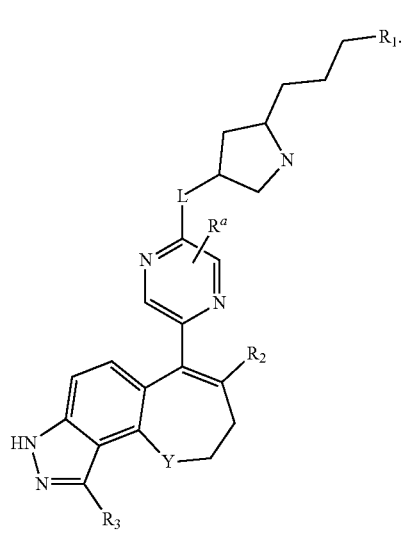
8. A compound represented by the following formula or a pharmaceutically acceptable salt thereof, selected from
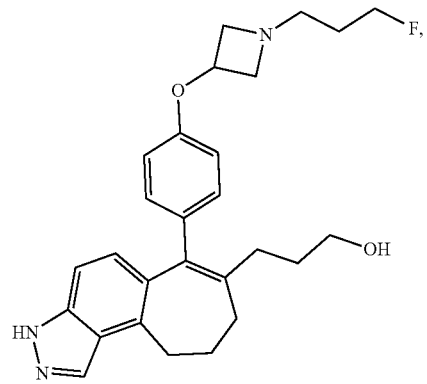
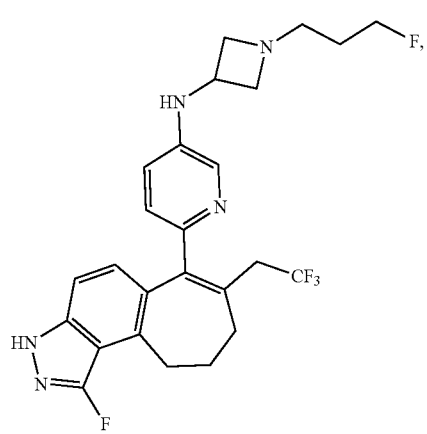
-continued
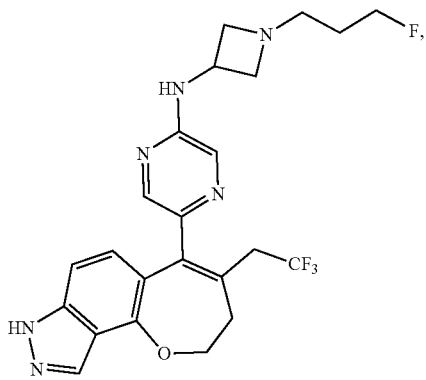
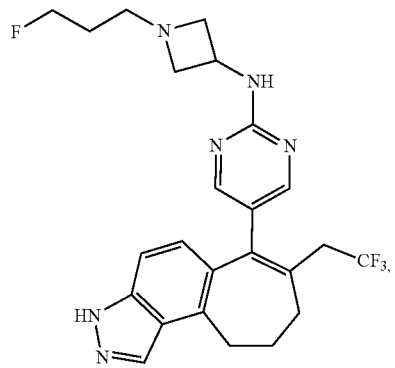
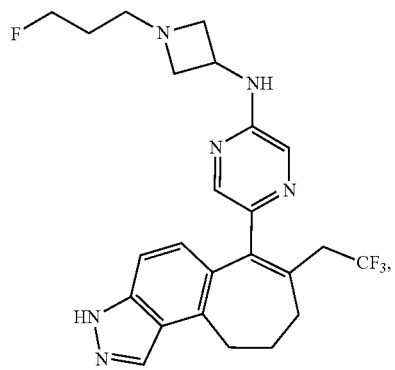
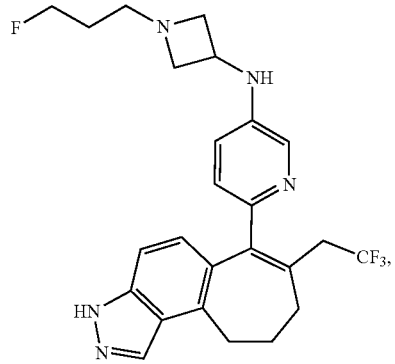

85
-continued
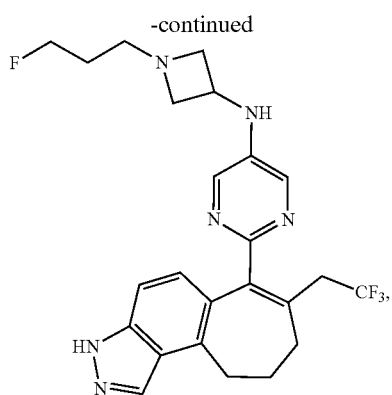
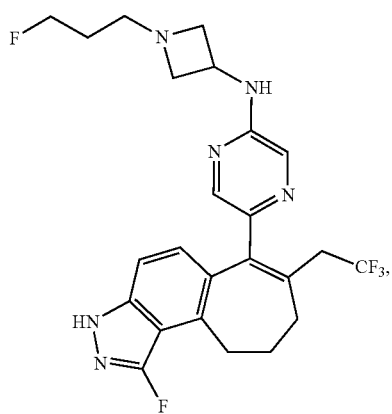
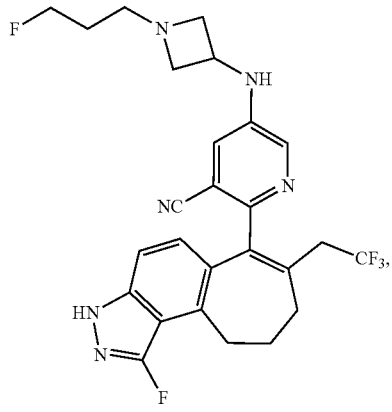
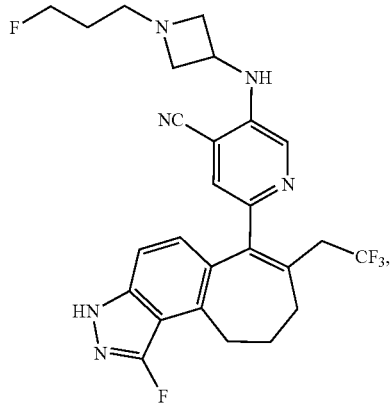
86
-continued
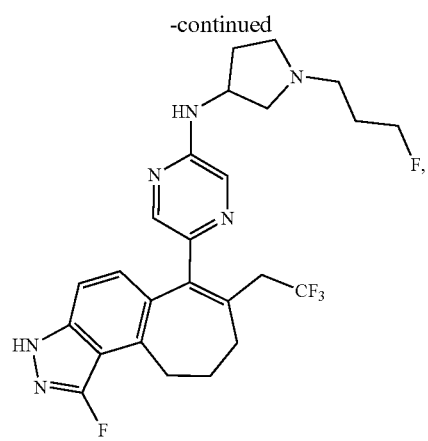
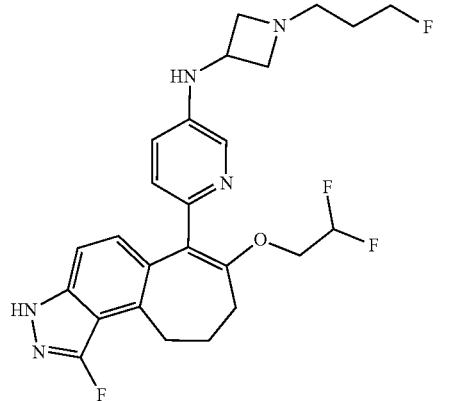
and
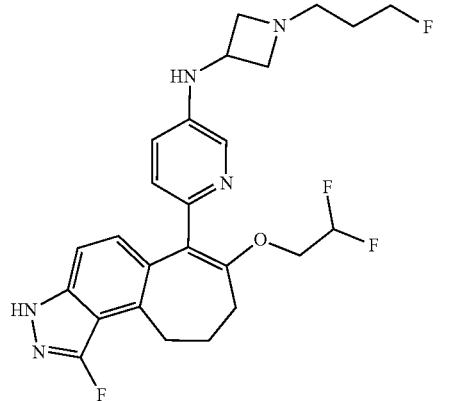

9. The compound or the pharmaceutically acceptable salt thereof as claimed in claim 8, wherein, the compound is selected from

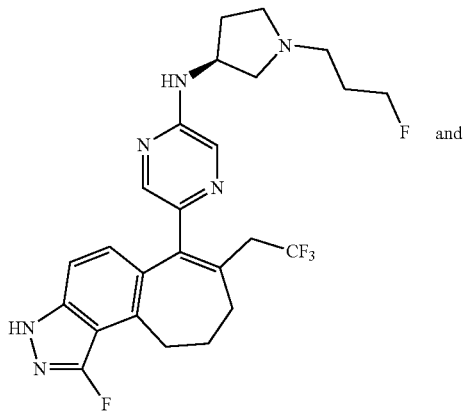

and

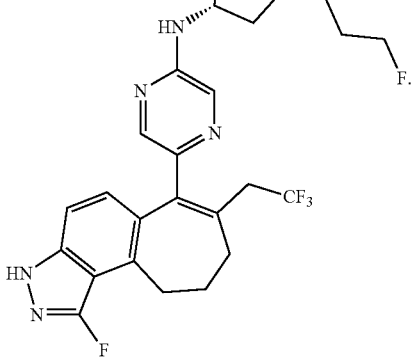

10. A method for treating breast cancer in a subject in need thereof, comprising: administering the compound or the pharmaceutically acceptable salt thereof as claimed in claim 1 to the subject.

11. The method as claimed in claim 10, wherein, the breast cancer is estrogen receptor positive breast cancer.

* * * * *